(12) United States Patent
Nagy

(10) Patent No.: US 10,829,817 B2
(45) Date of Patent: Nov. 10, 2020

(54) THERAPEUTIC TARGETS FOR ALZHEIMER'S DISEASE

(71) Applicant: THE UNIVERSITY OF BIRMINGHAM, Birmingham, West Midlands (GB)

(72) Inventor: Zsuzsanna Nagy, Birmingham (GB)

(73) Assignee: THE UNIVERSITY OF BIRMINGHAM, Birmingham (GB)

( * ) Notice: Subject to any disclaimer, the term of this patent is extended or adjusted under 35 U.S.C. 154(b) by 0 days.

(21) Appl. No.: 15/922,184

(22) Filed: Mar. 15, 2018

(65) Prior Publication Data

US 2019/0203293 A1 Jul. 4, 2019

Related U.S. Application Data

(62) Division of application No. 14/413,659, filed as application No. PCT/GB2013/051843 on Jul. 11, 2013, now Pat. No. 9,944,986.

(30) Foreign Application Priority Data

Jul. 11, 2012 (GB) .................................. 1212334.5

(51) Int. Cl.
| | |
|---|---|
| C12Q 1/68 | (2018.01) |
| C12Q 1/6883 | (2018.01) |
| C12N 15/113 | (2010.01) |
| A61K 31/436 | (2006.01) |
| G01N 33/50 | (2006.01) |

(52) U.S. Cl.
CPC .......... *C12Q 1/6883* (2013.01); *A61K 31/436* (2013.01); *C12N 15/113* (2013.01); *G01N 33/5023* (2013.01); *C12N 2310/14* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2002/0015941 A1 | 2/2002 | Kim et al. |
| 2003/0092019 A1 | 5/2003 | Meyer et al. |

FOREIGN PATENT DOCUMENTS

| | | |
|---|---|---|
| WO | 2011/001135 A9 | 1/2011 |
| WO | 2011/012672 A1 | 2/2011 |

OTHER PUBLICATIONS

Abramsson et al., "No Association of LOXL1 Gene Polymprophisms with Alzheimer's Disease", Neuromol. Med., 13: 160-166 (2011).
Bonda et al., "Novel therapeutics for Alzheimer's disease: An update", Curr. Opin. Drug Discov. Devel., 13(2): 235-246 (2010).
Bove et al., "Fighting neurodegeneration with rapamycin: mechanistic insights", Nature Reviews, Neuroscience, 12: 437-452 (2011).
Caccamo et al., "Molecular Interplay between Mammalian Target of Rapamycin (mTOR), Amyloid-B, and Tau", J. Biol. Chem., 285(17): 13107-13120 (2010).
Cai et al., "Mammalian Target of Rapamycin: A Valid Therapeutic Target Through the Autophagy Pathway for Alzheimer's Disease?", Journal of Neuroscience Research, 90: 1105-1118 (2012).
Cascalheira et al., "Serum homocysteine: Interplay with other circulating and genetic factors in association to Alzheimer's type dementia", Clinical Biochemistry, 42: 783-790 (2009).
Clifford et al., "Large-scale analysis of non-synonymous coding region single nucleotide polymorphisms", Bioinformatics, 20(7): 1006-1014 (2004).
Erikkson et al., "Associations of gene sequence variation and serum levels of C-reactive protein and Interleukin-6 with Alzheimer's disease and dementia", J. Alzheimers Dis., 23(2): 361-369 (2011).
Finckh, "The Future of genetic association studies in Alzheimer disease", J. Neural. Transm, 110: 253-266 (2003).
Forlenza et al., "Diagnosis and biomarkers of predementia in Alzheimer's disease", BMC Medicine, 8: 89 (2010).
Gustaw-Rothenberg et al., "Biomarkers in Alzheimer's disease: past, present and future", Biomark. Med., 4(1): 15-26 (2010).
Heinonen et al., "Deciphering downstream gene targets of P13K/mTOR/p70S6K pathway in breast cancer", BMC Genomics, 9: 348 (2008).
Hong et al., "Genome-Wide and Gene-Based Association Implicates FRMD6 in Alzheimer Disease", Human Mutation, 33(3): 521-529 (2012).
Flex et al., "Polymorphisms of the Macrophage Inhibitory Factor and C-Reactive Protein Genes in Subjects with Alzheimer's Dementia", Dement. Geriatr. Cogn. Disord., 18: 261-264 (2004.
Kok et al., "CRP gene variation affects early development of Alzheimer's disease-related plaques", Journal of Neuroinflammation, 8: 96 (2011).
Kramer et al., "Alzheimer disease pathology in cognitively healthy elderly: A genome-wide study", Neurobiology of Aging, 32: 2113-2122 (2011).
Lesseux et al., "Syk-dependent mTOR activation in follicular lymphoma cells", Blood, 108(13): 4156-4162 (2006).
Li et al., "Levels of mTOR and its downstream targets 4E-BP1, eEF2, and eEF2 kinase in relationships with tau in Alzheimer's disease brain", FEBS Journal, 272: 4211-4220 (2005).
Liu et al., "A Genomewide Screen for Late-Onset Alzheimer Disease in a Genetically Isolated Dutch Population", The American Journal of Human Genetics, 81: 17-31 (2007).

(Continued)

*Primary Examiner* — Katherine D Salmon
(74) *Attorney, Agent, or Firm* — Robert C. Netter, Jr.; Dann, Dorfman, Herrell & Skillman

(57) ABSTRACT

The present invention relates to novel methods for the prevention, treatment and diagnosis of Alzheimer's disease. In addition, the invention relates to methods for assessing an individual's susceptibility or pre-disposition to Alzheimer's disease. The methods of the present invention involve the use of therapeutic targets and diagnostic and/or predictive markers within the mTOR signalling pathway. The methods also involve screening subjects for genetic polymorphisms associated with rapamycin-sensitive genes.

3 Claims, 34 Drawing Sheets

Specification includes a Sequence Listing.

(56) References Cited

OTHER PUBLICATIONS

McKhann et al., "Clinical diagnosis of Alzheimer's disease: Report of the Nincds-Adrda Work Group* under the auspices of Department of Health and Human Services Task Force on Alzheimer's Disease", Neurology, 34: 939-944 (1984).
Mendelsohn et al., "Rapamycin As an Antiaging Therapeutic?: Targeting Mammalian Target of Rapamycin to Treat Hutchinson-Gilford Progereia and Neurodegenerative Diseases", Rejuvenation Research, 14(4): 437-441 (2011).
Morita et al., "Association Study Between C-Reactive Protein Genes and Ischemic Stroke in Japanese Subjects", AJH, 19: 593-600 (2006).
Morita et al., "Polymorphism of the C-Reactive Protein (CRP) Gene is Related to Serum CRP Level and Arterial Pulse Wave Velocity in Healthy Elderly Japanese", Hypertens. Res., 29: 323-331 (2006).
Nagy, "The dysregulation of the cell cycle and the diagnosis of Alzheimer's disease", Biochimica et Biophysica Acta, 1772: 402-408 (2007).
Oddo, "The role of mTOR signaling in Alzheimer's disease", Frontiers in Bioscience, S4: 941-952 (2012).
Perry et al., "A New Alzheimer's Disease Interventive Strategy: GLP-1", Current Drug Targets, 5: 565-571 (2004).
Perry et al., "Enhancing Central Nervous System Endogenous GLP-1 Receptor Pathways for Intervention in Alzheimer's Disease", Current Alzheimer Research, 2: 377-385 (2005).
Santos et al., "Effects of rapamycin and TOR on aging and memory: implications for Alzheimer's disease", Journal of Neurochemistry, 117: 927-936 (2011).
Sun et al., "Protective Effects of Bone Morphogenetic Protein 7 Against Amyloid-Beta Induced Neurotoxicity in PC12 Cells", Neuroscience, 184: 151-163 (2011).
Ueberham et al., "Altered subcellular location of phosphorylated SMads in Alzheimer's disease", European Journal of Neuroscience, 24: 2327-2334 (2006).
Oijen et al., "Polymorphisms and haplotypes in the C-reactive protein gene and risk of dementia", Neurobiology of Aging, 28: 1361-1366 (2007).
Xiao et al., "Lysyl Oxidase, Extracellular Matrix Remodeling and Cancer Metastasis", Cancer Microenvironment, 5: 261-273 (2012).
Langdahl, Bente L., et al., "Osteoporotic Fractures are Associated with an 86-Base Pair Repeat Polymorphism in the Interleukin-1-Receptor Antagonist Gene But Not with Polymorphisms in the Interleukin-1β Gene" J. Bone Mineral Res., 15(3):402-414 (2000).
Lucentini, Jack, "Gene Association Studies Typically Wrong" The Scientist 18(24):20 (2004).
Wall, Jeffrey D., et al., "Haplotype blocks and linkage disequilibrium in the human genome" Nat. Rev. Genet. 418):587-97 (2003).
Bertram, Lars, et al., "Genome-wide association analysis reveals putative Alzheimer's disease susceptibility loci in addition to APOE" Am. J. Hum. Genet., 83(5):623-32 (2008).
Yates et al., "Dysfunction of the mTOR pathway is a risk factor for Alzheimer's disease", Acta Neuropathologica Communications, 1: 3 (2013).
Yates et al., "Role of the Proliferation-Related Molecules in the Pathogenesis of Alzheimer's Disease", A Thesis submitted to the University of Birmingham for the degree of Master of Philosophy, pp. 1-332, Apr. 2012.
Zemke et al., "The mTOR Pathway as a Potential Target for the Development of Therapies Against Neurological Disease", Drug News Perspect, 20(8): 495-499 (2007).
Genolet et al., "An approach to analyse the specific impact of rapamycin on mRNA-ribosome association", BMC Medical Genomics, 1: 33 (2008).
Search Report, dated Aug. 1, 2016, issued in corresponding European Patent Application No. 13 740 046.1.
International Search Report/Written Opinion, dated Jan. 15, 2014, issued in corresponding PCT/GB2013/051843.
Biesecker, Leslie G. et al., "The ClinSeq Project: Piloting large-scale genome sequencing for research in genomic medicine", Genome Research, 19(9): 1665-1674 (2009).
Connelly, Jessica J. et al., "Genetic and functional association of FAM5C with myocardial infarction", BMC Medical Genetics, 9: 33 (2008).
European Examination Report, dated May 3, 2017, issued in corresponding European Patent Application No. 13740046.1.
Morita, Akihiko, et al., "Association Study Between C-Reactive Protein Genes and Ischemic Stroke in Japanese Subjects" Amer. J. Hypertension 19(6):593-600 (2006).
Hirschhorn, Joel N., et al., "A Comprehensive Review of Genetic Association Studies" Genet. Med., 4(2):45-61 (2002).
Bettens, et al., "Both common variations and rare non-synonymous substitutions and small insertion/deletions in CLU are associated with increased Alzheimer risk" Mol. Neurodegener. (2012) 7:3.
Harold, et al., "Genome-wide association study identifies variants at CLU and PICALM associated with Alzheimer's disease" Nat Genet. (2009) 41(10):1088-93.

A

B

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
tcagctgtgg ggtcctgt                                                   18

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2 gaagggaca ggcagtgag                                                   19

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
gatggcgact gtcgaacc                                                   18

<210> SEQ ID NO 4
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 4
tgggttagca acctcctgat                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
gtgtagcgca cactttctgg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tgggttagca acctcctgat                                               20

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
ccgtgacctc aagccttc                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
gccaggccaa agtcacag                                                 18

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
gcgaaggaca gtggagaagt                                               20

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
```

-continued gagagggcgg atggagata                                              19

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
ttgtgccgcg taagacagt                                              19

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
cagcgtcagt gtcaggaagt                                             20

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
tgcccaagat ctgatacaag g                                           21

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ctccaacaca ccaccgtaca                                             20

<210> SEQ ID NO 15
<211> LENGTH: 19
<212> TYPE: DNA
<213> ORGANISM: Artificial Sequence
<220> FEATURE:
<223> OTHER INFORMATION: Synthetic primer

<400> SEQUENCE: 15
ctcctggttc tgcccaagt                                              19

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
caggttctct aggggcttcc                                             20

THERAPEUTIC TARGETS FOR ALZHEIMER'S DISEASE

CROSS-REFERENCE TO RELATED APPLICATIONS

This application is a divisional of U.S. patent application Ser. No. 14/413,659, filed Jan. 8, 2015, which is a § 371 of International Application No. PCT/GB2013/051843, filed Jul. 11, 2013, which claims priority from GB 1212334.5, filed Jul. 11, 2012. The entire disclosure of each of the aforesaid applications is incorporated by reference in the present application.

FIELD OF THE INVENTION

The present invention relates to novel strategies for the prevention, treatment and diagnosis of Alzheimer's disease. In addition, the invention relates to strategies for assessing an individual's susceptibility or pre-disposition to Alzheimer's disease. In particular, the present invention relates to methods involving the use of therapeutic targets and diagnostic and/or predictive markers within the mTOR signalling pathway.

BACKGROUND TO THE INVENTION

Alzheimer's disease is the most common form of dementia in older people. As a result of population aging worldwide, the prevalence of this disease is set to increase significantly in coming years. As such, there is an urgent need to develop better prognostic and diagnostic tools and new treatments for people identified as having this disease.

Alzheimer's disease is a chronic neurodegenerative disorder characterised by selective loss of cortical neurons within the hippocampus and the temporal and frontal lobes of the brain. The neurodegenerative process occurring in Alzheimer's disease is accompanied by progressive cognitive impairment leading ultimately to dementia in affected individuals.

There is currently no accepted "gold standard" diagnostic test for Alzheimer's disease in the live patient. This reflects the difficulties associated with identifying patients who would go on to be classified as having this disease at post mortem examination. Clinical diagnosis of Alzheimer's disease is typically based on evaluation of clinical criteria, such as the NINCDS/ADRDA criteria (McKhann, G. et al., (1984) Neurology 34: 939-944).

The problem with the diagnostic methods used to date lies in the fact that patients are typically diagnosed once clinical dementia has started to develop. It follows therefore, that existing treatment strategies are limited to agents used primarily to manage the symptoms of disease. For example, cholinesterase inhibitors are administered to patients so as to block the degradation of the neurotransmitter acetylcholine and thereby enhance neurotransmission in the brain. Use of such agents can help to preserve cognitive function, but does not improve the underlying pathology and is therefore not a curative approach.

Although the etiology of Alzheimer's disease is poorly understood, the neuropathology associated with the development of this disease has been relatively well characterised. The classical hallmarks of this disease consist of amyloid-β plaques, which accumulate in the brain, and neurofibrillary tangles (NFT) consisting of hyperphosphorylated tau protein present in affected neurons. Additional changes occurring at the cellular level, which are now thought to precede the deposition of plaques and NFTs, include damage to cells caused by oxidative stress, mitochondrial malfunction and aberrant re-entry of neurons into the cell division cycle.

In addition to difficulties associated with diagnosing Alzheimer's disease, there are also problems associated with identifying individuals in the population who are at increased and/or decreased risk of developing Alzheimer's disease during their lifetime, as compared with the average level of risk associated with the general population. The only known genetic risk factor for late onset sporadic form of Alzheimer's disease is the polymorphism on the ApoE gene. Other discovered polymorphisms appear to be restricted to relatively small patient subgroups. Thus risk prediction or assessment of susceptibility, before the development of clinical Alzheimer's disease, is difficult as well.

There is now good evidence to suggest that the neuropathology underlying Alzheimer's disease begins years, maybe even a decade, prior to the diagnosis of clinical dementia (Forlenza et al., (2010) BMC Medicine 8:89). Based on these observations, the continuum of Alzheimer's disease progression has been classified into three phases:

(i) asymptomatic Alzheimer's disease (preclinical stage);
(ii) mild cognitive impairment (MCI) due to Alzheimer's disease (pre-dementia stage); and
(iii) clinically-defined Alzheimer's disease (dementia).

In light of the above, there now exist several opportunities for improved management of Alzheimer's disease. In particular, it may be possible to identify individuals at increased risk of developing Alzheimer's disease, and/or diagnose individuals at a much earlier stage of disease, for example, individuals with asymptomatic disease or those patients with MCI that will go on to develop clinically-defined Alzheimer's disease. If susceptible individuals can be identified and/or diagnosed at an earlier stage of disease, it will be possible to develop, test and use new preventative and/or curative treatments intended to stabilize and/or reverse the neurodegenerative process and thereby prevent cognitive decline.

Researchers are already using the improved knowledge of Alzheimer's disease pathogenesis to develop more effective methods of diagnosis and treatment. In this regard, diagnostic biomarkers have been identified that can be measured in humoral fluids, mainly cerebrospinal fluids, and biomarkers that may be detected using advanced neuroimaging methods (Gustaw-Rothenberg et al., (2010) Biomark. Med. 4(1):15-26).

Furthermore, new "disease-modifying" treatments are being developed that tackle the deposition of β-amyloid plaques and NFTs (Bonda et al., (2010) Curr. Opin. Drug Discov Devel. 13(2): 235-246)

There remains however, an ongoing need to improve methods for the diagnosis and treatment of Alzheimer's disease, particularly early-stages of disease. The present invention seeks to address these issues.

SUMMARY OF INVENTION

The present invention is directed towards new methods of preventing, treating and diagnosing Alzheimer's disease based on the use of novel gene targets linked to this disease. The invention also relates to screening methods for identifying individuals that are pre-disposed to Alzheimer's disease, based on the use of novel gene targets.

The gene targets presented herein are classified as "rapamycin-sensitive" genes for the reason that their cellular expression is affected by the compound rapamycin. The group of rapamycin-sensitive genes to which the present invention relates were found to be deregulated in the brains of patients diagnosed with Alzheimer's disease, as compared with control samples, using microarray expression analysis. Rapamycin is known to inhibit the serine/threonine kinase mTOR and thereby reduce signalling downstream of this protein therefore the present invention is directed in particular, to the use of novel therapeutic and diagnostic targets within the mTOR signalling pathway in the context of methods for the prevention, treatment and diagnosis of Alzheimer's disease.

In a first aspect, the present invention provides a method for the prevention and/or treatment of Alzheimer's disease in a subject, comprising administering to the subject a pharmacological agent which modulates one or more targets within the mTOR signalling pathway of a cell, wherein the target is selected from:—
(i) the rapamycin-sensitive genes shown in Tables 2, 3, 4 and 5;
(ii) the transcriptional products of the rapamycin-sensitive genes shown in Tables 2, 3, 4 and 5, or fragments thereof; and
(iii) the proteins encoded by the rapamycin-sensitive genes shown in Tables 2, 3, 4 and 5, or fragments thereof.

In a second aspect, the invention provides a method of screening for pharmacological agents useful in the prevention and/or treatment of Alzheimer's disease in a subject, wherein said method comprises:—
(i) contacting a cell with a test pharmacological agent;
(ii) measuring either the expression level of one or more of the rapamycin-sensitive genes shown in Tables 2, 3, 4 and 5, or the level or activity of one or more of the proteins encoded by the rapamycin-sensitive genes shown in Tables 2, 3, 4 and 5;
(iii) measuring either the expression level of one or more of the rapamycin-sensitive genes shown in Tables 2, 3, 4 and 5, or the level or activity of one or more of the proteins encoded by the rapamycin-sensitive genes shown in Tables 2, 3, 4 and 5 in a control cell not exposed to the test pharmacological agent;
(iv) comparing the results determined in steps (ii) and (iii)
wherein a difference in the expression level of one or more of the rapamycin-sensitive genes shown in Tables 2, 3, 4 and 5, or the level or activity of one or more of the proteins encoded by the rapamycin-sensitive genes shown in Tables 2, 3, 4 and 5, indicates that the test pharmacological agent is suitable for use in the prevention and/or treatment of Alzheimer's disease.

In a third aspect, the invention provides a method to assist with diagnosis of Alzheimer's disease in a live human subject, which method comprises the steps of:—
(i) measuring either the expression level of one or more of the rapamycin-sensitive genes shown in Tables 2, 3, 4 and 5, and/or the activity of one or more of the proteins encoded by the rapamycin-sensitive genes shown in Tables 2, 3, 4 and 5;
(ii) comparing the expression level and/or activity measured in (i) with reference/control values,
wherein a difference in expression level of one or more of the rapamycin-sensitive genes shown in Tables 2, 3, 4 and 5, and/or the level or activity of one or more of the proteins encoded by the rapamycin-sensitive genes shown in Tables 2, 3, 4 and 5 is indicative of Alzheimer's disease.

In a fourth aspect, the invention provides a method of assessing the risk of Alzheimer's disease progression in a human subject, which method comprises the steps of:—
(i) measuring either the expression level of one or more of the rapamycin-sensitive genes shown in Tables 2, 3, 4 and 5, and/or the activity of one or more of the proteins encoded by the rapamycin-sensitive genes shown in Tables 2, 3, 4 and 5;
(ii) comparing the expression level and/or activity measured in (i) with reference/control values,
wherein a difference in expression level and/or activity of the one or more rapamycin sensitive genes shown in Tables 2, 3, 4 and 5 is indicative of Alzheimer's disease progression.

In a fifth aspect, the invention provides a method for screening a human subject for pre-disposition to Alzheimer's disease, which method comprises the steps of:—
(i) measuring either the expression level of one or more of the rapamycin-sensitive genes shown in Tables 2, 3, 4 and 5, and/or the activity of one or more of the proteins encoded by the rapamycin-sensitive genes shown in Tables 2, 3, 4 and 5;
(ii) comparing the expression level and/or activity measured in (i) with reference/control values,
wherein a difference in expression level and/or activity of the one or more rapamycin sensitive genes shown in Tables 2, 3, 4 and 5 is taken to mean the subject is pre-disposed to Alzheimer's disease.

In all aspects of the invention described above, in preferred embodiments, the one or more targets within the mTOR signalling pathway is/are selected from the group of rapamycin-sensitive genes consisting of calcium channel, voltage-dependent, L type, alpha 1D subunit (CACNA1D), gamma-aminobutyric acid B receptor, 2 (GABBR2), homeobox D10 (HOXD10), Kruppel-like factor 2 (KLF2), rhodopsin (RHO) and GLI zinc finger family 2 (GLI2).

The present invention is also directed to methods for identifying human subjects that are pre-disposed to Alzheimer's disease, and methods to assist with diagnosis of Alzheimer's disease in live human subjects based on the use of polymorphisms, particularly single nucleotide polymorphisms (SNPs), in the rapamycin-sensitive genes described herein. Methods are also described based on the use of polymorphisms within genes which affect the expression of rapamycin-sensitive genes.

Therefore, in a sixth aspect, the invention provides a method of screening a human subject for pre-disposition to Alzheimer's disease, which method comprises genotyping the subject for one or more polymorphisms in one or more of the rapamycin-sensitive genes shown in Table 1, wherein the presence of at least one variant allele associated with Alzheimer's disease is an indication that the subject is pre-disposed to Alzheimer's disease.

In a seventh aspect, the invention provides a method of screening a human subject for pre-disposition to Alzheimer's disease, which method comprises genotyping the subject for one or more polymorphisms in one or more genes which affect the expression of one or more of the rapamycin-sensitive genes shown in Table 1, wherein the presence of at least one variant allele associated with Alzheimer's disease is an indication that the subject is pre-disposed to Alzheimer's disease.

In an eighth aspect, the invention provides a method to assist with diagnosis of Alzheimer's disease in a live human subject, which method comprises genotyping the subject for one or more polymorphisms in one or more of the rapamycin-sensitive genes shown in Table 1, or a polymorphism in one or more genes which affect the expression of one or more of the rapamycin-sensitive genes shown in Table 1, wherein the presence of at least one variant allele associated with Alzheimer's disease is indicative of Alzheimer's disease.

In a ninth aspect, the invention provides an array or kit for detecting genetic polymorphisms in a sample taken from a subject wherein the array or kit comprises reagents for the detection of one or more polymorphisms in one or more of the rapamycin-sensitive genes shown in Table 1, or one or more polymorphisms in one or more genes which affect the expression of one or more of the rapamycin-sensitive genes shown in Table 1.

The present invention is also concerned with polymorphisms that may be used to monitor the mTOR signalling pathway in a cell. These polymorphisms are associated with the differential sensitivity of cells to the G1/S inhibitor rapamycin.

Therefore, in a further aspect, the invention provides a method by which to monitor mTOR signalling in a human cell, which method comprises detecting one or more polymorphisms in one or more of the rapamycin-sensitive genes shown in Table 1, or one or more polymorphisms in one or more genes which affect the expression of one or more of the rapamycin-sensitive genes shown in Table 1, wherein the presence of at least one variant allele associated with a differential response to rapamycin is indicative of the status of mTOR signalling in the cell.

In all aspects of the invention relating to polymorphisms described above, in preferred embodiments, the one or more, two or more, three or more, four or more, five or more, six or more, seven or more, eight or more, nine or more, ten or more polymorphisms for the purposes of genotyping or detection are in one or more of the rapamycin-sensitive genes selected from LILRB2, FAM5C, CRP, CLU, FCGR2A, CD1E, FAM5C, LPL, SYK and CUX1 and/or in one or more of the genes which affect the expression of one or more rapamycin-sensitive genes, selected from POU2F1, ADRA1A, PRDM1 and LOXL2.

In further preferred embodiments, the one or more, two or more, three or more, four or more, five or more, six or more, seven or more, eight or more, nine or more, ten or more polymorphisms is/are selected from the group consisting of:
  (i) the single polynucleotide polymorphisms: rs798893, rs725106, rs1341665, rs1359059, rs1532278, rs1801274, rs2036108, rs811925, rs883524, rs1065457, rs1148613, rs295, rs290258, rs365836 and rs569214; and
  (ii) any polymorphism in linkage disequilibrium with the single nucleotide polymorphisms of (i).

DETAILED DESCRIPTION

Figure 1:
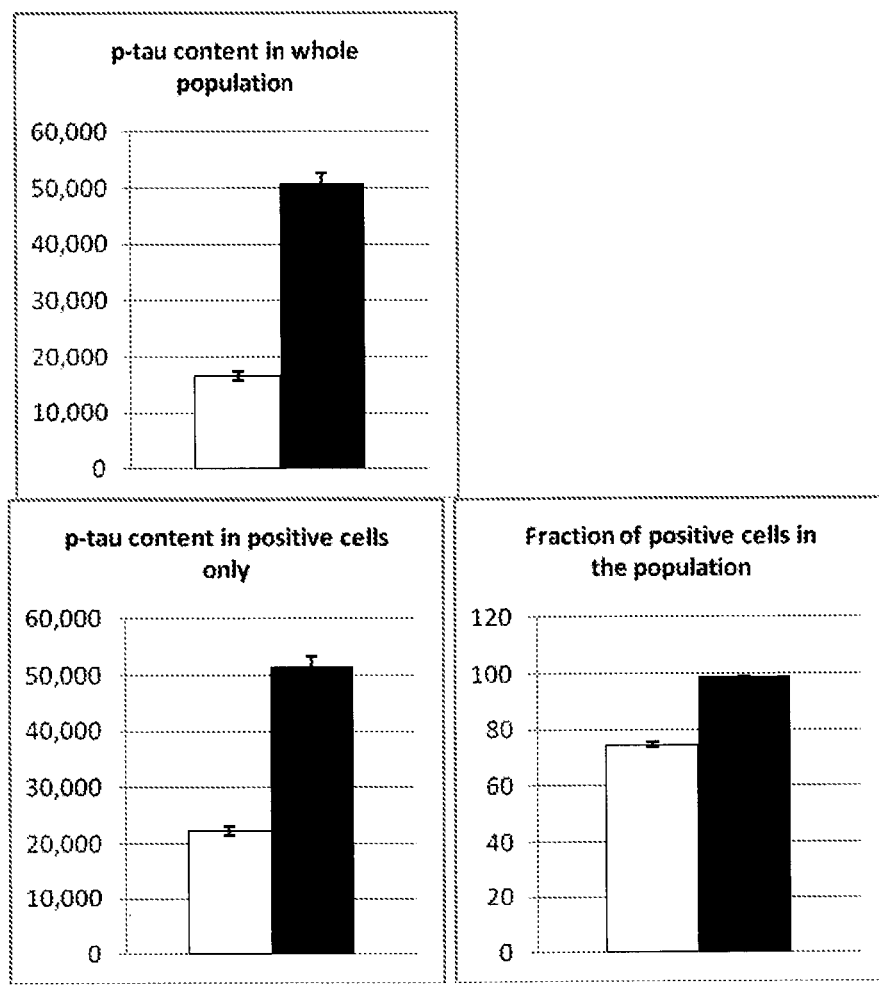
FIG. 1 Cell cycle dependent expression of phosphor-tau (p-tau) in SH-SY5Y neuroblastoma cells. White bars=G1; Black bars=G2.

The present invention is directed to methods for preventing, treating and/or diagnosing Alzheimer's disease in live human subjects involving use of gene targets within the "mTOR signalling pathway".

The kinase, "mTOR", functions within the context of two cytoplasmic protein complexes known as mTORC1 and mTORC2. It is however, only the mTORC1 complex that is sensitive to the inhibitor rapamycin. Thus, the targets of interest in the present invention may also be classified as targets within the mTORC1 signalling pathway.

The cytoplasmic kinase mTOR is stimulated or activated by a wide variety of upstream signals. These include signals generated or triggered as a result of nutrient sensing, hypoxia, and/or the activity of growth factors and their cognate receptors. Activation of mTOR upregulates its kinase activity and thereby increases mTOR-mediated phosphorylation of downstream protein targets within the cell. In most cases, the direct downstream protein targets of mTOR interact with a variety of further molecular targets, and in doing so, stimulate a wide variety of cellular responses, such as increased protein synthesis and the promotion of cell growth and proliferation. The chain of molecular events triggered downstream of mTOR-mediated phosphorylation of its direct protein targets is defined herein as the "mTOR signalling pathway", and the target genes/proteins of the present invention fall within this pathway.

In the methods of the present invention, the particular targets of interest within the mTOR signalling pathway are selected from the genes shown in Tables 2, 3, 4 and 5. The term "target" is intended to encompass the genes of Tables 2, 3, 4 and 5, the transcriptional products of such genes and the proteins encoded by such genes.

The particular genes shown in Table 1 are "rapamycin-sensitive" for the reason that their cellular expression is affected (increased or decreased) by the compound rapamycin. Since rapamycin is known to inhibit the serine/threonine kinase mTOR in (human) cells, and thereby reduce signalling downstream of this protein, the genes shown in Tables 2, 3, 4 and 5 are grouped herein as targets within the mTOR signalling pathway. Tables 2 and 4 show the rapamycin-sensitive genes that have an altered expression in the brain of Alzheimer's patients with mild disease and Tables 3 and 5 show the rapamycin-sensitive genes that have an altered expression in the brain of Alzheimer's patients with advanced disease.

Therapeutic Methods

In a first aspect, the present invention provides methods for the prevention and/or treatment of live human subjects diagnosed with Alzheimer's disease involving administration of pharmacological agents which modulate or are capable of modulating one or more, two or more, three or more, four or more etc. targets within the mTOR signalling pathway.

In certain embodiments, the therapeutic target is selected from the rapamycin-sensitive genes shown in Tables 2, 3, 4 and 5 and the pharmacological agent will typically modulate the target via effects at the level of gene expression. In preferred embodiments, the one or more targets within the mTOR signalling pathway is/are selected from the group of rapamycin-sensitive genes consisting of calcium channel, voltage-dependent, L type, alpha 1D subunit (CACNA1D), gamma-aminobutyric acid B receptor, 2 (GABBR2), homeobox D10 (HOXD10), Kruppel-like factor 2 (KLF2), rhodopsin (RHO) and GLI zinc finger family 2 (GL12).

In certain embodiments, the pharmacological agent may act by up-regulating/increasing or down-regulating/decreasing expression of the target gene. Gene expression may be detected at the level of the transcriptional product or at the level of the protein produced, using standard techniques described herein below. Up-regulation or down-regulation of gene expression is measured relative to the situation in the absence of pharmacological agent, or in the presence of an appropriate, inactive control.

In certain embodiments of the invention, the term "target" may be used to refer to the transcriptional products of the rapamycin-sensitive genes shown in Tables 2, 3, 4 and 5, or fragments thereof. The term "transcriptional product" is intended to encompass the pre-mRNA species generated following transcription of the gene, any of the splice intermediates generated during pre-mRNA processing and the mature fully-spliced mRNA species. Inhibition of such transcriptional products may involve down-regulating the level of such products, for example, by promoting nucleic acid degradation. This may be mediated for example, by interfering RNA species, such as siRNAs.

In certain other embodiments of the invention, the "target" may refer to the proteins encoded by the rapamycin-sensitive genes shown in Tables 2, 3, 4 and 5, or fragments thereof. The pharmacological agent may therefore bring about an increase or decrease in the level of protein within a cell or an increase or decrease in the biological activity of the protein.

As noted above, the target of the invention may include a fragment of the transcriptional product of the rapamycin-sensitive genes shown in Tables 2, 3, 4 and 5 or a fragment of a protein encoded by one or more of the rapamycin-sensitive genes shown in Tables 2, 3, 4 and 5. The term "fragment" should be taken to mean a form of the transcriptional product or protein, which is reduced in length by one or more, two or more, three or more, four or more etc. nucleotides or amino acids, respectively, as compared with the full-length transcriptional product or protein. In relation to post-transcriptional products, the term "fragment" may also be applied to alternatively-spliced forms of mRNA produced from the originating pre-mRNA transcript.

In the context of the present invention, the term "modulates" is used very broadly to mean an agent capable of changing or altering the expression of a gene, the production and/or level of a transcriptional product of a gene and/or the production, level and/or activity of a protein encoded by a gene. The term "modulates" may be used to describe an increase or a decrease in any of the parameters described above. Any increase or decrease is measured relative to the situation present in the absence of the pharmacological agent or in the presence of a suitable inactive control.

In one embodiment, the pharmacological agent is an activator or agonist capable of increasing or up-regulating the expression of a gene, the production and/or level of a transcriptional product of a gene and/or the production, level and/or activity of a protein encoded by a gene. In an alternative embodiment, the pharmacological agent is an inhibitor or antagonist capable of decreasing or down-regulating the expression of a gene, the production and/or level of a transcriptional product of a gene and/or the production, level and/or activity of a protein encoded by a gene.

Classes of pharmacological agents suitable for use in accordance with the methods described herein would be available to those skilled in the art. Such agents include but are not limited to small molecules, organic or inorganic molecules, biological molecules including antibodies and antigen binding fragments thereof, natural or synthetic polypeptides or peptides, nucleic acid therapeutic agents including antisense RNA species and double-stranded RNA species for use as RNA interfering agents, for example siRNA molecules.

In the context of the present invention, the term antibody covers native immunoglobulins from any species, chimeric antibodies, humanised antibodies, F(ab')2 fragments, Fab fragments, Fv fragments, sFv fragments and highly related molecules such as those based upon antibody domains which retain specific binding affinity (for example, single domain antibodies).

Pharmacological agents may be formulated as compositions for delivery wherein the agent in a suitable dosage form is combined with a pharmaceutically acceptable carrier such as a diluent, filler, salt, buffer, stabilizer, solubilizer etc. The dosage form may contain other pharmaceutically acceptable excipients for modifying conditions such as pH, osmolarity, taste, viscosity, sterility, lipophilicity, solubility etc.

Suitable dosage forms include solid dosage forms, for example, tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Suitable diluents and solvents include sterile water, Ringer's solution and isotonic sodium chloride solution, etc. Liquid dosage forms also include solutions or sprays for intranasal administration.

Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally this will be within the range 0.1 mg to 1000 mg.

Wherein the pharmacological agent consists of a nucleic acid therapeutic agent, for example, an antisense RNA species or a double-stranded RNA species for use as an RNA interfering agent, the active agent may be administered to a patient in need thereof via gene therapy approaches.

The rapamycin-sensitive target genes shown in Tables 2, 3, 4 and 5 encode a range of proteins including enzymes, receptors and transporters. Preferred known pharmacological agents for use in conjunction with the present methods include the following; however, this is not to be construed as limiting the invention to these specific embodiments.

Wherein the target gene is CACNA1D, pharmacological agents for use may include MEM-1003, clevidipine butyrate, aliskiren/amlodipine/hydrochlorothiazide, mibefradil, bepridil, nisoldipine, isradipine, amlodipine and/or nicardipine.

Wherein the target gene is HDAC5, pharmacological agents for use may include tributyrin, belinostat, pyroxamide, vorinostat and/or romidepsin.

Wherein the target gene is IL6, pharmacological agents for use may include tocilizumab.

Wherein the target gene is NR3C1, pharmacological agents for use may include rimexolone, medrysone, clocortolone pivalate, diflorasone diacetate, fluorometholone, dexamethasone phosphate, cortisone acetate, halcinonide, flurandrenolide, desoximetasone, desonide, prednisolone, clobetasol propionate, fluocinolone acetonide, prednisone, hydrocortisone, triamcinolone, dexamethasone 21-acetate, 11 beta hydrocortisone acetate, betamethasone, dexamethasone, budesonide, fluticasone, beclomethasone dipropionate, acetic acid/hydrocortisone, betamethasone acetate/ betamethasone phosphate, betamethasone acetate, triamcinolone acetonide, ciprofloxacin/hydrocortisone, dexamethasone/neomycin/polymyxin B, ciprofloxacin/dexamethasone, ORG 34517, ciclesonide, betamethasone dipropionate/calcipotriene, fluticasone furoate, budesonide/ formoterol, difluprednate, formoterol/mometasone furoate, clotrimazole/betamethasone dipropionate, fluticasone/salmeterol, dexamethasone/tobramycin, clotrimazole/betamethasone, miconazole, prednisolone acetate, clioquinol/hydrocortisone, methylprednisolone acetate, mometasone furoate, amcinonide, methylprednisolone succinate, betamethasone phosphate, fluocinonide, prednicarbate, hydrocortisone cypionate, hydrocortisone succinate, prednisolone phosphate, betamethasone valerate, betamethasone benzoate, fludrocortisone acetate, prednisolone tebutate, betamethasone dipropionate, hydrocortisone buteprate, alclometasone dipropionate, hydrocortisone butyrate, fluorometholone acetate, hydrocortisone valerate, nystatin/triamcinolone acetonide, loteprednol etabonate, hydrocortisone phosphate, methylprednisolone, halobetasol propionate, flunisolide and/or mifepristone.

Wherein the target gene is NTSR1, pharmacological agents for use may include contulakin-G.

Wherein the target gene is PRKCH, pharmacological agents for use may include ingenol 3-angelate.

Wherein the target gene is SCN8A, pharmacological agents for use may include riluzole.

Wherein the target gene is SERPINE1, pharmacological agents for use may include drotrecogin alfa.

Wherein the target gene is TRPV1, pharmacological agents for use may include SB-705498, resiniferatoxin and/or capsaicin.

Wherein the target gene is VEGFA, pharmacological agents for use may include bevacizumab, ranibizumab, aflibercept and/or pegaptanib.

Wherein the target gene is GLP1R, pharmacological agents for use may include liraglutide, T-0632, GLP-1 (7-36) amide and/or exenatide.

The term "Alzheimer's disease" is used herein broadly to mean disease diagnosed on the basis of clinical criteria and/or disease identified on the basis of pathophysiological changes associated with AD.

At present, the diagnosis of Alzheimer's disease in live human subjects is based on the evaluation of clinical criteria, such as the NINCDS/ADRDA criteria (McKhann, G. et al., (1984) Neurology 34: 939-944). However, such diagnostic criteria applied in the clinic are based on the measurement of cognitive parameters, and are thus reliant on the onset of cognitive symptoms in patients with this disease.

It is however, clear from extensive research carried out that the pathophysiological or changes defining AD are detectable in individuals years before these patients show any signs of cognitive impairment. Alzheimer's disease has accordingly, been classified into three phases:
  (i) asymptomatic Alzheimer's disease (preclinical stage);
  (ii) mild cognitive impairment (MCI) due to Alzheimer's disease (pre-dementia stage); and
  (iii) clinically-defined Alzheimer's disease (dementia).

In the context of the present invention, the phrase "prevention and/or treatment of Alzheimer's disease" is intended to encompass prevention and/or treatment strategies used for an individual having disease at any one of the three phases defined above.

It is not at present possible to reliably diagnose individuals with asymptomatic AD or early-stage disease; however, as methods of diagnosis improve, it may prove possible to identify individuals with neuropathological changes defining the early stages of AD. The methods described herein may therefore be used to prevent and/or delay the onset of cognitive symptoms in a subject asymptomatic for Alzheimer's disease. This may be achieved by a reversal, stabilisation and/or delay of the neurological changes underlying AD pathology.

The methods provided herein may also be used to prevent and/or delay the onset of AD-associated dementia in individuals who are already symptomatic to varying degrees. For example, the methods of the invention may be applied to individuals classified according to standard criteria, for example the Mayo Clinic diagnostic criteria (Winblad et al., (2004) J. Intern. Med 256: 240-246), as having mild cognitive impairment (MCI). In a further embodiment, the method of the invention may be used to prevent and/or delay the worsening of symptoms in individuals already diagnosed with clinical dementia. The methods of the present invention may therefore be used to treat Alzheimer's disease in a subject exhibiting mild cognitive impairment or in a subject exhibiting clinical dementia.

The human subject to be treated according to the methods provided herein may be any human subject diagnosed as having Alzheimer's disease. This includes individuals with early-onset familial Alzheimer's disease and individuals with late-onset sporadic forms of this disease.

Screening Methods

In a second aspect, the present invention also provides methods of screening for pharmacological agents useful in the prevention and/or treatment of Alzheimer's disease in a subject, wherein said method comprises the steps of:—
  (i) contacting a cell with a test pharmacological agent;
  (ii) measuring either the expression level of one or more of the rapamycin-sensitive genes shown in Tables 2, 3, 4 and 5, or the level or activity of one or more of the proteins encoded by the rapamycin-sensitive genes shown in Tables 2, 3, 4 and 5;
  (iii) measuring either the expression level of one or more of the rapamycin-sensitive genes shown in Tables 2, 3, 4 and 5, or the level or activity of one or more of the proteins encoded by the rapamycin-sensitive genes shown in Tables 2, 3, 4 and 5 in a control cell not exposed to the test pharmacological agent;
  (iv) comparing the results determined in steps (ii) and (iii) wherein a difference in the expression level of one or more of the rapamycin-sensitive genes shown in Tables 2, 3, 4 and 5, or the level or activity of one or more of the proteins encoded by the rapamycin-sensitive genes shown in Tables 2, 3, 4 and 5, indicates that the test pharmacological agent is suitable for use in the prevention and/or treatment of Alzheimer's disease.

In preferred embodiments, the one or more targets within the mTOR signalling pathway is/are selected from the group of rapamycin-sensitive genes consisting of calcium channel, voltage-dependent, L type, alpha 1D subunit (CACNA1D), gamma-aminobutyric acid B receptor, 2 (GABBR2), homeobox D10 (HOXD10), Kruppel-like factor 2 (KLF2), rhodopsin (RHO) and GLI zinc finger family 2 (GL12).

The pharmacological agents for testing in the screening methods provided herein may be selected from any class of agent as described in the context of the therapeutic methods of the present invention. The methods may involve screening one or more pharmacological agents simultaneously, for example in a multiplex format. Agents for use in the screening methods may be provided in any suitable format, including compound libraries.

The "difference" in gene expression and/or protein activity to be detected using the screening method described herein may be established according to the sensitivity requirements of those using the method to identify pharmacological agents suitable for the prevention and/or treatment of AD.

In certain embodiments, the difference may be measured as a decrease in the expression of one or more of the rapamycin-sensitive genes shown in Tables 2, 3, 4 and 5 as compared with control cells not exposed to the pharmacological agent, wherein said decrease indicates that the test pharmacological agent is suitable for use in the prevention and/or treatment of Alzheimer's disease.

Any difference or decrease in gene expression may be measured by assessing the level of transcriptional product or mRNA produced from any of the rapamycin-sensitive genes shown in Tables 2, 3, 4 and 5. Alternatively or in addition, any difference or decrease may be measured by assessing the levels of protein produced from any of the rapamycin-sensitive genes shown in Tables 2, 3, 4 and 5.

Suitable methods for the detection/quantitation of transcriptional products which may be used in accordance with the present methods are well known in the art, and include, but are not limited to hybridisation techniques, such as Northern blotting or microarray technologies, and amplification-based techniques such as RT-PCR or nucleic-acid sequence-based amplification (NASBA).

Suitable techniques for assessing protein levels are known in the art and include, but are not limited to, flow cytometry, immunoblot analysis, ELISA, Elispot and Fluorospot assays. In certain embodiments, these assays may be used in conjunction with commercially-available antibodies that bind to the protein of interest, in order to determine protein levels. Standard assays are also available for measuring the activity of certain proteins, for example standard enzyme activity assays, such as kinase assays.

Diagnostic Methods

In a further aspect, the current invention provides a method to assist with diagnosis of Alzheimer's disease in a live human subject.

In the context of the present invention, the term "diagnosis of Alzheimer's disease" is used very broadly and should be taken to mean diagnosis of an individual having disease at any one of the three phases of the disease defined above i.e. the preclinical stage, the pre-dementia stage or the dementia stage. In one embodiment, the method of the invention is used to diagnose or assist with diagnosis of Alzheimer's disease in its preclinical stage in an individual with no symptoms of disease, for example no signs of cognitive impairment. In other embodiments, the same basic methodology may be used to screen subjects who are "symptomatic" to varying degrees. For example, the method of the invention may be applied to individuals classified according to standard criteria, for example the Mayo Clinic diagnostic criteria (Winblad et al., (2004) J. Intern. Med 256: 240-246), as having mild cognitive impairment (MCI). Not all patients classified as having MCI will have the type of underlying neurodegeneration associated with Alzheimer's disease. Thus, the present method may be used to distinguish or assist with distinguishing between individuals with MCI that have underlying Alzheimer's disease and therefore are likely to go on to develop Alzheimer's disease-associated dementia, and those that have MCI attributable to a different cause or condition. In a further embodiment of the invention, the method may be used to diagnose or assist with diagnosis of Alzheimer's disease in a human subject exhibiting one or more symptoms consistent with Alzheimer's disease.

The diagnostic methods of the present invention may also be used in conjunction with existing diagnostic criteria, for example the NINCDS/ADRDA criteria, in order to verify or substantiate an Alzheimer's disease diagnosis in a human subject who already meets the existing criteria for a positive diagnosis. In this embodiment, the present methods may provide an adjunct to alternative diagnostic tests, wherein the present methods are independent of neuropsychological symptoms. This may allow for a more reliable diagnosis of clinical Alzheimer's disease, particularly since not all patients presenting with dementia symptoms will have Alzheimer's disease as the underlying cause.

The present methods are used in particular, to assist with diagnosis of Alzheimer's disease in a live human subject. A definitive diagnosis of Alzheimer's disease is generally considered by those in the field to be impossible in a live subject, and can only be made post-mortem following pathological examination of brain tissue from the patient. Thus, although present methods may seek to "diagnose" Alzheimer's disease in live subjects, such a diagnosis is typically based on an assessment of the likelihood that any given individual has the disease. In this regard, individuals may be classified as "possible Alzheimer's disease" or "probable Alzheimer's disease" based on the results of current diagnostic tests.

The present methods may therefore be used to "assist with diagnosis" meaning that they are used to assess the likelihood that an individual has Alzheimer's disease at any one of the three phases of the disease described above. In preferred embodiments, the present method may be used to assist with diagnosis of early-stage Alzheimer's disease in asymptomatic patients or patients exhibiting mild cognitive impairment.

The methods of the invention may also be used in combination or together with other methods or tests used for Alzheimer's disease diagnosis, for example in order to improve the specificity and/or sensitivity of these methods or tests. In specific embodiments, the present methods may be carried out in combination with a test designed to monitor one or more biomarkers of Alzheimer's disease in a particular individual, and the combined result may be used to assess the likelihood that the individual has Alzheimer's disease. In alternative embodiments, the present method may be used to independently substantiate the results of other diagnostic tests.

The present method is intended to provide a means to diagnose and/or assist with diagnosis of Alzheimer's disease in multiple settings. In one embodiment, the present method may be used to diagnose individuals with Alzheimer's disease so as to identify patients suitable for the assessment of new Alzheimer's disease treatments, for example the identification of suitable subjects for clinical trials. New treatments or therapies designed to be preventive and/or curative may only have the best chance of success in patients with asymptomatic or early-stage disease. The present method may therefore be used to diagnose or assist with diagnosis of preclinical Alzheimer's disease in asymptomatic individuals or to diagnose or assist with diagnosis of individuals with MCI that have underlying Alzheimer's disease pathology, for the purposes of assessing new treatments specifically in these patients. As improved treatments for Alzheimer's disease become available, the present methods may also be used to diagnose or assist with diagnosis of individuals so as to identify patients who will benefit from treatments that may have the ability to prevent cognitive decline.

The present invention also provides methods of assessing the risk of Alzheimer's disease progression in a human subject. In this context, "Alzheimer's disease progression" should be taken to mean the progressive neurodegeneration associated with this disease and/or the progressive decline in cognitive function that accompanies the underlying neuropathology. Such methods may be applied to individuals suspected of having any one of the three phases of Alzheimer's disease defined above, or individuals considered at risk of developing this disease.

In preferred embodiments of the invention, the methods provide means by which to assess or predict cognitive decline in human subjects by identifying individuals with early-stage Alzheimer's disease who will go on to develop Alzheimer's disease-associated dementia. In certain embodiments, the individual or human subject for testing will be asymptomatic for Alzheimer's disease. In alternative embodiments, the individual or human subject for testing will exhibit mild cognitive impairment or will exhibit one or more symptoms consistent with Alzheimer's disease.

In the diagnostic methods and the methods of assessing the risk of disease progression described above, the method comprises as a first step measuring either the expression level of one or more of the rapamycin-sensitive genes shown in Tables 2, 3, 4 and 5 and/or the activity of one or more of the proteins encoded by the rapamycin-sensitive genes shown in Tables 2, 3, 4 and 5. Gene expression may be analysed by assessing levels of mRNA produced following gene transcription or by assessing levels of the protein produced following translation of the mRNA. The detection of mRNA and protein levels may be carried out by methods known to those skilled in the art. Protein activity may also be analysed using suitable assays known to those skilled in the art.

In certain embodiments of the invention, protein activity may be measured directly. For example, the activity of a kinase enzyme may be measured using an assay that detects phosphorylation of the enzyme's direct substrate. Protein activity may also be measured indirectly by measuring alterations and/or changes in the level and/or activity of metabolites linked to the activity of the proteins encoded by the rapamycin-sensitive genes shown in Tables 2, 3, 4 and 5.

As a second step, the methods require a comparison between the gene expression levels and/or protein activity measured in the first step and the gene expression levels and/or protein activity defined as reference or control values. Such reference or control values may be determined from measurements made using age-matched healthy subjects, preferably wherein such subjects exhibit no signs of cognitive impairment. If the method is carried out with the intention of assessing the risk of Alzheimer's disease progression, the reference or control values may consist of values determined from measurements made using the same human subject at an earlier point in time, for example 1, 2, 3, 4, 5, 6, 7, 8, 9, 10 or 11 months earlier, or 1, 2, 3, 4, 5, 6, 7, 8, 9, 10 etc years earlier. A comparison between measurements determined for the same human subject at different points in time may assist in determining whether there has been a change in the level of expression of a gene and/or activity of a protein over time that is indicative of Alzheimer's disease progression.

The genes and/or proteins for use in conjunction with the diagnostic methods of the present invention are selected from the rapamycin-sensitive genes shown in Tables 2, 3, 4 and 5. In preferred embodiments, the one or more targets within the mTOR signalling pathway is/are selected from the group of rapamycin-sensitive genes consisting of calcium channel, voltage-dependent, L type, alpha 1D subunit (CACNA1D), gamma-aminobutyric acid B receptor, 2 (GABBR2), homeobox D10 (HOXD10), Kruppel-like factor 2 (KLF2), rhodopsin (RHO) and GLI zinc finger family 2 (GL12).

The measurement of gene expression and/or protein activity may be made using any suitable sample taken from the subject. In a preferred embodiment, the sample is derived from the cerebrospinal fluid of a patient. In certain embodiments, the level or gene expression and/or protein activity may be determined using imaging techniques, preferably non-invasive imaging of the subject's brain or regions thereof. In certain embodiments, imaging techniques may be used to detect alterations and/or temporal changes in brain metabolites, such as choline or creatine, that are indicative of a change in protein activity. Imaging techniques that may be particularly useful in conjunction with the present methods include but are not limited to PET, SPECT, MR spectroscopy and functional MRI.

Methods of Assessing Pre-Disposition to Alzheimer's Disease

In a further aspect, the current invention also provides methods for screening a human subject for pre-disposition to Alzheimer's disease, wherein said method comprises the steps of:—
  (i) measuring either the expression level of one or more of the rapamycin-sensitive genes shown in Tables 2, 3, 4 and 5, and/or the activity of one or more of the proteins encoded by the rapamycin-sensitive genes shown in Tables 2, 3, 4 and 5;
  (ii) comparing the expression level and/or activity measured in (i) with reference/control values,
  wherein a difference in expression level and/or activity of the one or more rapamycin sensitive genes shown in Tables 2, 3, 4 and 5 is taken to mean the subject is pre-disposed to Alzheimer's disease.

In certain embodiments of the invention, the difference may be measured as an increase in the expression level of one or more of the rapamycin-sensitive genes shown in Tables 2, 3, 4 and 5, and/or the activity of one or more of the proteins encoded by the rapamycin-sensitive genes shown in Tables 2, 3, 4 and 5 as compared with reference/control values and such increase is taken to mean the subject is pre-disposed to Alzheimer's disease. Such "pre-disposition to Alzheimer's disease" may be manifest as an increased lifetime risk of developing Alzheimer's disease as compared with the average lifetime risk associated with the general population, and/or as an earlier age of onset of Alzheimer's disease in affected individuals.

As described above in connection with the diagnostic methods aspect of the invention, the presently-claimed methods comprise as a first step measuring either the expression level of one or more of the rapamycin-sensitive genes shown in Tables 2, 3, 4 and 5 and/or the activity of one or more of the proteins encoded by the rapamycin-sensitive genes shown in Tables 2, 3, 4 and 5. Gene expression may be analysed by assessing levels of mRNA produced following gene transcription or by assessing levels of the protein produced following translation of the mRNA. The detection of mRNA and protein levels may be carried out by methods known to those skilled in the art. Protein activity may also be analysed using suitable assays known to those skilled in the art.

In certain embodiments of the invention, protein activity may be measured directly. For example, the activity of a kinase enzyme may be measured using an assay that detects phosphorylation of the enzyme's direct substrate. Protein activity may also be measured indirectly by measuring alterations and/or changes in the level and/or activity of metabolites linked to the activity of the proteins encoded by the rapamycin-sensitive genes shown in Tables 2, 3, 4 and 5.

As a second step, the methods require a comparison between the gene expression levels and/or protein activity measured in the first step and the gene expression levels and/or protein activity defined as reference or control values. Such reference or control values may be determined from measurements made using age-matched healthy subjects, preferably wherein such subjects exhibit no signs of cognitive impairment. Alternatively or in addition, such reference or control values may be determined from measurements made using subjects that are known not to have developed Alzheimer's disease during their lifetime.

The screening methods described herein will typically be used to assess the pre-disposition to Alzheimer's disease in individuals that are otherwise asymptomatic for this disease. Methods of Assessing Pre-Disposition to Alzheimer's Disease Based on Detection of Polymorphisms In a further aspect, provided herein is a method of screening a human subject for pre-disposition to Alzheimer's disease, which method comprises genotyping the subject for a polymorphism in one or more of the rapamycin-sensitive genes shown in Table 1, wherein the presence of at least one variant allele associated with Alzheimer's disease is an indication that the subject is pre-disposed to Alzheimer's disease.

In this aspect of the invention, "a polymorphism" can be taken to mean one or more polymorphisms. Therefore, provided herein is a method of screening a human subject for pre-disposition to Alzheimer's disease, which method comprises genotyping the subject for one or more polymorphisms in one or more of the rapamycin-sensitive genes shown in Table 1, wherein the presence of at least one variant allele associated with Alzheimer's disease is an indication that the subject is pre-disposed to Alzheimer's disease.

In a still further aspect, provided herein is a method of screening a human subject for pre-disposition to Alzheimer's disease, which method comprises genotyping the subject for one or more polymorphisms in one or more genes which affect the expression of one or more of the rapamycin-sensitive genes shown in Table 1, wherein the presence of at least one variant allele associated with Alzheimer's disease is an indication that the subject is pre-disposed to Alzheimer's disease.

As used herein, the term "polymorphism" includes single nucleotide polymorphisms or SNPs, which are changes in which a single base in the DNA differs from the usual base at that position. Millions of SNPs have been catalogued throughout the human genome, and many of these have been linked to increased or decreased susceptibility or pre-disposition to certain diseases. SNPs found within the ApoE gene have already been linked to elevated risk of Alzheimer's disease.

Associations between polymorphisms or polymorphic variants and susceptibility to Alzheimer's disease can be identified or confirmed by carrying out genetic association studies, for example family-based or case-control association studies. Associations may also be determined by evaluating the relationship between deregulated gene expression seen in the brain of Alzheimer's disease patients and the underlying genotype.

In the present methods for screening for pre-disposition to Alzheimer's disease, a subject is genotyped for one or more polymorphisms or polymorphic variants in one or more of the rapamycin-sensitive genes shown in Table 1. In certain embodiments, the subject may be genotyped for two or more, three or more, four or more, five or more, six or more, seven or more, eight or more, nine or more, ten or more polymorphisms or polymorphic variants in one or more of the rapamycin-sensitive genes shown in Table 1. Wherein the methods involve genotyping for more than one polymorphism, the polymorphisms may be in the same rapamycin-sensitive gene or in different rapamycin-sensitive genes.

Alternatively, or in addition, the subject may be genotyped for one or more, two or more, three or more, four or more, five or more, six or more, seven or more, eight or more, nine or more, ten or more polymorphisms or polymorphic variants in one or more genes which affect the expression of one or more of the rapamycin-sensitive genes shown in Table 1. Wherein the methods involve genotyping for more than one polymorphism, the polymorphisms may be in the same gene or in different genes. Polymorphisms or polymorphic variants in genes which affect the expression of rapamycin-sensitive genes may be located in genes encoding regulators, particularly upstream regulators, of expression of genes in the mTOR signalling pathway described herein.

In the context of the present invention, a polymorphism "in" a gene should be taken to mean a genetic variant present at any position within the full-length native gene. Polymorphisms may therefore be located in exons, introns or in regulatory regions located upstream or downstream of the coding segment.

In preferred embodiments, the method comprises genotyping a subject for one or more polymorphisms in one or more rapamycin-sensitive genes selected from LILRB2, FAM5C, CRP, CLU, FCGR2A, CD1E, FAM5C, LPL, SYK and CUX1. Alternatively, or in addition, the method may comprise genotyping a subject for one or more polymorphisms in one or more genes which affect the expression of one or more rapamycin-sensitive genes, wherein the "regulatory" genes are selected from POU2F1, ADRA1A, PRDM1 and LOXL2.

POU2F1 is a transcriptional regulator of the mTOR genes: A2M, CRP, CSF1R, CYP2C9, ESR1, GSTM3, IL2, IL6, PRKAA2, SPP1, TLR4 from Table 1. ADRA1A is a regulator of mTOR regulated genes: CDKN1B, EGR1, FGF7, FN1, IL6, JUN, LOX, NR4A1, NR4A2 from Table 1. LOXL2 is an upstream regulator of mTOR regulated genes: CDH1, FN1, MMP9 from Table 1. PRDM1 is the upstream regulator of mTOR regulated genes: ESR1, IGHG1, IL10, IL2, IL6, MYC, RELN, SCGN from Table 1.

In preferred embodiments, the screening methods involve genotyping a subject for one or more, two or more, three or more, four or more, five or more, six or more, seven or more, eight or more, nine or more, ten or more polymorphisms selected from the group of single nucleotide polymorphisms consisting of rs798893, rs725106, rs1341665, rs1359059, rs1532278, rs1801274, rs2036108, rs811925, rs883524, rs1065457, rs1148613, rs295, rs290258, rs365836 and rs569214, as characterised in Table 14. The presence of at least one variant allele associated with Alzheimer's disease is an indication that the subject is pre-disposed to Alzheimer's disease. The bases of the variant alleles associated with Alzheimer's disease for the SNPs described above are as follows: rs798893 (C), rs725106 (A), rs1341665 (A), rs1359059 (A), rs1532278 (C), rs1801274 (G), rs2036108 (T), rs811925 (G), rs883524 (C), rs1065457 (G), rs1148613 (C), rs295 (C), rs290258 (G), rs365836 (G) and rs569214 (T) (see Table 14).

The screening methods may also involve genotyping a subject for one or more, two or more, three or more, four or more, five or more, six or more, seven or more, eight or more, nine or more, ten or more polymorphisms selected from the group of polymorphisms consisting of polymorphisms, particularly SNPs, associated with or in linkage disequilibrium (LD) with the single nucleotide polymorphisms: rs798893, rs725106, rs1341665, rs1359059, rs1532278, rs1801274, rs2036108, rs811925, rs883524, rs1065457, rs1148613, rs295, rs290258, rs365836 and rs569214. Polymorphisms "associated" with the SNPs characterised in Table 14 include polymorphisms in close proximity to the identified SNPs. Polymorphisms in linkage disequilibrium with the characterised SNPs could be identified by one of skill in the art using standard association mapping techniques described in the art.

The screening methods of the present invention may be carried out in conjunction with other screening methods used to assess pre-disposition to Alzheimer's disease including use of screening methods based on measuring the expression of the rapamycin-sensitive gene targets described elsewhere herein (see Tables 2-5). Other methods for assessing a subject's pre-disposition or risk of Alzheimer's disease may utilise other known risk factors, including in particular environmental risk factors such as plasma homocysteine levels.

In accordance with the invention, genotyping of polymorphic variants can be carried out using any suitable methodology known in the art and it is to be understood that the invention is in no way limited by the precise technique used to carry out the genotyping.

Known techniques which may be used for genotyping single nucleotide polymorphisms include ligation detection reaction (LDR; Day, D. J., Speiser, P. W., White, P. C. & Barany, F. Genomics 29, 152 62 (1995)), mass spectrometry, particularly matrix-assisted laser desorption/ionization time-of-flight mass spectrometry (MALDI-TOF-MS), single nucleotide primer extension and DNA chips or microarrays (see review by Schafer, A. J. and Hawkins, J. R. in Nature Biotechnology, Vol 16, pp 33-39 (1998)). The use of DNA chips or microarrays may enable simultaneous genotyping at many different polymorphic loci in a single individual or the simultaneous genotyping of a single polymorphic locus in multiple individuals. SNPs may also be scored by DNA sequencing.

In addition to the above, SNPs are commonly scored using PCR-based techniques, such as PCR-SSP using allele-specific primers (described by Bunce M, et al., Tissue Antigens, 1995; 50: 23-31). This method generally involves performing DNA amplification reactions using genomic DNA as the template and two different primer pairs, the first primer pair comprising an allele-specific primer which under appropriate conditions is capable of hybridising selectively to the wild type allele and a non allele-specific primer which binds to a complementary sequence elsewhere within the gene in question, the second primer pair comprising an allele-specific primer which under appropriate conditions is capable of hybridising selectively to the variant allele and the same non allele-specific primer. Further suitable techniques for scoring SNPs include PCR ELISA and denaturing high performance liquid chromatography (DHPLC).

If the SNP results in the abolition or creation of a restriction site, genotyping can be carried out by performing PCR using non-allele specific primers spanning the polymorphic site and digesting the resultant PCR product using the appropriate restriction enzyme (also known as PCR-RFLP). Restriction fragment length polymorphisms, including those resulting from the presence of a single nucleotide polymorphism, may be scored by digesting genomic DNA with an appropriate enzyme then performing a Southern blot using a labelled probe corresponding to the polymorphic region (see Molecular Cloning: A Laboratory Manual, Sambrook, Fritsch and Maniatis, Cold Spring Harbor Laboratory, Cold Spring Harbor, N.Y.).

In the context of the present invention, "genotyping" of any given polymorphic variant may advantageously comprise screening for the presence or absence in the genome of the subject of both the normal or wild type allele and the variant or mutant allele associated with disease, or may comprise screening for the presence or absence of either individual allele, it generally being possible to draw conclusions about the genotype of an individual at a polymorphic locus having two alternative allelic forms just by screening for one or other of the specific alleles.

Alzheimer's disease is a complex and multi-factorial condition. In any given individual the development of AD is likely to be associated with accumulation of genetic variation within a single gene, or across multiple genes, and the accumulated variants may have an additive effect. In view of the foregoing, it is within the scope of the invention to perform genotyping of polymorphisms or polymorphic variants within multiple genes, wherein at least one of the genes is selected from the rapamycin-sensitive genes shown in Table 1. Such a "panel screen" of multiple genes may be used to simultaneously analyse multiple polymorphisms that serve as markers of susceptibility/pre-disposition to Alzheimer's disease in the same human subject. In a preferred embodiment, genotyping of multiple polymorphisms in a single patient sample may be carried out simultaneously, for example with the use of a microarray or "gene chip".

In certain embodiments of the invention, the screening for pre-disposition to Alzheimer's disease will involve genotyping a subject for multiple polymorphisms or polymorphic variants in one or more of the genes shown in Table 1 or multiple polymorphisms or polymorphic variants in one or more genes which affect the expression of one or more of the rapamycin-sensitive genes shown in Table 1, or a combination of both. In the context of the present invention, "multiple" should be taken to mean two or more, three or more, four or more, five or more, six or more etc. The presence of multiple variant alleles associated with Alzheimer's disease is an indication that the subject is pre-disposed to Alzheimer's disease.

In further preferred embodiments, the screening methods will involve genotyping a subject for a combination of single polynucleotide polymorphisms selected from the following:
(i) rs1065457, rs798893 and rs2036108;
(ii) rs1065457, rs1148613, rs290258, rs725106 and rs1341665;
(iii) rs1065457, rs295, rs1359059, rs1532278, rs798893, rs365836, rs725106 and rs1341665;
(iv) rs1148613, rs290258, rs725106, rs1341665 and rs2036108;
(v) rs1065457, rs1148613, rs290258, rs725106, rs1341665 and rs2036108;
(vi) rs1065457, rs1359059, rs725106 and rs2036108; or
(vii) rs798893 and rs725106,
wherein the presence of a combination of variant alleles associated with Alzheimer's disease is an indication that the subject is predisposed to Alzheimer's disease. The variant alleles associated with Alzheimer's disease for each of the SNPs in the combinations described above are as follows: rs798893 (C), rs725106 (A), rs1341665 (A), rs1359059 (A), rs1532278 (C), rs1801274 (G), rs2036108 (T), rs811925 (G), rs883524 (C), rs1065457 (G), rs1148613 (C), rs295 (C), rs290258 (G), rs365836 (G) and rs569214 (T).

Genotyping is preferably carried out in vitro, and is most preferably performed on an isolated sample containing genomic DNA prepared from a suitable tissue sample obtained from the subject under test. Most commonly, genomic DNA is prepared from a sample of whole blood or brain tissue, according to standard procedures which are well known in the art. If genomic sequence data for the individual under test in the region containing the SNP is available, for example in a genomic sequence database as a result of a prior genomic sequencing exercise, then genotyping of the SNP may be accomplished by searching the available sequence data.

In the case of genetic variants which have a detectable effect on the mRNA transcripts transcribed from a given gene, for example variants which cause altered splicing or which affect transcript termination or which affect the level or mRNA expression, then as an alternative to detecting the presence of the variant at the genomic DNA level, the presence of the variant may be inferred by evaluating the mRNA expression pattern using any suitable technique. Similarly, in the case of genetic variants which have a detectable effect on the protein products encoded by a gene, for example variants which cause a change in primary amino acid sequence, structure or properties of the encoded protein, the presence of the variant may be inferred by evaluating the sequence, structure or properties of the protein using any convenient technique.

The above-described screening methods may be used prognostically to identify individuals pre-disposed to Alzheimer's disease (AD) by virtue of their genetic make-up. The "pre-disposition to Alzheimer's disease" may be manifest as an increased risk of developing disease as compared to the general population, or as an earlier age of disease onset as compared to individuals who do not possess a variant allele associated with Alzheimer's disease.

In certain embodiments, the method may be used to screen asymptomatic individuals (i.e. individuals who do not exhibit significant symptoms of AD according to standard diagnostic criteria) in order to identify those "at risk" of developing AD, and/or those likely to exhibit an earlier age of onset of AD. The results of such screens may facilitate early intervention with therapeutic treatments, particularly prophylactic treatments aimed at preventing, reducing or delaying the clinical symptoms of Alzheimer's disease.

In further embodiments the screening methods may be used to screen patients who exhibit clinical symptoms of Alzheimer's disease, for example to assist in correct diagnosis of AD and/or to investigate the genetic basis of suspected or confirmed AD.

Diagnostic Methods Based on Detection of Polymorphisms

In a further aspect, the invention provides a method to assist with diagnosis of Alzheimer's disease in a live human subject, which method comprises genotyping the subject for a polymorphism in one or more of the rapamycin-sensitive genes shown in Table 1, or a polymorphism in one or more genes which affect the expression of one or more of the rapamycin-sensitive genes shown in Table 1, wherein the presence of at least one variant allele associated with Alzheimer's disease is indicative of Alzheimer's disease.

Embodiments of the invention described in the context of diagnostic methods of the invention based on measuring the expression level of one or more rapamycin-sensitive genes are equally applicable to this further aspect of the invention. In addition, embodiments of the invention described in the context of methods for assessing pre-disposition to Alzheimer's disease based on genotyping a subject for one or more polymorphisms are equally applicable to this further aspect of the invention.

Methods to assist with diagnosis of Alzheimer's disease in a live human subject have been described in International patent application no. WO02/073212, incorporated herein by reference. These methods comprise a step of screening non-neuronal cells from a human subject for the presence of a cell cycle regulatory defect at the G1/S transition. One of the ways in which this defect can be assessed is by measuring the responsiveness of the non-neuronal cells to a G1 inhibitor, for example rapamycin. Differential responsiveness to a G1 inhibitor in lymphocytes taken from a subject suspected of having Alzheimer's disease is indicative of disease.

The diagnostic test described in WO02/073212 was developed based on the discovery that Alzheimer's disease is associated with aberrant re-entry of neurons into the cell division cycle. This change is an early event in disease pathogenesis preceding formation of both amyloid-β plaques and neurofibrillary tangles. Therefore, detection of these cell cycle changes may be used to assist with diagnosis of Alzheimer's disease at an early stage, even in asymptomatic individuals.

Previous studies have shown that it is not cell cycle re-entry per se that contributes to Alzheimer's disease but rather the inability of neurons from Alzheimer's disease patients to respond appropriately to this cell-cycle re-entry. In particular, neurons from Alzheimer's disease patients are unable to initiate G1 arrest and subsequently undergo re-differentiation, as a result of a defect in the G1/S regulatory checkpoint. Furthermore, this regulatory defect at the G1/S transition occurs in cells other than neurons in individuals with Alzheimer's disease, for example lymphocytes.

It is therefore possible to assist with the diagnosis of Alzheimer's disease in the live human subject by measuring the differential responsiveness of lymphocytes taken from the subject to G1 inhibitors, such as rapamycin.

The present diagnostic methods are based on the genotyping of a subject to look for the presence of polymorphisms, particularly single nucleotide polymorphisms (SNPs) in rapamycin-sensitive genes or in genes which affect the expression of rapamycin-sensitive genes. Importantly, it has been shown that SNPs within rapamycin-sensitive genes or SNPs in genes which affect the expression of rapamycin-sensitive genes correlate with the differential response to rapamycin observed in lymphocytes collected from individual Alzheimer's disease patients. Therefore, the present methods involve genotyping a subject for a polymorphism in one or more of the rapamycin-sensitive genes shown in Table 1, or a polymorphism in one or more genes which affect the expression of one or more of the rapamycin-sensitive genes shown in Table 1 as an independent means to assist with diagnosis of Alzheimer's disease. In certain embodiments, the methods may involve genotyping a subject for multiple polymorphisms or polymorphic variants in one or more of the genes shown in Table 1 or multiple polymorphisms or polymorphic variants in one or more genes which affect the expression of one or more of the rapamycin-sensitive genes shown in Table 1, or a combination of both. In a preferred embodiment, genotyping of multiple polymorphisms in a single patient sample may be carried out simultaneously, for example with the use of a microarray or "gene chip".

In preferred embodiments, the method comprises genotyping a subject for one or more polymorphisms in one or more rapamycin-sensitive genes selected from LILRB2, FAM5C, CRP, CLU, FCGR2A, CD1E, FAM5C, LPL, SYK and CUX1. Alternatively, or in addition, the method may comprise genotyping a subject for one or more polymorphisms in one or more genes which affect the expression of one or more rapamycin-sensitive genes, wherein the "regulatory" genes are selected from POU2F1, ADRA1A, PRDM1 and LOXL2.

In preferred embodiments, the diagnostic methods involve genotyping a subject for one or more, two or more, three or more, four or more, five or more, six or more, seven or more, eight or more, nine or more, ten or more polymorphisms selected from the group of single nucleotide polymorphisms consisting of rs798893, rs725106, rs1341665, rs1359059, rs1532278, rs1801274, rs2036108, rs811925, rs883524, rs1065457, rs1148613, rs295, rs290258, rs365836 and rs569214, as characterised in Table 14. The presence of at least one variant allele associated with Alzheimer's disease is an indication that the subject is pre-disposed to Alzheimer's disease. The variant alleles associated with Alzheimer's disease for the SNPs described above are as follows: rs798893 (C), rs725106 (A), rs1341665 (A), rs1359059 (A), rs1532278 (C), rs1801274 (G), rs2036108 (T), rs811925 (G), rs883524 (C), rs1065457 (G), rs1148613 (C), rs295 (C), rs290258 (G), rs365836 (G) and rs569214 (T).

The screening methods may also involve genotyping a subject for one or more, two or more, three or more, four or more, five or more, six or more, seven or more, eight or more, nine or more, ten or more polymorphisms selected from the group of polymorphisms consisting of polymorphisms, particularly SNPs, associated with or in linkage disequilibrium (LD) with the single nucleotide polymorphisms: rs798893, rs725106, rs1341665, rs1359059, rs1532278, rs1801274, rs2036108, rs811925, rs883524, rs1065457, rs1148613, rs295, rs290258, rs365836 and rs569214. Polymorphisms "associated" with the SNPs in Table 14 include polymorphisms in close proximity to the characterised SNPs. Polymorphisms in linkage disequilibrium with the characterised SNPs could be identified by one of skill in the art using standard association mapping techniques described in the art.

In further preferred embodiments, the diagnostic methods will involve genotyping a subject for a combination of single polynucleotide polymorphisms selected from the following:
 (i) rs1065457, rs798893 and rs2036108;
 (ii) rs1065457, rs1148613, rs290258, rs725106 and rs1341665;
 (iii) rs1065457, rs295, rs1359059, rs1532278, rs798893, rs365836, rs725106 and rs1341665;
 (iv) rs1148613, rs290258, rs725106, rs1341665 and rs2036108;
 (v) rs1065457, rs1148613, rs290258, rs725106, rs1341665 and rs2036108;
 (vi) rs1065457, rs1359059, rs725106 and rs2036108; or
 (vii) rs798893 and rs725106,
wherein the presence of a combination of variant alleles associated with Alzheimer's disease is indicative of a positive Alzheimer's disease diagnosis.

As noted above, the diagnostic methods described herein may also be used in combination or together with other methods or tests used for Alzheimer's disease diagnosis, for example in order to improve the specificity and/or sensitivity of these methods or tests. In a preferred embodiment, the diagnostic method of the present invention involves a first step of genotyping a subject for a combination of polymorphisms consisting of pr1 and pr10 and a second step of determining plasma homocysteine levels in the same subject.

Arrays and Kits

The present invention also provides arrays and kits for detecting one or more, two or more, three or more, four or more, five or more, six or more, seven or more, eight or more, nine or more, ten or more genetic polymorphisms or polymorphic variants in a sample taken from a subject. The one or more polymorphisms to be detected by the arrays and kits provided herein are in one or more of the rapamycin-sensitive genes shown in Table 1, or in one or more genes which affect the expression of one or more of the rapamycin-sensitive genes shown in Table 1.

Embodiments of the invention already described above in relation to the screening methods and diagnostic methods of the invention relating to the use of polymorphisms are equally applicable to the arrays and kits provided.

The sample taken from the subject may be any sample suitable for genetic analysis including but not limited to blood, saliva, tears, urine, skin, hair or any other tissue containing nucleic acid.

The array or kit may take any suitable format for the detection of polymorphisms, and the reagents forming the array or included in the kit will be dependent on the format adopted by the user. In certain embodiments, the array may take the form of a microarray or "gene chip" wherein oligonucleotides capable of detecting the one or more polymorphisms of interest, if present within the sample, are immobilised on a solid substrate. In certain embodiments, the oligonucleotides are allele-specific oligonucleotides capable of detecting the one or more polymorphisms by hybridisation to the variant allele. The invention therefore provides an array comprising multiple allele-specific oligonucleotides capable of detecting at least two, at least three, at least four, at least five etc different polymorphisms as described elsewhere herein. The design of suitable allele-specific oligonucleotides or probes and the construction of arrays comprising allele-specific oligonucleotides for detecting one or more polymorphisms, particularly SNPs, in a sample could be carried out using standard techniques well known in the art.

Kits according to the present invention may include reagents suitable for carrying out allele-specific Q-PCR, in order to detect one or more polymorphisms. Allele-specific Q-PCR is a variation of the standard polymerase chain reaction, which can be used to identify SNPs in a sample containing nucleic acid. The reagents would include all standard PCR reagents (DNA polymerase, Tris-HCl, $(NH_4)_2SO_4$, $MgCl_2$, Tween20, dATP, dCTP, dTTP, dGTP) and suitable primers with 3' ends encompassing the SNP. Kits may also include allele-specific restriction enzymes, which can be used to detect the presence of SNPs based on the digestion pattern produced when the restriction enzyme digests the nucleic acid sample, as described elsewhere herein.

Methods to Monitor mTOR Signalling

As discussed elsewhere herein, the polymorphisms to be detected in the context of the screening and diagnostic methods described above, are either in one or more of the rapamycin-sensitive genes shown in Table 1, or in one or more genes which affect the expression of one or more of the rapamycin-sensitive genes shown in Table 1. The inhibitor rapamycin is known to inhibit the serine/threonine kinase mTOR in human cells and thereby reduce signalling downstream of this protein. It follows therefore that genes identified as rapamycin-sensitive genes are linked to mTOR signalling in cells.

Therefore, in a further aspect, the present invention also provides a method by which to monitor mTOR signalling in a human cell, which method comprises detecting one or more polymorphisms in one or more of the rapamycin-sensitive genes shown in Table 1, or one or more polymorphisms in one or more genes which affect the expression of one or more of the rapamycin-sensitive genes shown in Table 1, wherein the presence of at least one variant allele associated with a differential response to rapamycin is indicative of the status of mTOR signalling in the cell.

The cytoplasmic kinase mTOR is stimulated or activated by a wide variety of upstream signals. These include signals generated or triggered as a result of nutrient sensing, hypoxia, and/or the activity of growth factors and their cognate receptors. Activation of mTOR upregulates its kinase activity and thereby increases mTOR-mediated phosphorylation of downstream protein targets within the cell. In most cases, the direct downstream protein targets of mTOR interact with a variety of further molecular targets, and in doing so, stimulate a wide variety of cellular responses, such as increased protein synthesis and the promotion of cell growth and proliferation. The chain of molecular events triggered downstream of mTOR-mediated phosphorylation of its direct protein targets is defined herein as the "mTOR signalling pathway".

The methods of the present aspect of the invention allow for the monitoring of mTOR signalling. By "monitoring" is meant determination of the level of activity downstream of the mTOR kinase, for example the level of activity of proteins present within the downstream signalling pathways. Monitoring may be carried out in particular, to determine the functional integrity of the mTOR signalling pathway within a human cell.

In preferred embodiments, the one or more polymorphisms for detection are in one or more of the rapamycin-sensitive genes selected from LILRB2, FAM5C, CRP, CLU, FCGR2A, CD1E, FAM5C, LPL, SYK and CUX1 and/or in one or more of the genes which affect the expression of one or more rapamycin-sensitive genes, selected from POU2F1, ADRA1A, PRDM1 and LOXL2.

In preferred embodiments, the methods involve detecting one or more, two or more, three or more, four or more, five or more, six or more, seven or more, eight or more, nine or more, ten or more polymorphisms selected from the group of single nucleotide polymorphisms consisting of rs798893, rs725106, rs1341665, rs1359059, rs1532278, rs1801274, rs2036108, rs811925, rs883524, rs1065457, rs1148613, rs295, rs290258, rs365836 and rs569214, as characterised in Table 14. The methods may also involve detecting one or more, two or more, three or more, four or more, five or more, six or more, seven or more, eight or more, nine or more, ten or more polymorphisms selected from the group of polymorphisms consisting of polymorphisms, particularly SNPs, associated with or in linkage disequilibrium (LD) with the single nucleotide polymorphisms: rs798893, rs725106, rs1341665, rs1359059, rs1532278, rs1801274, rs2036108, rs811925, rs883524, rs1065457, rs1148613, rs295, rs290258, rs365836 and rs569214.

As described elsewhere herein, cells from subjects with Alzheimer's disease typically exhibit a differential response to G1/S inhibitors, including rapamycin, as a result of a defect in the G1/S cell cycle transition. This differential response is reported in for example, WO02/073212, incorporated herein by reference. The SNPs or variant alleles characterised herein are associated with a differential response to rapamycin as seen in lymphocytes collected from individuals with Alzheimer's disease. As noted above, rapamycin responsiveness is indicative of the status of mTOR signalling in the cell wherein "status" should be taken to mean the functional integrity of signalling through the mTOR signalling pathway. Therefore, the presence of at least one variant allele associated with a differential response to rapamycin may be used to determine the status of mTOR signalling in a cell. In certain embodiments, the presence of at least one variant allele associated with a differential response to rapamycin may be used to determine that the functional integrity of the mTOR signalling pathway is compromised in a particular cell.

Wherein the one or more polymorphisms is/are selected from the group consisting of rs798893, rs725106, rs1341665, rs1359059, rs1532278, rs1801274, rs2036108, rs811925, rs883524, rs1065457, rs1148613, rs295, rs290258, rs365836 and rs569214, the bases of the variant alleles associated with a differential response to rapamycin are as follows: rs798893 (C), rs725106 (A), rs1341665 (A), rs1359059 (A), rs1532278 (C), rs1801274 (G), rs2036108 (T), rs811925 (G), rs883524 (C), rs1065457 (G), rs1148613 (C), rs295 (C), rs290258 (G), rs365836 (G) and rs569214 (T).

The methods of the present invention may be used to monitor mTOR signalling in any type of human cell. For example, the human cell may be a cell pre-treated with a compound such as a pharmacological inhibitor. In a preferred embodiment of the invention, the human cell is a lymphocyte.

Furthermore, in preferred embodiments of the invention, the human cell may be taken from an individual or human subject suspected of having a particular condition or disease, or considered to be at risk of developing a particular disease, most preferably Alzheimer's disease. Wherein the human subject is suspected of having or developing Alzheimer's disease, the cell may be taken from a subject that is asymptomatic for Alzheimer's disease, or a subject who exhibits mild cognitive impairment or a subject exhibiting one or more symptoms consistent with Alzheimer's disease.

The purpose of monitoring mTOR signalling in a cell taken from an individual or subject suspected of having a particular disease or considered at risk of a particular disease, may be to assist with diagnosis of disease in the subject or to assess the subject's pre-disposition to disease. In the preferred embodiment of the present invention wherein the human cell is isolated from a human subject suspected of having Alzheimer's disease, the method may be carried out in order to assist with the diagnosis of Alzheimer's disease or to assess a subject's pre-disposition to Alzheimer's disease.

The present methods may also be used to assist with diagnosis of other diseases or conditions wherein dysregulation of signalling through the mTOR pathway is an underlying cause or consequence, for example cancer, type II diabetes, dementia following brain injury or stroke.

TABLE 1

| Rapamycin-sensitive genes (1051 genes) | | | |
|---|---|---|---|
| Symbol | Entrez Gene Name | Location | Type(s) |
| A2M | alpha-2-macroglobulin | Extracellular Space | transporter |
| AADACL2 | arylacetamide deacetylase-like 2 | unknown | other |
| AASDH | aminoadipate-semialdehyde dehydrogenase | unknown | enzyme |
| ABCA8 | ATP-binding cassette, sub-family A (ABC1), member 8 | Plasma Membrane | transporter |
| ABCB5 | ATP-binding cassette, sub-family B (MDR/TAP), member 5 | Plasma Membrane | transporter |
| ABCD2 | ATP-binding cassette, sub-family D (ALD), member 2 | Cytoplasm | transporter |
| ABHD2 | abhydrolase domain containing 2 | unknown | enzyme |

TABLE 1-continued

Rapamycin-sensitive genes (1051 genes)

| Symbol | Entrez Gene Name | Location | Type(s) |
|---|---|---|---|
| ABI3BP | ABI family, member 3 (NESH) binding protein | Extracellular Space | other |
| ABLIM2 | actin binding LIM protein family, member 2 | Cytoplasm | other |
| ABRA | actin-binding Rho activating protein | Cytoplasm | transcription regulator |
| ABTB1 | ankyrin repeat and BTB (POZ) domain containing 1 | Cytoplasm | translation regulator |
| ACOX2 | acyl-CoA oxidase 2, branched chain | Cytoplasm | enzyme |
| ACPP | acid phosphatase, prostate | Extracellular Space | phosphatase |
| ACSL6 | acyl-CoA synthetase long-chain family member 6 | Cytoplasm | enzyme |
| ACSS1 | acyl-CoA synthetase short-chain family member 1 | Cytoplasm | enzyme |
| ACTRT1 | actin-related protein T1 | Cytoplasm | other |
| ACVR2B | activin A receptor, type IIB | Plasma Membrane | kinase |
| ADAMTS13 | ADAM metallopeptidase with thrombospondin type 1 motif, 13 | Extracellular Space | peptidase |
| ADAMTS15 | ADAM metallopeptidase with thrombospondin type 1 motif, 15 | Extracellular Space | peptidase |
| ADAMTS16 | ADAM metallopeptidase with thrombospondin type 1 motif, 16 | Extracellular Space | other |
| ADAMTS2 | ADAM metallopeptidase with thrombospondin type 1 motif, 2 | Extracellular Space | peptidase |
| ADAMTS20 | ADAM metallopeptidase with thrombospondin type 1 motif, 20 | Extracellular Space | peptidase |
| ADAMTS3 | ADAM metallopeptidase with thrombospondin type 1 motif, 3 | Extracellular Space | peptidase |
| ADAMTS9 | ADAM metallopeptidase with thrombospondin type 1 motif, 9 | Extracellular Space | peptidase |
| ADAMTSL3 | ADAMTS-like 3 | unknown | other |
| ADAMTSL4 | ADAMTS-like 4 | Extracellular Space | other |
| ADAMTSL5 | ADAMTS-like 5 | Extracellular Space | other |
| ADH6 (includes EG: 130) | alcohol dehydrogenase 6 (class V) | Cytoplasm | enzyme |
| ADIPOQ | adiponectin, C1Q and collagen domain containing | Extracellular Space | other |
| ADSSL1 | adenylosuccinate synthase like 1 | Cytoplasm | enzyme |
| AGT | angiotensinogen (serpin peptidase inhibitor, clade A, member 8) | Extracellular Space | growth factor |
| AGTR1 | angiotensin II receptor, type 1 | Plasma Membrane | G-protein coupled receptor |
| AHNAK | AHNAK nucleoprotein | Nucleus | other |
| AHNAK2 | AHNAK nucleoprotein 2 | unknown | other |
| AKR1D1 | aldo-keto reductase family 1, member D1 (delta 4-3-ketosteroid-5-beta-reductase) | Cytoplasm | enzyme |
| ALDH1A3 | aldehyde dehydrogenase 1 family, member A3 | Cytoplasm | enzyme |
| AMY1A (includes others) | amylase, alpha 1A (salivary) | Extracellular Space | enzyme |
| ANGPT2 | angiopoietin 2 | Extracellular Space | growth factor |
| ANGPTL2 | angiopoietin-like 2 | Extracellular Space | other |
| ANGPTL5 | angiopoietin-like 5 | Extracellular Space | other |
| ANK1 | ankyrin 1, erythrocytic | Plasma Membrane | other |
| ANKRD12 | ankyrin repeat domain 12 | Nucleus | other |
| ANKRD36B (includes others) | ankyrin repeat domain 36B | Nucleus | transcription regulator |
| ANKRD36B (includes others) | ankyrin repeat domain 36B | Nucleus | transcription regulator |
| ANKRD42 | ankyrin repeat domain 42 | Nucleus | transcription regulator |
| ANKRD45 | ankyrin repeat domain 45 | Nucleus | transcription regulator |
| ANKRD50 | ankyrin repeat domain 50 | unknown | other |
| ANKRD6 | ankyrin repeat domain 6 | Nucleus | transcription regulator |
| ANKS1B | ankyrin repeat and sterile alpha motif domain containing 1B | Nucleus | other |
| ANO3 | anoctamin 3 | unknown | other |
| ANXA10 | annexin A10 | Cytoplasm | other |
| ANXA2R | annexin A2 receptor | Plasma Membrane | other |
| AP1S1 | adaptor-related protein complex 1, sigma 1 subunit | Cytoplasm | transporter |
| APBB1IP | amyloid beta (A4) precursor protein-binding, family B, member 1 interacting protein | Cytoplasm | other |
| APOB | apolipoprotein B (including Ag(x) antigen) | Extracellular Space | transporter |
| APOBEC3G | apolipoprotein B mRNA editing enzyme, catalytic polypeptide-like 3G | Nucleus | enzyme |
| APOLD1 | apolipoprotein L domain containing 1 | unknown | other |
| AQP12A/AQP12B | aquaporin 12B | Cytoplasm | transporter |
| AQP4 | aquaporin 4 | Plasma Membrane | transporter |
| AQP9 | aquaporin 9 | Plasma Membrane | transporter |

TABLE 1-continued

Rapamycin-sensitive genes (1051 genes)

| Symbol | Entrez Gene Name | Location | Type(s) |
|---|---|---|---|
| AR | androgen receptor | Nucleus | ligand-dependent nuclear receptor |
| ARHGAP28 | Rho GTPase activating protein 28 | Cytoplasm | other |
| ARHGEF4 | Rho guanine nucleotide exchange factor (GEF) 4 | Cytoplasm | other |
| ARHGEF6 | Rac/Cdc42 guanine nucleotide exchange factor (GEF) 6 | Cytoplasm | other |
| ARL14 | ADP-ribosylation factor-like 14 | unknown | other |
| ARL17B/LOC100294341 | ADP-ribosylation factor-like 17B | unknown | other |
| ARMC2 | armadillo repeat containing 2 | unknown | other |
| ARSE | arylsulfatase E (chondrodysplasia punctata 1) | Cytoplasm | enzyme |
| AS3MT | arsenic (+3 oxidation state) methyltransferase | Cytoplasm | enzyme |
| ASB11 | ankyrin repeat and SOCS box containing 11 | Nucleus | transcription regulator |
| ASPM | asp (abnormal spindle) homolog, microcephaly associated (*Drosophila*) | Nucleus | other |
| ASXL3 | additional sex combs like 3 (*Drosophila*) | unknown | other |
| ATAD3A/ATAD3B | ATPase family, AAA domain containing 3A | Nucleus | other |
| ATF7IP | activating transcription factor 7 interacting protein | Nucleus | transcription regulator |
| ATP13A4 | ATPase type 13A4 | unknown | transporter |
| ATP6V0D2 | ATPase, H+ transporting, lysosomal 38 kDa, V0 subunit d2 | Cytoplasm | transporter |
| ATP8B3 | ATPase, aminophospholipid transporter, class I, type 8B, member 3 | Cytoplasm | transporter |
| ATRNL1 | attractin-like 1 | unknown | other |
| AUTS2 | autism susceptibility candidate 2 | unknown | other |
| B2M | beta-2-microglobulin | Plasma Membrane | transmembrane receptor |
| B3GALT4 | UDP-Gal:betaGlcNAc beta 1,3-galactosyltransferase, polypeptide 4 | Cytoplasm | enzyme |
| B4GALT6 | UDP-Gal:betaGlcNAc beta 1,4-galactosyltransferase, polypeptide 6 | Cytoplasm | enzyme |
| BAIAP2 | BAI1-associated protein 2 | Plasma Membrane | kinase |
| BAIAP2L2 | BAI1-associated protein 2-like 2 | Cytoplasm | other |
| BARX2 | BARX homeobox 2 | Nucleus | transcription regulator |
| BCCIP | BRCA2 and CDKN1A interacting protein | Nucleus | other |
| BCL2 | B-cell CLL/lymphoma 2 | Cytoplasm | transporter |
| BEGAIN | brain-enriched guanylate kinase-associated homolog (rat) | Nucleus | other |
| BEND2 | BEN domain containing 2 | unknown | other |
| BEND6 | BEN domain containing 6 | unknown | other |
| BEST3 | bestrophin 3 | Nucleus | ion channel |
| BMP7 | bone morphogenetic protein 7 | Extracellular Space | growth factor |
| BMX | BMX non-receptor tyrosine kinase | Cytoplasm | kinase |
| BNC1 | basonuclin 1 | Nucleus | transcription regulator |
| BPESC1 | blepharophimosis, epicanthus inversus and ptosis, candidate 1 (non-protein coding) | unknown | other |
| BPI | bactericidal/permeability-increasing protein | Plasma Membrane | transporter |
| BPIFB1 | BPI fold containing family B, member 1 | Extracellular Space | other |
| BRIP1 | BRCA1 interacting protein C-terminal helicase 1 | Nucleus | enzyme |
| BSN | bassoon (presynaptic cytomatrix protein) | Plasma Membrane | other |
| BSND | Bartter syndrome, infantile, with sensorineural deafness (Barttin) | Plasma Membrane | ion channel |
| BSPRY | B-box and SPRY domain containing | Cytoplasm | other |
| BTNL9 | butyrophilin-like 9 | unknown | other |
| BVES | blood vessel epicardial substance | Plasma Membrane | other |
| C10orf10 | chromosome 10 open reading frame 10 | Cytoplasm | other |
| C10orf107 | chromosome 10 open reading frame 107 | unknown | other |
| C10orf111 | chromosome 10 open reading frame 111 | unknown | other |
| C11orf67 | chromosome 11 open reading frame 67 | unknown | other |
| C11orf87 | chromosome 11 open reading frame 87 | unknown | other |
| C11orf88 | chromosome 11 open reading frame 88 | unknown | other |
| C12orf42 | chromosome 12 open reading frame 42 | unknown | other |
| C15orf43 | chromosome 15 open reading frame 43 | unknown | other |
| C15orf48 | chromosome 15 open reading frame 48 | Nucleus | other |
| C17orf78 | chromosome 17 open reading frame 78 | unknown | other |
| C17orf99 | chromosome 17 open reading frame 99 | unknown | other |
| C18orf26 | chromosome 18 open reading frame 26 | unknown | other |
| C1orf110 | chromosome 1 open reading frame 110 | unknown | other |
| C1orf127 | chromosome 1 open reading frame 127 | unknown | other |
| C1orf173 | chromosome 1 open reading frame 173 | unknown | other |
| C1orf226 | chromosome 1 open reading frame 226 | unknown | other |

TABLE 1-continued

Rapamycin-sensitive genes (1051 genes)

| Symbol | Entrez Gene Name | Location | Type(s) |
|---|---|---|---|
| C1orf87 | chromosome 1 open reading frame 87 | unknown | other |
| C1QTNF6 | C1q and tumor necrosis factor related protein 6 | Extracellular Space | other |
| C20orf132 | chromosome 20 open reading frame 132 | unknown | other |
| C20orf85 | chromosome 20 open reading frame 85 | unknown | other |
| C2orf16 | chromosome 2 open reading frame 16 | unknown | other |
| C3orf36 | chromosome 3 open reading frame 36 | unknown | other |
| C3orf70 | chromosome 3 open reading frame 70 | unknown | other |
| C4orf19 | chromosome 4 open reading frame 19 | unknown | other |
| C4orf22 | chromosome 4 open reading frame 22 | unknown | other |
| C4orf26 | chromosome 4 open reading frame 26 | unknown | other |
| C4orf36 | chromosome 4 open reading frame 36 | unknown | other |
| C6orf223 | chromosome 6 open reading frame 223 | unknown | other |
| C7orf41 | chromosome 7 open reading frame 41 | unknown | other |
| C8orf42 | chromosome 8 open reading frame 42 | unknown | other |
| CA12 | carbonic anhydrase XII | Plasma Membrane | enzyme |
| CA6 | carbonic anhydrase VI | Extracellular Space | enzyme |
| CACNA1D | calcium channel, voltage-dependent, L type, alpha 1D subunit | Plasma Membrane | ion channel |
| CADPS | Ca++-dependent secretion activator | Plasma Membrane | other |
| CALD1 | caldesmon 1 | Cytoplasm | other |
| CARD14 | caspase recruitment domain family, member 14 | Cytoplasm | other |
| CATSPER2 | cation channel, sperm associated 2 | Plasma Membrane | ion channel |
| CATSPERD | catsper channel auxiliary subunit delta | unknown | other |
| CAV2 | caveolin 2 | Plasma Membrane | other |
| CBX7 | chromobox homolog 7 | Nucleus | other |
| CC2D2A | coiled-coil and C2 domain containing 2A | unknown | other |
| CCDC141 | coiled-coil domain containing 141 | unknown | other |
| CCDC28A | coiled-coil domain containing 28A | unknown | other |
| CCDC34 | coiled-coil domain containing 34 | unknown | other |
| CCDC40 | coiled-coil domain containing 40 | unknown | other |
| CCDC85A | coiled-coil domain containing 85A | unknown | other |
| CCL1 | chemokine (C-C motif) ligand 1 | Extracellular Space | cytokine |
| CCL11 | chemokine (C-C motif) ligand 11 | Extracellular Space | cytokine |
| CCL2 | chemokine (C-C motif) ligand 2 | Extracellular Space | cytokine |
| CCL26 | chemokine (C-C motif) ligand 26 | Extracellular Space | cytokine |
| CCL8 | chemokine (C-C motif) ligand 8 | Extracellular Space | cytokine |
| CCNB2 | cyclin B2 | Cytoplasm | other |
| CCNG2 | cyclin G2 | Nucleus | other |
| CCR1 | chemokine (C-C motif) receptor 1 | Plasma Membrane | G-protein coupled receptor |
| CCR2 | chemokine (C-C motif) receptor 2 | Plasma Membrane | G-protein coupled receptor |
| CD177 | CD177 molecule | Cytoplasm | other |
| CD1A | CD1a molecule | Plasma Membrane | other |
| CD1B | CD1b molecule | Plasma Membrane | other |
| CD1E | CD1e molecule | Cytoplasm | other |
| CD44 (includes EG: 100330801) | CD44 molecule (Indian blood group) | Plasma Membrane | enzyme |
| CD69 | CD69 molecule | Plasma Membrane | transmembrane receptor |
| CD96 | CD96 molecule | Plasma Membrane | other |
| CDC14B | CDC14 cell division cycle 14 homolog B (*S. cerevisiae*) | Nucleus | phosphatase |
| CDCP1 | CUB domain containing protein 1 | Plasma Membrane | other |
| CDCP2 | CUB domain containing protein 2 | unknown | transporter |
| CDH1 | cadherin 1, type 1, E-cadherin (epithelial) | Plasma Membrane | other |
| CDH13 | cadherin 13, H-cadherin (heart) | Plasma Membrane | other |
| CDH26 | cadherin 26 | Plasma Membrane | other |
| CDH7 | cadherin 7, type 2 | Plasma Membrane | other |
| CDHR1 | cadherin-related family member 1 | Plasma Membrane | other |
| CDKN1B | cyclin-dependent kinase inhibitor 1B (p27, Kip1) | Nucleus | kinase |
| CDKN1C | cyclin-dependent kinase inhibitor 1C (p57, Kip2) | Nucleus | other |
| CDKN2C | cyclin-dependent kinase inhibitor 2C (p18, inhibits CDK4) | Nucleus | transcription regulator |
| CDKN2D | cyclin-dependent kinase inhibitor 2D (p19, inhibits CDK4) | Nucleus | transcription regulator |
| CDON | Cdon homolog (mouse) | Plasma Membrane | other |
| CEACAM1 (includes others) | carcinoembryonic antigen-related cell adhesion molecule 1 (biliary glycoprotein) | Plasma Membrane | transmembrane receptor |
| CELF3 | CUGBP, Elav-like family member 3 | Nucleus | transcription regulator |
| CELF4 | CUGBP, Elav-like family member 4 | Nucleus | translation regulator |
| CELF6 | CUGBP, Elav-like family member 6 | unknown | other |
| CEP68 | centrosomal protein 68 kDa | Cytoplasm | other |

TABLE 1-continued

Rapamycin-sensitive genes (1051 genes)

| Symbol | Entrez Gene Name | Location | Type(s) |
|---|---|---|---|
| CFHR5 | complement factor H-related 5 | Extracellular Space | other |
| CFTR | cystic fibrosis transmembrane conductance regulator (ATP-binding cassette sub-family C, member 7) | Plasma Membrane | ion channel |
| CGA | glycoprotein hormones, alpha polypeptide | Extracellular Space | other |
| CGNL1 | cingulin-like 1 | Plasma Membrane | other |
| CHD2 | chromodomain helicase DNA binding protein 2 | Nucleus | enzyme |
| CHP2 | calcineurin B homologous protein 2 | Cytoplasm | other |
| CHRDL2 | chordin-like 2 | Extracellular Space | other |
| CHRNA9 | cholinergic receptor, nicotinic, alpha 9 (neuronal) | Plasma Membrane | transmembrane receptor |
| CKM | creatine kinase, muscle | Cytoplasm | kinase |
| CLC | Charcot-Leyden crystal protein | Cytoplasm | enzyme |
| CLCA2 | chloride channel accessory 2 | Plasma Membrane | ion channel |
| CLEC7A | C-type lectin domain family 7, member A | Plasma Membrane | transmembrane receptor |
| CLTB | clathrin, light chain B | Plasma Membrane | other |
| CLVS1 | clavesin 1 | Cytoplasm | other |
| CNRIP1 | cannabinoid receptor interacting protein 1 | unknown | other |
| CNTN3 | contactin 3 (plasmacytoma associated) | Plasma Membrane | other |
| COBL | cordon-bleu homolog (mouse) | unknown | other |
| COL11A1 | collagen, type XI, alpha 1 | Extracellular Space | other |
| COL13A1 | collagen, type XIII, alpha 1 | Plasma Membrane | other |
| COL1A2 | collagen, type I, alpha 2 | Extracellular Space | other |
| COL6A3 | collagen, type VI, alpha 3 | Extracellular Space | other |
| COL6A6 | collagen, type VI, alpha 6 | Extracellular Space | other |
| COL8A2 | collagen, type VIII, alpha 2 | Extracellular Space | other |
| COMMD6 | COMM domain containing 6 | unknown | other |
| CORIN | corin, serine peptidase | Plasma Membrane | peptidase |
| CORO2A | coronin, actin binding protein, 2A | Cytoplasm | other |
| CPB2 | carboxypeptidase B2 (plasma) | Extracellular Space | peptidase |
| CPE (includes EG: 12876) | carboxypeptidase E | Plasma Membrane | peptidase |
| CPLX2 | complexin 2 | Cytoplasm | other |
| CPXM2 | carboxypeptidase X (M14 family), member 2 | Extracellular Space | peptidase |
| CRB1 | crumbs homolog 1 (Drosophila) | Plasma Membrane | other |
| CREB3L4 | cAMP responsive element binding protein 3-like 4 | Nucleus | transcription regulator |
| CREBRF | CREB3 regulatory factor | unknown | other |
| CRIM1 | cysteine rich transmembrane BMP regulator 1 (chordin-like) | Extracellular Space | kinase |
| CROT | carnitine O-octanoyltransferase | Cytoplasm | enzyme |
| CRP | C-reactive protein, pentraxin-related | Extracellular Space | other |
| CRTAC1 | cartilage acidic protein 1 | Extracellular Space | other |
| CRYBG3 | beta-gamma crystallin domain containing 3 | unknown | other |
| CRYGB | crystallin, gamma B | Nucleus | other |
| CRYGD | crystallin, gamma D | Cytoplasm | other |
| CSDC2 | cold shock domain containing C2, RNA binding | Cytoplasm | other |
| CSF1R | colony stimulating factor 1 receptor | Plasma Membrane | kinase |
| CSN2 | casein beta | Extracellular Space | kinase |
| CTAG1B (includes others) | cancer/testis antigen 1B | Cytoplasm | other |
| CTDSP1 | CTD (carboxy-terminal domain, RNA polymerase II, polypeptide A) small phosphatase 1 | Nucleus | phosphatase |
| CTNNA3 | catenin (cadherin-associated protein), alpha 3 | Plasma Membrane | other |
| CTSF | cathepsin F | Cytoplasm | peptidase |
| CXorf51A/CXorf51B | chromosome X open reading frame 51A | unknown | other |
| CYP2C9 | cytochrome P450, family 2, subfamily C, polypeptide 9 | Cytoplasm | enzyme |
| CYP3A5 | cytochrome P450, family 3, subfamily A, polypeptide 5 | Cytoplasm | enzyme |
| CYP4F11 | cytochrome P450, family 4, subfamily F, polypeptide 11 | Cytoplasm | enzyme |
| CYP4F2 | cytochrome P450, family 4, subfamily F, polypeptide 2 | Cytoplasm | enzyme |
| CYP4F3 | cytochrome P450, family 4, subfamily F, polypeptide 3 | Cytoplasm | enzyme |
| CYP4V2 | cytochrome P450, family 4, subfamily V, polypeptide 2 | Cytoplasm | enzyme |
| CYP4X1 | cytochrome P450, family 4, subfamily X, polypeptide 1 | Cytoplasm | enzyme |
| CYP4Z1 | cytochrome P450, family 4, subfamily Z, polypeptide 1 | Cytoplasm | enzyme |
| CYR61 | cysteine-rich, angiogenic inducer, 61 | Extracellular Space | other |
| CYSLTR2 | cysteinyl leukotriene receptor 2 | Plasma Membrane | G-protein coupled receptor |
| DAOA | D-amino acid oxidase activator | Cytoplasm | other |
| DAPL1 | death associated protein-like 1 | unknown | other |
| DCAF12L1 | DDB1 and CUL4 associated factor 12-like 1 | unknown | other |
| DCC | deleted in colorectal carcinoma | Plasma Membrane | transmembrane receptor |
| DCD | dermcidin | Extracellular Space | other |
| DCLK1 | doublecortin-like kinase 1 | Plasma Membrane | kinase |

TABLE 1-continued

Rapamycin-sensitive genes (1051 genes)

| Symbol | Entrez Gene Name | Location | Type(s) |
| --- | --- | --- | --- |
| DCN | decorin | Extracellular Space | other |
| DDI1 (includes EG: 367012) | DNA-damage inducible 1 homolog 1 (*S. cerevisiae*) | unknown | other |
| DDX17 | DEAD (Asp-Glu-Ala-Asp) box helicase 17 | Nucleus | enzyme |
| DEFA4 | defensin, alpha 4, corticostatin | Extracellular Space | other |
| DEFB119 | defensin, beta 119 | Extracellular Space | other |
| DHRS12 | dehydrogenase/reductase (SDR family) member 12 | Nucleus | other |
| DHRS3 | dehydrogenase/reductase (SDR family) member 3 | Cytoplasm | enzyme |
| DKFZP586K1520 | DKFZP586K1520 protein | unknown | other |
| DLEU7 | deleted in lymphocytic leukemia, 7 | unknown | other |
| DLG2 | discs, large homolog 2 (*Drosophila*) | Plasma Membrane | kinase |
| DLGAP4 | discs, large (*Drosophila*) homolog-associated protein 4 | Plasma Membrane | other |
| DLX2 | distal-less homeobox 2 | Nucleus | transcription regulator |
| DMRTB1 | DMRT-like family B with proline-rich C-terminal, 1 | Nucleus | transcription regulator |
| DMRTC1/DMRTC1B | DMRT-like family C1B | unknown | other |
| DMRTC2 | DMRT-like family C2 | Nucleus | transcription regulator |
| DNAH1 | dynein, axonemal, heavy chain 1 | unknown | other |
| DNAH6 | dynein, axonemal, heavy chain 6 | unknown | other |
| DNAJB7 | DnaJ (Hsp40) homolog, subfamily B, member 7 | unknown | other |
| DPY19L1P1 | dpy-19-like 1 pseudogene 1 (*C. elegans*) | unknown | other |
| DRP2 | dystrophin related protein 2 | Plasma Membrane | other |
| DSEL | dermatan sulfate epimerase-like | unknown | enzyme |
| DST | dystonin | Plasma Membrane | other |
| DTD1 | D-tyrosyl-tRNA deacylase 1 homolog (*S. cerevisiae*) | Cytoplasm | enzyme |
| DUSP13 | dual specificity phosphatase 13 | Cytoplasm | phosphatase |
| DUSP21 | dual specificity phosphatase 21 | Cytoplasm | phosphatase |
| DUSP27 | dual specificity phosphatase 27 (putative) | unknown | phosphatase |
| DYNC2LI1 | dynein, cytoplasmic 2, light intermediate chain 1 | Cytoplasm | other |
| DYNLRB1 | dynein, light chain, roadblock-type 1 | Cytoplasm | other |
| DZIP1L | DAZ interacting protein 1-like | unknown | other |
| DZIP3 | DAZ interacting protein 3, zinc finger | Cytoplasm | enzyme |
| EBF2 | early B-cell factor 2 | Nucleus | other |
| EBF3 | early B-cell factor 3 | Nucleus | other |
| ECHDC2 | enoyl CoA hydratase domain containing 2 | unknown | other |
| ECM2 (includes EG: 1842) | extracellular matrix protein 2, female organ and adipocyte specific | Extracellular Space | other |
| ECT2L | epithelial cell transforming sequence 2 oncogene-like | unknown | other |
| EDDM3A | epididymal protein 3A | Extracellular Space | other |
| EDDM3B | epididymal protein 3B | Extracellular Space | other |
| EEPD1 | endonuclease/exonuclease/phosphatase family domain containing 1 | unknown | other |
| EFCAB3 | EF-hand calcium binding domain 3 | unknown | other |
| EGF (includes EG: 13645) | epidermal growth factor | Extracellular Space | growth factor |
| EGLN3 | egl nine homolog 3 (*C. elegans*) | Cytoplasm | enzyme |
| EGR1 | early growth response 1 | Nucleus | transcription regulator |
| ELAVL3 | ELAV (embryonic lethal, abnormal vision, *Drosophila*)-like 3 (Hu antigen C) | Nucleus | other |
| ELAVL4 | ELAV (embryonic lethal, abnormal vision, *Drosophila*)-like 4 (Hu antigen D) | Cytoplasm | other |
| ELOVL7 | ELOVL fatty acid elongase 7 | Cytoplasm | enzyme |
| EMCN | endomucin | Extracellular Space | other |
| EMX2OS | EMX2 opposite strand/antisense RNA (non-protein coding) | unknown | other |
| ENPEP | glutamyl aminopeptidase (aminopeptidase A) | Plasma Membrane | peptidase |
| ENPP6 | ectonucleotide pyrophosphatase/phosphodiesterase 6 | Cytoplasm | enzyme |
| ENTPD8 | ectonucleoside triphosphate diphosphohydrolase 8 | unknown | enzyme |
| EPB41L4B | erythrocyte membrane protein band 4.1 like 4B | unknown | transporter |
| EPHA5 | EPH receptor A5 | Plasma Membrane | kinase |
| EPO | erythropoietin | Extracellular Space | cytokine |
| ERBB3 (includes EG: 13867) | v-erb-b2 erythroblastic leukemia viral oncogene homolog 3 (avian) | Plasma Membrane | kinase |
| ERBB4 | v-erb-a erythroblastic leukemia viral oncogene homolog 4 (avian) | Plasma Membrane | kinase |
| ESR1 | estrogen receptor 1 | Nucleus | ligand-dependent nuclear receptor |
| ESYT3 | extended synaptotagmin-like protein 3 | unknown | other |
| EYA1 | eyes absent homolog 1 (*Drosophila*) | Nucleus | phosphatase |
| F11 | coagulation factor XI | Extracellular Space | peptidase |
| F2 | coagulation factor II (thrombin) | Extracellular Space | peptidase |

TABLE 1-continued

Rapamycin-sensitive genes (1051 genes)

| Symbol | Entrez Gene Name | Location | Type(s) |
|---|---|---|---|
| F2RL2 | coagulation factor II (thrombin) receptor-like 2 | Plasma Membrane | G-protein coupled receptor |
| F9 | coagulation factor IX | Extracellular Space | peptidase |
| FAM100B | family with sequence similarity 100, member B | unknown | other |
| FAM135B | family with sequence similarity 135, member B | unknown | enzyme |
| FAM13C | family with sequence similarity 13, member C | unknown | other |
| FAM149B1 | family with sequence similarity 149, member B1 | unknown | other |
| FAM153A/FAM153B | family with sequence similarity 153, member A | unknown | other |
| FAM155A | family with sequence similarity 155, member A | unknown | other |
| FAM162B | family with sequence similarity 162, member B | unknown | other |
| FAM171B | family with sequence similarity 171, member B | unknown | other |
| FAM172A | family with sequence similarity 172, member A | Cytoplasm | transcription regulator |
| FAM177A1 | family with sequence similarity 177, member A1 | unknown | other |
| FAM181B | family with sequence similarity 181, member B | unknown | other |
| FAM19A1 | family with sequence similarity 19 (chemokine (C-C motif)-like), member A1 | unknown | other |
| FAM211A | family with sequence similarity 211, member A | unknown | other |
| FAM24A | family with sequence similarity 24, member A | unknown | other |
| FAM26D | family with sequence similarity 26, member D | unknown | other |
| FAM27E3 (includes others) | family with sequence similarity 27, member E3 | unknown | other |
| FAM43B | family with sequence similarity 43, member B | unknown | other |
| FAM5C | family with sequence similarity 5, member C | Cytoplasm | other |
| FAM64A | family with sequence similarity 64, member A | Nucleus | other |
| FAM71D | family with sequence similarity 71, member D | unknown | other |
| FAM74A3 | family with sequence similarity 74, member A3 | unknown | other |
| FAM84A | family with sequence similarity 84, member A | unknown | other |
| FAM92B | family with sequence similarity 92, member B | unknown | other |
| FAT3 | FAT tumor suppressor homolog 3 (*Drosophila*) | unknown | other |
| FAXC | failed axon connections homolog (*Drosophila*) | unknown | other |
| FBLN1 | fibulin 1 | Extracellular Space | other |
| FBN2 (includes EG: 14119) | fibrillin 2 | Extracellular Space | other |
| FBP2 | fructose-1,6-bisphosphatase 2 | Cytoplasm | phosphatase |
| FBXL16 | F-box and leucine-rich repeat protein 16 | unknown | other |
| FCGBP | Fc fragment of IgG binding protein | Extracellular Space | other |
| FGB (includes EG: 110135) | fibrinogen beta chain | Extracellular Space | other |
| FGF11 | fibroblast growth factor 11 | Extracellular Space | growth factor |
| FGF18 | fibroblast growth factor 18 | Extracellular Space | growth factor |
| FGF2 | fibroblast growth factor 2 (basic) | Extracellular Space | growth factor |
| FGF23 | fibroblast growth factor 23 | Extracellular Space | growth factor |
| FGF7 | fibroblast growth factor 7 | Extracellular Space | growth factor |
| FGFR1 | fibroblast growth factor receptor 1 | Plasma Membrane | kinase |
| FGG | fibrinogen gamma chain | Extracellular Space | other |
| FGGY | FGGY carbohydrate kinase domain containing | unknown | other |
| FGR | Gardner-Rasheed feline sarcoma viral (v-fgr) oncogene homolog | Nucleus | kinase |
| FIGN | fidgetin | Nucleus | other |
| FILIP1 | filamin A interacting protein 1 | Cytoplasm | other |
| FJX1 | four jointed box 1 (*Drosophila*) | Extracellular Space | other |
| FLJ35946 | uncharacterized protein FLJ35946 | unknown | other |
| FLJ36000 | uncharacterized FLJ36000 | unknown | other |
| FLJ37035 | uncharacterized LOC399821 | unknown | other |
| FLJ37644 | uncharacterized LOC400618 | unknown | other |
| FLJ42875 | uncharacterized LOC440556 | unknown | other |
| FMN2 | formin 2 | unknown | other |
| FMO3 | flavin containing monooxygenase 3 | Cytoplasm | enzyme |
| FN1 | fibronectin 1 | Extracellular Space | enzyme |
| FN3K | fructosamine 3 kinase | Cytoplasm | kinase |
| FNBP1 | formin binding protein 1 | Nucleus | enzyme |
| FNDC5 | fibronectin type III domain containing 5 | unknown | other |
| FRAT2 | frequently rearranged in advanced T-cell lymphomas 2 | Cytoplasm | other |
| FREM3 | FRAS1 related extracellular matrix 3 | Extracellular Space | other |
| FRMD4A | FERM domain containing 4A | Plasma Membrane | other |
| FRMD6 | FERM domain containing 6 | Cytoplasm | other |
| FRMD7 | FERM domain containing 7 | Plasma Membrane | other |
| FSTL5 | follistatin-like 5 | Extracellular Space | other |
| FUT9 | fucosyltransferase 9 (alpha (1,3) fucosyltransferase) | Cytoplasm | enzyme |
| G0S2 | G0/G1switch 2 | Cytoplasm | other |
| GAB1 | GRB2-associated binding protein 1 | Cytoplasm | other |
| GABBR2 | gamma-aminobutyric acid (GABA) B receptor, 2 | Plasma Membrane | G-protein coupled receptor |

TABLE 1-continued

Rapamycin-sensitive genes (1051 genes)

| Symbol | Entrez Gene Name | Location | Type(s) |
|---|---|---|---|
| GABRA1 | gamma-aminobutyric acid (GABA) A receptor, alpha 1 | Plasma Membrane | ion channel |
| GABRA5 | gamma-aminobutyric acid (GABA) A receptor, alpha 5 | Plasma Membrane | ion channel |
| GABRG1 | gamma-aminobutyric acid (GABA) A receptor, gamma 1 | Plasma Membrane | ion channel |
| GABRR2 | gamma-aminobutyric acid (GABA) A receptor, rho 2 | Plasma Membrane | ion channel |
| GAGE1 (includes others) | G antigen 1 | unknown | other |
| GALNT10 | UDP-N-acetyl-alpha-D-galactosamine:polypeptide N-acetylgalactosaminyltransferase 10 (GalNAc-T10) | Cytoplasm | enzyme |
| GALNT5 | UDP-N-acetyl-alpha-D-galactosamine:polypeptide N-acetylgalactosaminyltransferase 5 (GalNAc-T5) | Cytoplasm | enzyme |
| GBP3 | guanylate binding protein 3 | Cytoplasm | enzyme |
| GCM2 | glial cells missing homolog 2 (*Drosophila*) | Nucleus | transcription regulator |
| GDA | guanine deaminase | Cytoplasm | enzyme |
| GFAP | glial fibrillary acidic protein | Cytoplasm | other |
| GFRA1 | GDNF family receptor alpha 1 | Plasma Membrane | transmembrane receptor |
| GFRA2 | GDNF family receptor alpha 2 | Plasma Membrane | transmembrane receptor |
| GHRLOS | ghrelin opposite strand/antisense RNA (non-protein coding) | unknown | other |
| GIGYF1 | GRB10 interacting GYF protein 1 | unknown | other |
| GIPR | gastric inhibitory polypeptide receptor | Plasma Membrane | G-protein coupled receptor |
| GLI2 | GLI family zinc finger 2 | Nucleus | transcription regulator |
| GLP1R | glucagon-like peptide 1 receptor | Plasma Membrane | G-protein coupled receptor |
| GLRA1 | glycine receptor, alpha 1 | Plasma Membrane | ion channel |
| GNAL | guanine nucleotide binding protein (G protein), alpha activating activity polypeptide, olfactory type | Cytoplasm | enzyme |
| GNG8 | guanine nucleotide binding protein (G protein), gamma 8 | Plasma Membrane | enzyme |
| GPAM | glycerol-3-phosphate acyltransferase, mitochondrial | Cytoplasm | enzyme |
| GPC3 | glypican 3 | Plasma Membrane | other |
| GPR110 | G protein-coupled receptor 110 | Plasma Membrane | G-protein coupled receptor |
| GPR116 | G protein-coupled receptor 116 | Plasma Membrane | G-protein coupled receptor |
| GPR176 | G protein-coupled receptor 176 | Plasma Membrane | G-protein coupled receptor |
| GPR34 | G protein-coupled receptor 34 | Plasma Membrane | G-protein coupled receptor |
| GPR37 | G protein-coupled receptor 37 (endothelin receptor type B-like) | Plasma Membrane | G-protein coupled receptor |
| GPR4 | G protein-coupled receptor 4 | Plasma Membrane | G-protein coupled receptor |
| GPX6 | glutathione peroxidase 6 (olfactory) | Extracellular Space | enzyme |
| GPX8 | glutathione peroxidase 8 (putative) | unknown | enzyme |
| GRIA1 | glutamate receptor, ionotropic, AMPA 1 | Plasma Membrane | ion channel |
| GRIA2 | glutamate receptor, ionotropic, AMPA 2 | Plasma Membrane | ion channel |
| GRIA3 | glutamate receptor, ionotropic, AMPA 3 | Plasma Membrane | ion channel |
| GRIK2 | glutamate receptor, ionotropic, kainate 2 | Plasma Membrane | ion channel |
| GRIK3 | glutamate receptor, ionotropic, kainate 3 | Plasma Membrane | ion channel |
| GRM1 | glutamate receptor, metabotropic 1 | Plasma Membrane | G-protein coupled receptor |
| GRPR | gastrin-releasing peptide receptor | Plasma Membrane | G-protein coupled receptor |
| GSG1L | GSG1-like | unknown | other |
| GSN | gelsolin | Extracellular Space | other |
| GSTA1 | glutathione S-transferase alpha 1 | Cytoplasm | enzyme |
| GSTA5 | glutathione S-transferase alpha 5 | Cytoplasm | enzyme |
| GSTM3 | glutathione S-transferase mu 3 (brain) | Cytoplasm | enzyme |
| GUCY1A3 | guanylate cyclase 1, soluble, alpha 3 | Cytoplasm | enzyme |
| GUCY2F | guanylate cyclase 2F, retinal | Plasma Membrane | kinase |

TABLE 1-continued

Rapamycin-sensitive genes (1051 genes)

| Symbol | Entrez Gene Name | Location | Type(s) |
|---|---|---|---|
| GVINP1 | GTPase, very large interferon inducible pseudogene 1 | Cytoplasm | other |
| HABP2 | hyaluronan binding protein 2 | Extracellular Space | peptidase |
| HAND1 | heart and neural crest derivatives expressed 1 | Nucleus | transcription regulator |
| HAND2 | heart and neural crest derivatives expressed 2 | Nucleus | transcription regulator |
| HAPLN1 | hyaluronan and proteoglycan link protein 1 | Extracellular Space | other |
| HCAR3 | hydroxycarboxylic acid receptor 3 | Plasma Membrane | G-protein coupled receptor |
| HCK | hemopoietic cell kinase | Cytoplasm | kinase |
| HDAC5 | histone deacetylase 5 | Nucleus | transcription regulator |
| HDAC9 | histone deacetylase 9 | Nucleus | transcription regulator |
| HESX1 | HESX homeobox 1 | Nucleus | transcription regulator |
| HGF | hepatocyte growth factor (hepapoietin A; scatter factor) | Extracellular Space | growth factor |
| HHIP | hedgehog interacting protein | Plasma Membrane | other |
| HHIPL1 | HHIP-like 1 | unknown | other |
| HIST1H2BN | histone cluster 1, H2bn | Nucleus | other |
| HIST1H4A (includes others) | histone cluster 1, H4a | Nucleus | other |
| HIVEP2 | human immunodeficiency virus type I enhancer binding protein 2 | Nucleus | transcription regulator |
| HMGCS2 | 3-hydroxy-3-methylglutaryl-CoA synthase 2 (mitochondrial) | Cytoplasm | enzyme |
| HNF4G | hepatocyte nuclear factor 4, gamma | Nucleus | transcription regulator |
| HOXA2 | homeobox A2 | Nucleus | transcription regulator |
| HOXA9 | homeobox A9 | Nucleus | transcription regulator |
| HOXC8 | homeobox C8 | Nucleus | transcription regulator |
| HOXD10 | homeobox D10 | Nucleus | transcription regulator |
| HRASLS5 | HRAS-like suppressor family, member 5 | unknown | other |
| HSD17B13 | hydroxysteroid (17-beta) dehydrogenase 13 | Extracellular Space | enzyme |
| HTN3 | histatin 3 | Extracellular Space | other |
| HTR2C | 5-hydroxytryptamine (serotonin) receptor 2C, G protein-coupled | Plasma Membrane | G-protein coupled receptor |
| HTR3C | 5-hydroxytryptamine (serotonin) receptor 3C, ionotropic | Plasma Membrane | ion channel |
| HYDIN | HYDIN, axonemal central pair apparatus protein | unknown | other |
| IFFO1 | intermediate filament family orphan 1 | unknown | other |
| IFIT2 | interferon-induced protein with tetratricopeptide repeats 2 | Cytoplasm | other |
| IFNA16 | interferon, alpha 16 | Extracellular Space | cytokine |
| IGBP1 | immunoglobulin (CD79A) binding protein 1 | Cytoplasm | phosphatase |
| IGF2 | insulin-like growth factor 2 (somatomedin A) | Extracellular Space | growth factor |
| IKZF4 | IKAROS family zinc finger 4 (Eos) | Nucleus | transcription regulator |
| IL10 | interleukin 10 | Extracellular Space | cytokine |
| IL17B | interleukin 17B | Extracellular Space | cytokine |
| IL18 (includes EG: 16173) | interleukin 18 (interferon-gamma-inducing factor) | Extracellular Space | cytokine |
| IL1B | interleukin 1, beta | Extracellular Space | cytokine |
| IL1RAPL1 | interleukin 1 receptor accessory protein-like 1 | Plasma Membrane | transmembrane receptor |
| IL1RN | interleukin 1 receptor antagonist | Extracellular Space | cytokine |
| IL2 | interleukin 2 | Extracellular Space | cytokine |
| IL3 | interleukin 3 (colony-stimulating factor, multiple) | Extracellular Space | other |
| IL31 | interleukin 31 | unknown | other |
| IL6 | interleukin 6 (interferon, beta 2) | Extracellular Space | cytokine |
| IMPG1 | interphotoreceptor matrix proteoglycan 1 | Extracellular Space | other |
| INGX | inhibitor of growth family, X-linked, pseudogene | unknown | other |
| INPP5E | inositol polyphosphate-5-phosphatase, 72 kDa | Cytoplasm | phosphatase |
| INPP5K | inositol polyphosphate-5-phosphatase K | Cytoplasm | phosphatase |
| INSL5 | insulin-like 5 | Extracellular Space | other |
| IQCF1 | IQ motif containing F1 | unknown | other |
| IRS2 | insulin receptor substrate 2 | Cytoplasm | enzyme |
| IRX4 | iroquois homeobox 4 | Nucleus | transcription regulator |

TABLE 1-continued

Rapamycin-sensitive genes (1051 genes)

| Symbol | Entrez Gene Name | Location | Type(s) |
|---|---|---|---|
| ISX | intestine-specific homeobox | unknown | other |
| ITGB3 | integrin, beta 3 (platelet glycoprotein IIIa, antigen CD61) | Plasma Membrane | transmembrane receptor |
| ITGBL1 | integrin, beta-like 1 (with EGF-like repeat domains) | unknown | other |
| JAK1 (includes EG: 16451) | Janus kinase 1 | Cytoplasm | kinase |
| JAKMIP3 | Janus kinase and microtubule interacting protein 3 | unknown | other |
| JARID2 | jumonji, AT rich interactive domain 2 | Nucleus | transcription regulator |
| JUN | jun proto-oncogene | Nucleus | transcription regulator |
| KANK2 | KN motif and ankyrin repeat domains 2 | Nucleus | transcription regulator |
| KCNA3 | potassium voltage-gated channel, shaker-related subfamily, member 3 | Plasma Membrane | ion channel |
| KCNA4 | potassium voltage-gated channel, shaker-related subfamily, member 4 | Plasma Membrane | ion channel |
| KCNA7 | potassium voltage-gated channel, shaker-related subfamily, member 7 | Plasma Membrane | ion channel |
| KCNAB1 | potassium voltage-gated channel, shaker-related subfamily, beta member 1 | Plasma Membrane | ion channel |
| KCNB2 | potassium voltage-gated channel, Shab-related subfamily, member 2 | Plasma Membrane | ion channel |
| KCNC1 | potassium voltage-gated channel, Shaw-related subfamily, member 1 | Plasma Membrane | ion channel |
| KCNC2 | potassium voltage-gated channel, Shaw-related subfamily, member 2 | Plasma Membrane | ion channel |
| KCND3 | potassium voltage-gated channel, Shal-related subfamily, member 3 | Plasma Membrane | ion channel |
| KCNG4 | potassium voltage-gated channel, subfamily G, member 4 | Plasma Membrane | ion channel |
| KCNH7 | potassium voltage-gated channel, subfamily H (eag-related), member 7 | Plasma Membrane | ion channel |
| KCNIP2 | Kv channel interacting protein 2 | Cytoplasm | other |
| KCNJ5 | potassium inwardly-rectifying channel, subfamily J, member 5 | Plasma Membrane | ion channel |
| KCNK10 | potassium channel, subfamily K, member 10 | Plasma Membrane | ion channel |
| KCNK17 | potassium channel, subfamily K, member 17 | Plasma Membrane | ion channel |
| KCNQ1 | potassium voltage-gated channel, KQT-like subfamily, member 1 | Plasma Membrane | ion channel |
| KCNQ1DN | KCNQ1 downstream neighbor (non-protein coding) | unknown | other |
| KCP (includes EG: 296952) | kielin/chordin-like protein | Extracellular Space | other |
| KCTD19 | potassium channel tetramerisation domain containing 19 | unknown | other |
| KCTD4 | potassium channel tetramerisation domain containing 4 | unknown | ion channel |
| KIAA0355 | KIAA0355 | unknown | other |
| KIAA0825 | KIAA0825 | unknown | other |
| KIAA1045 | KIAA1045 | unknown | other |
| KIAA1109 | KIAA1109 | unknown | other |
| KIAA1239 | KIAA1239 | unknown | other |
| KIAA1407 | KIAA1407 | unknown | other |
| KIAA1462 | KIAA1462 | unknown | other |
| KIAA1522 | KIAA1522 | unknown | other |
| KIAA1683 | KIAA1683 | Cytoplasm | other |
| KIF6 | kinesin family member 6 | Nucleus | other |
| KIRREL3 | kin of IRRE like 3 (*Drosophila*) | Extracellular Space | other |
| KL | klotho | Extracellular Space | enzyme |
| KLF12 | Kruppel-like factor 12 | Nucleus | transcription regulator |
| KLF2 | Kruppel-like factor 2 (lung) | Nucleus | transcription regulator |
| KLHDC9 | kelch domain containing 9 | unknown | other |
| KLHL24 | kelch-like 24 (*Drosophila*) | unknown | other |
| KLHL4 | kelch-like 4 (*Drosophila*) | Cytoplasm | other |
| KLRB1 | killer cell lectin-like receptor subfamily B, member 1 | Plasma Membrane | transmembrane receptor |
| KRT2 | keratin 2 | Cytoplasm | other |
| KRT6B | keratin 6B | Cytoplasm | other |
| KRT72 | keratin 72 | unknown | other |
| KRT75 | keratin 75 | Cytoplasm | other |
| KRT82 | keratin 82 | Cytoplasm | other |
| KRTAP1-1 | keratin associated protein 1-1 | unknown | other |
| KRTAP1-3 | keratin associated protein 1-3 | unknown | other |
| KRTAP15-1 | keratin associated protein 15-1 | unknown | other |
| KRTAP4-7 | keratin associated protein 4-7 | unknown | other |

TABLE 1-continued

Rapamycin-sensitive genes (1051 genes)

| Symbol | Entrez Gene Name | Location | Type(s) |
|---|---|---|---|
| KRTAP9-2 | keratin associated protein 9-2 | unknown | other |
| LAIR2 | leukocyte-associated immunoglobulin-like receptor 2 | Plasma Membrane | other |
| LAMA1 | laminin, alpha 1 | Extracellular Space | other |
| LAYN | layilin | Plasma Membrane | other |
| LCE1E | late cornified envelope 1E | unknown | other |
| LECT1 | leukocyte cell derived chemotaxin 1 | Extracellular Space | other |
| LEF1 | lymphoid enhancer-binding factor 1 | Nucleus | transcription regulator |
| LEFTY1 | left-right determination factor 1 | Extracellular Space | growth factor |
| LEMD1 | LEM domain containing 1 | unknown | other |
| LEP | leptin | Extracellular Space | growth factor |
| LGALS13 | lectin, galactoside-binding, soluble, 13 | unknown | enzyme |
| LGALS2 | lectin, galactoside-binding, soluble, 2 | Cytoplasm | other |
| LGR5 | leucine-rich repeat containing G protein-coupled receptor 5 | Plasma Membrane | G-protein coupled receptor |
| LIFR | leukemia inhibitory factor receptor alpha | Plasma Membrane | transmembrane receptor |
| LILRB2 | leukocyte immunoglobulin-like receptor, subfamily B (with TM and ITIM domains), member 2 | Plasma Membrane | other |
| LINC00317 | long intergenic non-protein coding RNA 317 | unknown | other |
| LINC00477 | long intergenic non-protein coding RNA 477 | unknown | other |
| LIPF | lipase, gastric | Extracellular Space | enzyme |
| LOC100128098 | uncharacterized LOC100128098 | unknown | other |
| LOC100128108 | uncharacterized LOC100128108 | unknown | other |
| LOC100129406 | uncharacterized LOC100129406 | unknown | other |
| LOC100129476 | uncharacterized LOC100129476 | unknown | other |
| LOC100129775 | uncharacterized LOC100129775 | unknown | other |
| LOC100130278 | uncharacterized LOC100130278 | unknown | other |
| LOC100130776 | uncharacterized LOC100130776 | unknown | other |
| LOC100130815 | uncharacterized LOC100130815 | unknown | other |
| LOC100131176 | uncharacterized LOC100131176 | unknown | other |
| LOC100132116 | uncharacterized LOC100132116 | unknown | other |
| LOC100132363 | uncharacterized LOC100132363 | unknown | other |
| LOC100170939 | glucuronidase, beta pseudogene | unknown | other |
| LOC100190938 | uncharacterized LOC100190938 | unknown | other |
| LOC100190986 | uncharacterized LOC100190986 | unknown | other |
| LOC100288966/POTED | POTE ankyrin domain family, member D | Plasma Membrane | other |
| LOC120824/SPRYD5 | SPRY domain containing 5 | unknown | other |
| LOC283174 | uncharacterized LOC283174 | unknown | other |
| LOC283663 | uncharacterized LOC283663 | unknown | other |
| LOC283665 | uncharacterized LOC283665 | unknown | other |
| LOC284260 | uncharacterized LOC284260 | unknown | other |
| LOC284861 | uncharacterized LOC284861 | unknown | other |
| LOC286071 | uncharacterized LOC286071 | unknown | other |
| LOC286382 | uncharacterized LOC286382 | unknown | other |
| LOC339260 | uncharacterized LOC339260 | unknown | other |
| LOC389023 | uncharacterized LOC389023 | unknown | other |
| LOC389043 | uncharacterized LOC389043 | unknown | other |
| LOC390705 | protein phosphatase 2, regulatory subunit B", beta pseudogene | unknown | other |
| LOC400620 | uncharacterized LOC400620 | unknown | other |
| LOC400655 | uncharacterized LOC400655 | unknown | other |
| LOC401317 | uncharacterized LOC401317 | unknown | other |
| LOC441601 | septin 7 pseudogene | unknown | other |
| LOC474358 | uncharacterized BC042079 locus | unknown | other |
| LOC644192 | uncharacterized LOC644192 | unknown | other |
| LOC646471 | uncharacterized LOC646471 | unknown | other |
| LOC646627 | phospholipase inhibitor | unknown | other |
| LOC647107 | uncharacterized LOC647107 | unknown | other |
| LOC647946 | uncharacterized LOC647946 | unknown | other |
| LOC728093/LOC729915 | putative POM121-like protein 1 | unknown | other |
| LOC728323 | uncharacterized LOC728323 | unknown | other |
| LOC729121 | uncharacterized LOC729121 | unknown | other |
| LOC729970 | hCG2028352-like | unknown | other |
| LOX (includes EG: 16948) | lysyl oxidase | Extracellular Space | enzyme |
| LOXL3 | lysyl oxidase-like 3 | Extracellular Space | enzyme |
| LOXL4 | lysyl oxidase-like 4 | Extracellular Space | enzyme |
| LPIN2 | lipin 2 | Nucleus | phosphatase |
| LRCH2 | leucine-rich repeats and calponin homology (CH) domain containing 2 | unknown | other |
| LRP1 (includes EG: 16971) | low density lipoprotein receptor-related protein 1 | Plasma Membrane | transmembrane receptor |
| LRP1B | low density lipoprotein receptor-related protein 1B | Plasma Membrane | transmembrane receptor |

TABLE 1-continued

Rapamycin-sensitive genes (1051 genes)

| Symbol | Entrez Gene Name | Location | Type(s) |
|---|---|---|---|
| LRRC27 | leucine rich repeat containing 27 | unknown | other |
| LRRC37A3 (includes others) | leucine rich repeat containing 37, member A3 | unknown | other |
| LRRC48 | leucine rich repeat containing 48 | Cytoplasm | other |
| LRRC71 | leucine rich repeat containing 71 | unknown | other |
| LRRCC1 | leucine rich repeat and coiled-coil domain containing 1 | Nucleus | transporter |
| LTBP1 | latent transforming growth factor beta binding protein 1 | Extracellular Space | other |
| LUM | lumican | Extracellular Space | other |
| LYPD2 | LY6/PLAUR domain containing 2 | unknown | other |
| LYPD6 | LY6/PLAUR domain containing 6 | Extracellular Space | other |
| MACF1 | microtubule-actin crosslinking factor 1 | Cytoplasm | enzyme |
| MAEL | maelstrom homolog (*Drosophila*) | Cytoplasm | other |
| MAL | mal, T-cell differentiation protein | Plasma Membrane | transporter |
| MAPK4 | mitogen-activated protein kinase 4 | Cytoplasm | kinase |
| MAPT | microtubule-associated protein tau | Cytoplasm | other |
| MARK1 | MAP/microtubule affinity-regulating kinase 1 | Cytoplasm | kinase |
| MARVELD3 | MARVEL domain containing 3 | unknown | other |
| MAS1 | MAS1 oncogene | Plasma Membrane | G-protein coupled receptor |
| MBD3L2 (includes others) | methyl-CpG binding domain protein 3-like 2 | unknown | other |
| MBP | myelin basic protein | Extracellular Space | other |
| MCHR2 | melanin-concentrating hormone receptor 2 | Plasma Membrane | G-protein coupled receptor |
| MCTP1 | multiple C2 domains, transmembrane 1 | unknown | other |
| MECOM | MDS1 and EVI1 complex locus | Nucleus | transcription regulator |
| MEG3 | maternally expressed 3 (non-protein coding) | unknown | other |
| METTL21A | methyltransferase like 21A | unknown | other |
| METTL7A | methyltransferase like 7A | unknown | other |
| MFAP5 | microfibrillar associated protein 5 | Extracellular Space | other |
| MGC24103 | uncharacterized MGC24103 | unknown | other |
| MGC39545 | uncharacterized LOC403312 | unknown | other |
| MGC70870 | C-terminal binding protein 2 pseudogene | unknown | other |
| MGEA5 | meningioma expressed antigen 5 (hyaluronidase) | Cytoplasm | enzyme |
| MIA2 | melanoma inhibitory activity 2 | Extracellular Space | other |
| MIER1 | mesoderm induction early response 1 homolog (*Xenopus laevis*) | Nucleus | other |
| MIR7-3HG | MIR7-3 host gene (non-protein coding) | unknown | other |
| MIS18BP1 | MIS18 binding protein 1 | Nucleus | other |
| MLF1 | myeloid leukemia factor 1 | Nucleus | other |
| MLL | myeloid/lymphoid or mixed-lineage leukemia (trithorax homolog, *Drosophila*) | Nucleus | transcription regulator |
| MLLT4 | myeloid/lymphoid or mixed-lineage leukemia (trithorax homolog, *Drosophila*); translocated to, 4 | Nucleus | other |
| MME | membrane metallo-endopeptidase | Plasma Membrane | peptidase |
| MMP12 | matrix metallopeptidase 12 (macrophage elastase) | Extracellular Space | peptidase |
| MMP16 | matrix metallopeptidase 16 (membrane-inserted) | Extracellular Space | peptidase |
| MMP2 | matrix metallopeptidase 2 (gelatinase A, 72 kDa gelatinase, 72 kDa type IV collagenase) | Extracellular Space | peptidase |
| MMP8 | matrix metallopeptidase 8 (neutrophil collagenase) | Extracellular Space | peptidase |
| MMP9 | matrix metallopeptidase 9 (gelatinase B, 92 kDa gelatinase, 92 kDa type IV collagenase) | Extracellular Space | peptidase |
| MNT | MAX binding protein | Nucleus | transcription regulator |
| MORN5 | MORN repeat containing 5 | unknown | other |
| MOXD1 | monooxygenase, DBH-like 1 | Cytoplasm | enzyme |
| MPP4 | membrane protein, palmitoylated 4 (MAGUK p55 subfamily member 4) | Cytoplasm | kinase |
| MPPED2 | metallophosphoesterase domain containing 2 | unknown | other |
| MRO | maestro | Nucleus | other |
| MSMB | microseminoprotein, beta- | Extracellular Space | other |
| MTHFR | methylenetetrahydrofolate reductase (NAD(P)H) | Cytoplasm | enzyme |
| MTL5 | metallothionein-like 5, testis-specific (tesmin) | Cytoplasm | other |
| MTMR7 | myotubularin related protein 7 | Cytoplasm | phosphatase |
| MUC17 | mucin 17, cell surface associated | Plasma Membrane | other |
| MXI1 | MAX interactor 1 | Nucleus | transcription regulator |
| MYCL1 | v-myc myelocytomatosis viral oncogene homolog 1, lung carcinoma derived (avian) | Nucleus | transcription regulator |
| MYF6 | myogenic factor 6 (herculin) | Nucleus | transcription regulator |
| MYO16 | myosin XVI | Cytoplasm | other |
| MYO3B | myosin IIIB | unknown | kinase |

TABLE 1-continued

Rapamycin-sensitive genes (1051 genes)

| Symbol | Entrez Gene Name | Location | Type(s) |
|---|---|---|---|
| MYOM1 | myomesin 1, 185 kDa | Cytoplasm | other |
| MYOZ1 | myozenin 1 | Cytoplasm | other |
| MYPN | myopalladin | Cytoplasm | other |
| N4BP2L1 | NEDD4 binding protein 2-like 1 | unknown | other |
| NAG20 | NAG20 | unknown | other |
| NAV1 | neuron navigator 1 | Cytoplasm | enzyme |
| NAV2 | neuron navigator 2 | Nucleus | other |
| NBR1 | neighbor of BRCA1 gene 1 | Cytoplasm | other |
| NDRG2 | NDRG family member 2 | Cytoplasm | other |
| NECAB2 | N-terminal EF-hand calcium binding protein 2 | Cytoplasm | other |
| NEGR1 | neuronal growth regulator 1 | Extracellular Space | other |
| NEUROD4 | neuronal differentiation 4 | Nucleus | other |
| NEXN-AS1 | NEXN antisense RNA 1 (non-protein coding) | unknown | other |
| NFIB | nuclear factor I/B | Nucleus | transcription regulator |
| NIPBL | Nipped-B homolog (*Drosophila*) | Nucleus | transcription regulator |
| NKX3-2 | NK3 homeobox 2 | Nucleus | transcription regulator |
| NLRP13 | NLR family, pyrin domain containing 13 | unknown | other |
| NMNAT2 | nicotinamide nucleotide adenylyltransferase 2 | Cytoplasm | enzyme |
| NMU | neuromedin U | Extracellular Space | other |
| NOTCH2NL | notch 2 N-terminal like | unknown | other |
| NOX1 | NADPH oxidase 1 | Cytoplasm | ion channel |
| NPTX1 | neuronal pentraxin I | Extracellular Space | other |
| NR2F2 | nuclear receptor subfamily 2, group F, member 2 | Nucleus | ligand-dependent nuclear receptor |
| NR4A1 | nuclear receptor subfamily 4, group A, member 1 | Nucleus | ligand-dependent nuclear receptor |
| NR4A2 | nuclear receptor subfamily 4, group A, member 2 | Nucleus | ligand-dependent nuclear receptor |
| NRG2 | neuregulin 2 | Extracellular Space | growth factor |
| NRIP2 | nuclear receptor interacting protein 2 | Nucleus | transcription regulator |
| NRXN3 | neurexin 3 | Plasma Membrane | transporter |
| NSUN7 | NOP2/Sun domain family, member 7 | unknown | other |
| NTN4 | netrin 4 | Extracellular Space | other |
| NTSR1 | neurotensin receptor 1 (high affinity) | Plasma Membrane | G-protein coupled receptor |
| NUDT9P1 | nudix (nucleoside diphosphate linked moiety X)-type motif 9 pseudogene 1 | unknown | other |
| NUP210P1 | nucleoporin 210 kDa pseudogene 1 | unknown | other |
| NYAP1 | neuronal tyrosine-phosphorylated phosphoinositide-3-kinase adaptor 1 | unknown | other |
| OCA2 (includes EG: 18431) | oculocutaneous albinism II | Plasma Membrane | transporter |
| ODF1 | outer dense fiber of sperm tails 1 | Cytoplasm | other |
| OGN | osteoglycin | Extracellular Space | growth factor |
| OIT3 | oncoprotein induced transcript 3 | Nucleus | other |
| OLFML2A | olfactomedin-like 2A | Extracellular Space | other |
| OLIG2 | oligodendrocyte lineage transcription factor 2 | Nucleus | transcription regulator |
| OPRM1 | opioid receptor, mu 1 | Plasma Membrane | G-protein coupled receptor |
| OR10J1 | olfactory receptor, family 10, subfamily J, member 1 | Plasma Membrane | G-protein coupled receptor |
| OR10T2 | olfactory receptor, family 10, subfamily T, member 2 | Plasma Membrane | other |
| OR1E1 | olfactory receptor, family 1, subfamily E, member 1 | Plasma Membrane | G-protein coupled receptor |
| OR2C3 | olfactory receptor, family 2, subfamily C, member 3 | Plasma Membrane | other |
| OR2L13 | olfactory receptor, family 2, subfamily L, member 13 | Plasma Membrane | G-protein coupled receptor |
| OR2S2 | olfactory receptor, family 2, subfamily S, member 2 | Plasma Membrane | G-protein coupled receptor |

TABLE 1-continued

Rapamycin-sensitive genes (1051 genes)

| Symbol | Entrez Gene Name | Location | Type(s) |
| --- | --- | --- | --- |
| OR2V2 | olfactory receptor, family 2, subfamily V, member 2 | Plasma Membrane | G-protein coupled receptor |
| OR4N4 | olfactory receptor, family 4, subfamily N, member 4 | Plasma Membrane | G-protein coupled receptor |
| OR51E1 | olfactory receptor, family 51, subfamily E, member 1 | Plasma Membrane | G-protein coupled receptor |
| OR51E2 | olfactory receptor, family 51, subfamily E, member 2 | Plasma Membrane | G-protein coupled receptor |
| OR51Q1 | olfactory receptor, family 51, subfamily Q, member 1 | Plasma Membrane | G-protein coupled receptor |
| OR52B2 | olfactory receptor, family 52, subfamily B, member 2 | Plasma Membrane | G-protein coupled receptor |
| OR5AK2 | olfactory receptor, family 5, subfamily AK, member 2 | Plasma Membrane | G-protein coupled receptor |
| OSBPL2 | oxysterol binding protein-like 2 | Cytoplasm | other |
| OSTalpha | organic solute transporter alpha | Plasma Membrane | transporter |
| OTX1 | orthodenticle homeobox 1 | Nucleus | transcription regulator |
| OVOL1 | ovo-like 1(*Drosophila*) | Nucleus | transcription regulator |
| P2RY13 | purinergic receptor P2Y, G-protein coupled, 13 | Plasma Membrane | G-protein coupled receptor |
| P2RY14 | purinergic receptor P2Y, G-protein coupled, 14 | Plasma Membrane | G-protein coupled receptor |
| PABPC5 | poly(A) binding protein, cytoplasmic 5 | Cytoplasm | other |
| PAOX | polyamine oxidase (exo-N4-amino) | Cytoplasm | enzyme |
| PARVA | parvin, alpha | Cytoplasm | other |
| PASD1 | PAS domain containing 1 | Nucleus | other |
| PAX3 | paired box 3 | Nucleus | transcription regulator |
| PCDH11X/PCDH11Y | protocadherin 11 Y-linked | Plasma Membrane | other |
| PCDH18 | protocadherin 18 | Extracellular Space | other |
| PCDH7 | protocadherin 7 | Plasma Membrane | other |
| PCDHB10 | protocadherin beta 10 | Plasma Membrane | other |
| PCDHB5 | protocadherin beta 5 | Plasma Membrane | other |
| PCDHGA9 | protocadherin gamma subfamily A, 9 | unknown | other |
| PCDHGB8P | protocadherin gamma subfamily B, 8 pseudogene | unknown | other |
| PCMTD2 | protein-L-isoaspartate (D-aspartate) O-methyltransferase domain containing 2 | Cytoplasm | enzyme |
| PCNXL2 | pecanex-like 2 (*Drosophila*) | unknown | other |
| PCSK2 | proprotein convertase subtilisin/kexin type 2 | Extracellular Space | peptidase |
| PDC | phosducin | Cytoplasm | other |
| PDCD4 | programmed cell death 4 (neoplastic transformation inhibitor) | Nucleus | other |
| PDE1A | phosphodiesterase 1A, calmodulin-dependent | Cytoplasm | enzyme |
| PDE4C | phosphodiesterase 4C, cAMP-specific | Cytoplasm | enzyme |
| PDE4DIP | phosphodiesterase 4D interacting protein | Cytoplasm | enzyme |
| PDE6A | phosphodiesterase 6A, cGMP-specific, rod, alpha | Plasma Membrane | enzyme |
| PDE8B | phosphodiesterase 8B | Cytoplasm | enzyme |
| PDK4 | pyruvate dehydrogenase kinase, isozyme 4 | Cytoplasm | kinase |
| PDLIM3 | PDZ and LIM domain 3 | Cytoplasm | other |
| PDZD9 | PDZ domain containing 9 | unknown | other |
| PDZRN4 | PDZ domain containing ring finger 4 | unknown | other |
| PES1 | pescadillo ribosomal biogenesis factor 1 | Nucleus | other |
| PEX5L | peroxisomal biogenesis factor 5-like | Cytoplasm | ion channel |
| PHACTR1 | phosphatase and actin regulator 1 | Cytoplasm | other |
| PHF12 | PHD finger protein 12 | Nucleus | transcription regulator |
| PHLDA3 | pleckstrin homology-like domain, family A, member 3 | Plasma Membrane | other |
| PHLDB2 | pleckstrin homology-like domain, family B, member 2 | Cytoplasm | other |
| PHYHD1 | phytanoyl-CoA dioxygenase domain containing 1 | unknown | other |
| PHYHIPL | phytanoyl-CoA 2-hydroxylase interacting protein-like | Cytoplasm | other |
| PIM1 | pim-1 oncogene | Cytoplasm | kinase |
| PIP | prolactin-induced protein | Extracellular Space | other |
| PITPNM2 | phosphatidylinositol transfer protein, membrane-associated 2 | Cytoplasm | enzyme |
| PKD1L1 | polycystic kidney disease 1 like 1 | Extracellular Space | other |

TABLE 1-continued

Rapamycin-sensitive genes (1051 genes)

| Symbol | Entrez Gene Name | Location | Type(s) |
|---|---|---|---|
| PKHD1 | polycystic kidney and hepatic disease 1 (autosomal recessive) | Plasma Membrane | other |
| PKP1 | plakophilin 1 (ectodermal dysplasia/skin fragility syndrome) | Plasma Membrane | other |
| PLA2R1 | phospholipase A2 receptor 1, 180 kDa | Plasma Membrane | transmembrane receptor |
| PLAT | plasminogen activator, tissue | Extracellular Space | peptidase |
| PLB1 (includes EG: 151056) | phospholipase B1 | Cytoplasm | enzyme |
| PLCD4 | phospholipase C, delta 4 | Cytoplasm | enzyme |
| PLCH1 | phospholipase C, eta 1 | Cytoplasm | enzyme |
| PLCZ1 | phospholipase C, zeta 1 | unknown | enzyme |
| PLD1 | phospholipase D1, phosphatidylcholine-specific | Cytoplasm | enzyme |
| PLD3 | phospholipase D family, member 3 | Cytoplasm | enzyme |
| PLEKHA6 | pleckstrin homology domain containing, family A member 6 | unknown | other |
| PLEKHH2 | pleckstrin homology domain containing, family H (with MyTH4 domain) member 2 | Cytoplasm | other |
| PLGLB1/PLGLB2 | plasminogen-like B2 | Extracellular Space | peptidase |
| PLN | phospholamban | Cytoplasm | other |
| PLSCR2 | phospholipid scramblase 2 | unknown | other |
| PLSCR4 | phospholipid scramblase 4 | Plasma Membrane | enzyme |
| PM20D1 | peptidase M20 domain containing 1 | unknown | peptidase |
| PMCH | pro-melanin-concentrating hormone | Extracellular Space | other |
| PMCHL1 | pro-melanin-concentrating hormone-like 1, pseudogene | Extracellular Space | other |
| PNLIP | pancreatic lipase | Extracellular Space | enzyme |
| PNPLA1 | patatin-like phospholipase domain containing 1 | unknown | enzyme |
| PNRC1 | proline-rich nuclear receptor coactivator 1 | Nucleus | other |
| POLK | polymerase (DNA directed) kappa | Nucleus | enzyme |
| POLR2M | polymerase (RNA) II (DNA directed) polypeptide M | Nucleus | other |
| PON3 | paraoxonase 3 | Extracellular Space | enzyme |
| POTEE/POTEF | POTE ankyrin domain family, member F | unknown | other |
| POU4F2 | POU class 4 homeobox 2 | Nucleus | transcription regulator |
| PPAPDC1A | phosphatidic acid phosphatase type 2 domain containing 1A | unknown | phosphatase |
| PPIC | peptidylprolyl isomerase C (cyclophilin C) | Cytoplasm | enzyme |
| PRICKLE2 | prickle homolog 2 (*Drosophila*) | Nucleus | other |
| PRKAA2 | protein kinase, AMP-activated, alpha 2 catalytic subunit | Cytoplasm | kinase |
| PRKG1 | protein kinase, cGMP-dependent, type I | Cytoplasm | kinase |
| PRODH2 | proline dehydrogenase (oxidase) 2 | Cytoplasm | enzyme |
| PRR16 | proline rich 16 | unknown | other |
| PRSS23 | protease, serine, 23 | Extracellular Space | peptidase |
| PSORS1C1 | psoriasis susceptibility 1 candidate 1 | unknown | other |
| PTCH1 | patched 1 | Plasma Membrane | transmembrane receptor |
| PTGER3 | prostaglandin E receptor 3 (subtype EP3) | Plasma Membrane | G-protein coupled receptor |
| PTGS2 | prostaglandin-endoperoxide synthase 2 (prostaglandin G/H synthase and cyclooxygenase) | Cytoplasm | enzyme |
| PTPRC | protein tyrosine phosphatase, receptor type, C | Plasma Membrane | phosphatase |
| PTPRZ1 | protein tyrosine phosphatase, receptor-type, Z polypeptide 1 | Plasma Membrane | phosphatase |
| PYCR1 | pyrroline-5-carboxylate reductase 1 | Cytoplasm | enzyme |
| PZP | pregnancy-zone protein | Extracellular Space | other |
| RAB37 | RAB37, member RAS oncogene family | Cytoplasm | enzyme |
| RAB39A | RAB39A, member RAS oncogene family | Cytoplasm | enzyme |
| RAB3C (includes EG: 115827) | RAB3C, member RAS oncogene family | Cytoplasm | enzyme |
| RAET1E | retinoic acid early transcript 1E | Plasma Membrane | other |
| RAG1 | recombination activating gene 1 | Nucleus | enzyme |
| RAMP1 | receptor (G protein-coupled) activity modifying protein 1 | Plasma Membrane | transporter |
| RAVER2 | ribonucleoprotein, PTB-binding 2 | Nucleus | other |
| RBMY1A1 (includes others) | RNA binding motif protein, Y-linked, family 1, member A1 | Nucleus | other |
| RBPMS2 | RNA binding protein with multiple splicing 2 | unknown | other |
| RERGL | RERG/RAS-like | unknown | other |
| REST | RE1-silencing transcription factor | Nucleus | transcription regulator |
| RET | ret proto-oncogene | Plasma Membrane | kinase |
| REXO1L1 (includes others) | REX1, RNA exonuclease 1 homolog (*S. cerevisiae*)-like 1 | unknown | enzyme |

TABLE 1-continued

Rapamycin-sensitive genes (1051 genes)

| Symbol | Entrez Gene Name | Location | Type(s) |
| --- | --- | --- | --- |
| RGNEF | 190 kDa guanine nucleotide exchange factor | Cytoplasm | other |
| RHO | rhodopsin | Plasma Membrane | G-protein coupled receptor |
| RHOT1 | ras homolog family member T1 | Cytoplasm | enzyme |
| RIMBP3 (includes others) | RIMS binding protein 3 | Nucleus | other |
| RIMS2 | regulating synaptic membrane exocytosis 2 | unknown | other |
| RIN2 | Ras and Rab interactor 2 | Cytoplasm | other |
| RIT2 | Ras-like without CAAX 2 | Plasma Membrane | enzyme |
| RMI2 | RMI2, RecQ mediated genome instability 2, homolog (*S. cerevisiae*) | unknown | other |
| RND3 | Rho family GTPase 3 | Cytoplasm | enzyme |
| RNF125 | ring finger protein 125, E3 ubiquitin protein ligase | unknown | other |
| RNF128 | ring finger protein 128, E3 ubiquitin protein ligase | Cytoplasm | enzyme |
| RNF133 | ring finger protein 133 | Cytoplasm | other |
| RNF175 | ring finger protein 175 | unknown | other |
| RNF8 | ring finger protein 8, E3 ubiquitin protein ligase | Nucleus | enzyme |
| RORB | RAR-related orphan receptor B | Nucleus | ligand-dependent nuclear receptor |
| RPL32P3 | ribosomal protein L32 pseudogene 3 | unknown | other |
| RPS6KB1 | ribosomal protein S6 kinase, 70 kDa, polypeptide 1 | Cytoplasm | kinase |
| RRAD | Ras-related associated with diabetes | Cytoplasm | enzyme |
| RUFY2 | RUN and FYVE domain containing 2 | Nucleus | other |
| RUNX1T1 | runt-related transcription factor 1; translocated to, 1 (cyclin D-related) | Nucleus | transcription regulator |
| RUNX2 | runt-related transcription factor 2 | Nucleus | transcription regulator |
| SALL3 | sal-like 3 (*Drosophila*) | Nucleus | other |
| SCARNA17 | small Cajal body-specific RNA 17 | unknown | other |
| SCGN | secretagogin, EF-hand calcium binding protein | Cytoplasm | other |
| SCN3B | sodium channel, voltage-gated, type III, beta subunit | Plasma Membrane | ion channel |
| SCN8A | sodium channel, voltage gated, type VIII, alpha subunit | Plasma Membrane | ion channel |
| SEMA4C | sema domain, immunoglobulin domain (Ig), transmembrane domain (TM) and short cytoplasmic domain, (semaphorin) 4C | Plasma Membrane | other |
| SEMA5A | sema domain, seven thrombospondin repeats (type 1 and type 1-like), transmembrane domain (TM) and short cytoplasmic domain, (semaphorin) 5A | Plasma Membrane | transmembrane receptor |
| SEMA6A | sema domain, transmembrane domain (TM), and cytoplasmic domain, (semaphorin) 6A | Plasma Membrane | other |
| SEMG2 | semenogelin II | Extracellular Space | other |
| SERPINA10 | serpin peptidase inhibitor, clade A (alpha-1 antiproteinase, antitrypsin), member 10 | Extracellular Space | other |
| SERPINB3 | serpin peptidase inhibitor, clade B (ovalbumin), member 3 | Extracellular Space | other |
| SERPINB4 | serpin peptidase inhibitor, clade B (ovalbumin), member 4 | Cytoplasm | other |
| SERPIND1 | serpin peptidase inhibitor, clade D (heparin cofactor), member 1 | Extracellular Space | other |
| SERPINE1 | serpin peptidase inhibitor, clade E (nexin, plasminogen activator inhibitor type 1), member 1 | Extracellular Space | other |
| SERTAD4 | SERTA domain containing 4 | unknown | other |
| SGCD | sarcoglycan, delta (35 kDa dystrophin-associated glycoprotein) | Cytoplasm | other |
| SGCZ | sarcoglycan, zeta | Plasma Membrane | other |
| SGTA | small glutamine-rich tetratricopeptide repeat (TPR)-containing, alpha | Cytoplasm | other |
| SH3PXD2A | SH3 and PX domains 2A | Cytoplasm | other |
| SHANK3 | SH3 and multiple ankyrin repeat domains 3 | Cytoplasm | transcription regulator |
| SHROOM2 | shroom family member 2 | Plasma Membrane | ion channel |
| SHROOM4 | shroom family member 4 | Plasma Membrane | other |
| SIGLEC1 | sialic acid binding Ig-like lectin 1, sialoadhesin | Plasma Membrane | other |
| SIM2 | single-minded homolog 2 (*Drosophila*) | Nucleus | transcription regulator |
| SLC13A1 | solute carrier family 13 (sodium/sulfate symporters), member 1 | Plasma Membrane | transporter |
| SLC15A1 | solute carrier family 15 (oligopeptide transporter), member 1 | Plasma Membrane | transporter |
| SLC16A5 | solute carrier family 16, member 5 (monocarboxylic acid transporter 6) | Plasma Membrane | transporter |

TABLE 1-continued

Rapamycin-sensitive genes (1051 genes)

| Symbol | Entrez Gene Name | Location | Type(s) |
|---|---|---|---|
| SLC18A1 | solute carrier family 18 (vesicular monoamine), member 1 | Plasma Membrane | transporter |
| SLC18A3 | solute carrier family 18 (vesicular acetylcholine), member 3 | Plasma Membrane | transporter |
| SLC19A3 | solute carrier family 19, member 3 | Plasma Membrane | transporter |
| SLC22A18 | solute carrier family 22, member 18 | Plasma Membrane | transporter |
| SLC22A9 | solute carrier family 22 (organic anion transporter), member 9 | Plasma Membrane | transporter |
| SLC25A27 | solute carrier family 25, member 27 | Cytoplasm | transporter |
| SLC25A36 | solute carrier family 25, member 36 | Cytoplasm | transporter |
| SLC35F3 | solute carrier family 35, member F3 | unknown | other |
| SLC38A3 | solute carrier family 38, member 3 | Plasma Membrane | transporter |
| SLC46A2 | solute carrier family 46, member 2 | Plasma Membrane | transporter |
| SLC4A2 | solute carrier family 4, anion exchanger, member 2 (erythrocyte membrane protein band 3-like 1) | Plasma Membrane | transporter |
| SLC6A1 | solute carrier family 6 (neurotransmitter transporter, GABA), member 1 | Plasma Membrane | transporter |
| SLC6A11 | solute carrier family 6 (neurotransmitter transporter, GABA), member 11 | Plasma Membrane | transporter |
| SLC6A15 | solute carrier family 6 (neutral amino acid transporter), member 15 | Plasma Membrane | transporter |
| SLC6A19 | solute carrier family 6 (neutral amino acid transporter), member 19 | Plasma Membrane | transporter |
| SLC9B1 | solute carrier family 9, subfamily B (NHA1, cation proton antiporter 1), member 1 | Plasma Membrane | other |
| SLCO1A2 | solute carrier organic anion transporter family, member 1A2 | Plasma Membrane | transporter |
| SLFN5 | schlafen family member 5 | Nucleus | enzyme |
| SLITRK1 | SLIT and NTRK-like family, member 1 | unknown | other |
| SLITRK5 | SLIT and NTRK-like family, member 5 | unknown | other |
| SMA4 | glucuronidase, beta pseudogene | unknown | other |
| SMAD3 | SMAD family member 3 | Nucleus | transcription regulator |
| SMG1 | smg-1 homolog, phosphatidylinositol 3-kinase-related kinase (*C. elegans*) | Cytoplasm | kinase |
| SMOC1 | SPARC related modular calcium binding 1 | Extracellular Space | other |
| SNTB1 | syntrophin, beta 1 (dystrophin-associated protein A1, 59 kDa, basic component 1) | Plasma Membrane | other |
| SOCS2 | suppressor of cytokine signaling 2 | Cytoplasm | other |
| SORBS2 | sorbin and SH3 domain containing 2 | Plasma Membrane | other |
| SOX11 | SRY (sex determining region Y)-box 11 | Nucleus | transcription regulator |
| SOX21 | SRY (sex determining region Y)-box 21 | Nucleus | transcription regulator |
| SOX7 | SRY (sex determining region Y)-box 7 | Nucleus | transcription regulator |
| SP100 | SP100 nuclear antigen | Nucleus | transcription regulator |
| SPATA17 | spermatogenesis associated 17 | unknown | other |
| SPDYA | speedy homolog A (*Xenopus laevis*) | Nucleus | other |
| SPINLW1 | serine peptidase inhibitor-like, with Kunitz and WAP domains 1 (eppin) | Extracellular Space | other |
| SPOCK1 | sparc/osteonectin, cwcv and kazal-like domains proteoglycan (testican) 1 | Extracellular Space | other |
| SPP1 (includes EG: 20750) | secreted phosphoprotein 1 | Extracellular Space | cytokine |
| SPRED2 | sprouty-related, EVH1 domain containing 2 | Extracellular Space | cytokine |
| SPSB3 | splA/ryanodine receptor domain and SOCS box containing 3 | unknown | other |
| SPTB | spectrin, beta, erythrocytic | Plasma Membrane | other |
| SSBP1 | single-stranded DNA binding protein 1 | Cytoplasm | other |
| SSPO | SCO-spondin homolog (*Bos taurus*) | Cytoplasm | other |
| SSTR1 | somatostatin receptor 1 | Plasma Membrane | G-protein coupled receptor |
| SSX4/SSX4B | synovial sarcoma, X breakpoint 4 | Nucleus | other |
| SSX8 | synovial sarcoma, X breakpoint 8 | unknown | other |
| ST3GAL6 | ST3 beta-galactoside alpha-2,3-sialyltransferase 6 | Cytoplasm | enzyme |
| ST6GAL2 | ST6 beta-galactosamide alpha-2,6-sialyltranferase 2 | Cytoplasm | enzyme |
| ST6GALNAC2 | ST6 (alpha-N-acetyl-neuraminyl-2,3-beta-galactosyl-1,3)-N-acetylgalactosaminide alpha-2,6-sialyltransferase 2 | Cytoplasm | enzyme |
| STAG3L1 | stromal antigen 3-like 1 | unknown | other |
| STARD13 | StAR-related lipid transfer (START) domain containing 13 | Cytoplasm | other |
| STK31 | serine/threonine kinase 31 | Cytoplasm | kinase |

TABLE 1-continued

Rapamycin-sensitive genes (1051 genes)

| Symbol | Entrez Gene Name | Location | Type(s) |
|---|---|---|---|
| STK32B | serine/threonine kinase 32B | unknown | kinase |
| STMN1 | stathmin 1 | Cytoplasm | other |
| STMN3 | stathmin-like 3 | Nucleus | other |
| STON1-GTF2A1L | STON1-GTF2A1L readthrough | Nucleus | transcription regulator |
| STRA8 | stimulated by retinoic acid gene 8 homolog (mouse) | unknown | other |
| STS | steroid sulfatase (microsomal), isozyme S | Cytoplasm | enzyme |
| STX1B | syntaxin 1B | Plasma Membrane | ion channel |
| SYCE2 | synaptonemal complex central element protein 2 | Nucleus | other |
| SYCP3 | synaptonemal complex protein 3 | Nucleus | other |
| SYNE2 | spectrin repeat containing, nuclear envelope 2 | Nucleus | other |
| SYNPO2 | synaptopodin 2 | Cytoplasm | other |
| SYT14 | synaptotagmin XIV | unknown | transporter |
| TAC1 | tachykinin, precursor 1 | Extracellular Space | other |
| TACSTD2 | tumor-associated calcium signal transducer 2 | Plasma Membrane | other |
| tAKR | aldo-keto reductase, truncated | unknown | enzyme |
| TAOK1 | TAO kinase 1 | Cytoplasm | kinase |
| TAS2R42 | taste receptor, type 2, member 42 | unknown | other |
| TBX4 | T-box 4 | Nucleus | transcription regulator |
| TCEA3 | transcription elongation factor A (SII), 3 | Nucleus | transcription regulator |
| TCF12 | transcription factor 12 | Nucleus | transcription regulator |
| TCL1B | T-cell leukemia/lymphoma 1B | unknown | other |
| TCTEX1D1 | Tctex1 domain containing 1 | unknown | other |
| TDH | L-threonine dehydrogenase | Cytoplasm | enzyme |
| TEDDM1 | transmembrane epididymal protein 1 | unknown | other |
| TFAP2A | transcription factor AP-2 alpha (activating enhancer binding protein 2 alpha) | Nucleus | transcription regulator |
| TFAP2D | transcription factor AP-2 delta (activating enhancer binding protein 2 delta) | Nucleus | transcription regulator |
| TGFB3 | transforming growth factor, beta 3 | Extracellular Space | growth factor |
| TGM4 | transglutaminase 4 (prostate) | Extracellular Space | enzyme |
| THBS1 | thrombospondin 1 | Extracellular Space | other |
| THPO | thrombopoietin | Extracellular Space | cytokine |
| THRA (includes EG: 21833) | thyroid hormone receptor, alpha | Nucleus | ligand-dependent nuclear receptor |
| THSD7B | thrombospondin, type I, domain containing 7B | unknown | other |
| TIMM17B | translocase of inner mitochondrial membrane 17 homolog B (yeast) | Cytoplasm | transporter |
| TIMP2 (includes EG: 21858) | TIMP metallopeptidase inhibitor 2 | Extracellular Space | other |
| TINAG | tubulointerstitial nephritis antigen | Extracellular Space | peptidase |
| TLL1 | tolloid-like 1 | Extracellular Space | peptidase |
| TLR4 | toll-like receptor 4 | Plasma Membrane | transmembrane receptor |
| TLX1 | T-cell leukemia homeobox 1 | Nucleus | transcription regulator |
| TM4SF18 | transmembrane 4 L six family member 18 | unknown | other |
| TM4SF4 | transmembrane 4 L six family member 4 | Plasma Membrane | other |
| TMC3 | transmembrane channel-like 3 | unknown | other |
| TMEM192 | transmembrane protein 192 | unknown | other |
| TMEM37 | transmembrane protein 37 | Plasma Membrane | ion channel |
| TMEM45B | transmembrane protein 45B | Extracellular Space | other |
| TMEM47 | transmembrane protein 47 | Plasma Membrane | other |
| TMEM56 | transmembrane protein 56 | unknown | other |
| TMPRSS11A | transmembrane protease, serine 11A | unknown | peptidase |
| TNFAIP6 | tumor necrosis factor, alpha-induced protein 6 | Extracellular Space | other |
| TNFRSF10C | tumor necrosis factor receptor superfamily, member 10c, decoy without an intracellular domain | Plasma Membrane | transmembrane receptor |
| TNFRSF19 | tumor necrosis factor receptor superfamily, member 19 | Plasma Membrane | transmembrane receptor |
| TP73 | tumor protein p73 | Nucleus | transcription regulator |
| TPSD1 | tryptase delta 1 | Extracellular Space | peptidase |
| TRAM2 | translocation associated membrane protein 2 | unknown | other |
| TRIB1 | tribbles homolog 1 (*Drosophila*) | Cytoplasm | kinase |
| TRIM22 | tripartite motif containing 22 | Cytoplasm | transcription regulator |
| TRIM34 | tripartite motif containing 34 | Cytoplasm | other |
| TRIM49 | tripartite motif containing 49 | unknown | other |
| TRIM6 | tripartite motif containing 6 | Cytoplasm | other |
| TRIM72 | tripartite motif containing 72 | Cytoplasm | other |

TABLE 1-continued

Rapamycin-sensitive genes (1051 genes)

| Symbol | Entrez Gene Name | Location | Type(s) |
|---|---|---|---|
| TRIML1 | tripartite motif family-like 1 | unknown | other |
| TRIML2 | tripartite motif family-like 2 | unknown | other |
| TRPM1 | transient receptor potential cation channel, subfamily M, member 1 | Plasma Membrane | ion channel |
| TRPM6 | transient receptor potential cation channel, subfamily M, member 6 | Plasma Membrane | kinase |
| TRPV1 | transient receptor potential cation channel, subfamily V, member 1 | Plasma Membrane | ion channel |
| TSPAN11 | tetraspanin 11 | unknown | other |
| TSPAN12 | tetraspanin 12 | Plasma Membrane | transmembrane receptor |
| TSPAN8 | tetraspanin 8 | Plasma Membrane | other |
| TTC18 | tetratricopeptide repeat domain 18 | unknown | other |
| TTC23L | tetratricopeptide repeat domain 23-like | unknown | other |
| TTLL10 | tubulin tyrosine ligase-like family, member 10 | Extracellular Space | other |
| TTN (includes EG: 22138) | titin | Cytoplasm | kinase |
| TTPA | tocopherol (alpha) transfer protein | Cytoplasm | transporter |
| TTTY2 | testis-specific transcript, Y-linked 2 (non-protein coding) | Nucleus | other |
| TTTY8 | testis-specific transcript, Y-linked 8 (non-protein coding) | unknown | other |
| TUSC5 | tumor suppressor candidate 5 | unknown | other |
| TXNRD2 | thioredoxin reductase 2 | Cytoplasm | enzyme |
| UACA | uveal autoantigen with coiled-coil domains and ankyrin repeats | Cytoplasm | other |
| UBE2M | ubiquitin-conjugating enzyme E2M | Cytoplasm | enzyme |
| UBE2R2 | ubiquitin-conjugating enzyme E2R 2 | unknown | enzyme |
| UBN2 | ubinuclein 2 | Nucleus | other |
| UCA1 | urothelial cancer associated 1 (non-protein coding) | unknown | other |
| UCP1 | uncoupling protein 1 (mitochondrial, proton carrier) | Cytoplasm | transporter |
| UGT3A1 | UDP glycosyltransferase 3 family, polypeptide A1 | unknown | enzyme |
| ULK2 | unc-51-like kinase 2 (*C. elegans*) | Cytoplasm | kinase |
| UNC80 | unc-80 homolog (*C. elegans*) | unknown | other |
| USP11 | ubiquitin specific peptidase 11 | Nucleus | peptidase |
| USP38 | ubiquitin specific peptidase 38 | unknown | peptidase |
| UTS2 | urotensin 2 | Extracellular Space | other |
| UTS2D | urotensin 2 domain containing | Extracellular Space | other |
| VEZF1 | vascular endothelial zinc finger 1 | Nucleus | transcription regulator |
| VN1R4 | vomeronasal 1 receptor 4 | Plasma Membrane | G-protein coupled receptor |
| VPS54 (includes EG: 245944) | vacuolar protein sorting 54 homolog (*S. cerevisiae*) | unknown | other |
| VSNL1 | visinin-like 1 | Cytoplasm | other |
| VSTM4 | V-set and transmembrane domain containing 4 | unknown | other |
| VWA1 | von Willebrand factor A domain containing 1 | Extracellular Space | other |
| VWA3B | von Willebrand factor A domain containing 3B | unknown | other |
| WASF2 | WAS protein family, member 2 | Cytoplasm | other |
| WDFY3-AS2 | WDFY3 antisense RNA 2 (non-protein coding) | unknown | other |
| WDR17 | WD repeat domain 17 | unknown | other |
| WDR45 | WD repeat domain 45 | unknown | other |
| WDR49 | WD repeat domain 49 | unknown | other |
| WDR65 | WD repeat domain 65 | unknown | other |
| WDR72 | WD repeat domain 72 | unknown | other |
| WDR96 | WD repeat domain 96 | unknown | other |
| WFDC11 | WAP four-disulfide core domain 11 | Extracellular Space | other |
| WFDC5 | WAP four-disulfide core domain 5 | Extracellular Space | other |
| WFDC6 | WAP four-disulfide core domain 6 | Extracellular Space | other |
| WFDC9 | WAP four-disulfide core domain 9 | Extracellular Space | other |
| WLS | wntless homolog (*Drosophila*) | Cytoplasm | other |
| WNT8B | wingless-type MMTV integration site family, member 8B | Extracellular Space | other |
| WWP2 | WW domain containing E3 ubiquitin protein ligase 2 | Cytoplasm | enzyme |
| XIRP2 | xin actin-binding repeat containing 2 | unknown | other |
| XRN1 | 5'-3' exoribonuclease 1 | Cytoplasm | enzyme |
| XYLB | xylulokinase homolog (*H. influenzae*) | unknown | kinase |
| YPEL1 | yippee-like 1 (*Drosophila*) | Nucleus | enzyme |
| YPEL2 | yippee-like 2 (*Drosophila*) | Nucleus | other |
| YPEL5 | yippee-like 5 (*Drosophila*) | unknown | other |
| ZADH2 | zinc binding alcohol dehydrogenase domain containing 2 | Cytoplasm | enzyme |
| ZBTB10 | zinc finger and BTB domain containing 10 | Nucleus | other |
| ZBTB20 | zinc finger and BTB domain containing 20 | Nucleus | other |
| ZC3H6 | zinc finger CCCH-type containing 6 | unknown | other |

TABLE 1-continued

Rapamycin-sensitive genes (1051 genes)

| Symbol | Entrez Gene Name | Location | Type(s) |
|---|---|---|---|
| ZCCHC12 | zinc finger, CCHC domain containing 12 | unknown | other |
| ZDHHC15 | zinc finger, DHHC-type containing 15 | unknown | enzyme |
| ZFYVE16 | zinc finger, FYVE domain containing 16 | Nucleus | transporter |
| ZIC4 | Zic family member 4 | Nucleus | other |
| ZMAT1 | zinc finger, matrin-type 1 | Nucleus | other |
| ZNF292 | zinc finger protein 292 | Nucleus | transcription regulator |
| ZNF385B | zinc finger protein 385B | Nucleus | other |
| ZNF445 | zinc finger protein 445 | Nucleus | transcription regulator |
| ZNF45 | zinc finger protein 45 | Nucleus | transcription regulator |
| ZNF471 | zinc finger protein 471 | Nucleus | other |
| ZNF572 | zinc finger protein 572 | Nucleus | other |
| ZNF695 | zinc finger protein 695 | Nucleus | other |
| ZNF704 | zinc finger protein 704 | unknown | other |
| ZNF711 | zinc finger protein 711 | Nucleus | other |
| ZNF804A | zinc finger protein 804A | unknown | other |
| ZNF81 | zinc finger protein 81 | Nucleus | transcription regulator |
| ZSCAN4 | zinc finger and SCAN domain containing 4 | Nucleus | transcription regulator |

TABLE 2

Rapamycin-sensitive genes differentially regulated in brain of Alzheimer's disease patients with mild disease (112 known genes)

| Symbol | Entrez Gene Name | Location | Type(s) | Fold Change |
|---|---|---|---|---|
| ABTB1 | ankyrin repeat and BTB (POZ) domain containing 1 | Cytoplasm | translation regulator | 1.057 |
| ADAMTS2 | ADAM metallopeptidase with thrombospondin type 1 motif, 2 | Extracellular Space | peptidase | 1.083 |
| ADAMTSL5 | ADAMTS-like 5 | Extracellular Space | other | 1.088 |
| AHNAK2 | AHNAK nucleoprotein 2 | unknown | other | 1.056 |
| B4GALT6 | UDP-Gal: betaGlcNAc beta 1,4-galactosyltransferase, polypeptide 6 | Cytoplasm | enzyme | 1.022 |
| BARX2 | BARX homeobox 2 | Nucleus | transcription regulator | 1.077 |
| BMP7 | bone morphogenetic protein 7 | Extracellular Space | growth factor | 1.035 |
| BTNL9 | butyrophilin-like 9 | unknown | other | 1.056 |
| C17orf99 | chromosome 17 open reading frame 99 | unknown | other | 1.032 |
| C1orf127 | chromosome 1 open reading frame 127 | unknown | other | 1.074 |
| CACNA1D | calcium channel, voltage-dependent, L type, alpha 1D subunit | Plasma Membrane | ion channel | 1.063 |
| CARD14 | caspase recruitment domain family, member 14 | Cytoplasm | other | 1.034 |
| CC2D2A | coiled-coil and C2 domain containing 2A | unknown | other | 1.102 |
| CCL1 | chemokine (C-C motif) ligand 1 | Extracellular Space | cytokine | 1.066 |
| CCL11 | chemokine (C-C motif) ligand 11 | Extracellular Space | cytokine | 1.048 |
| CCL2 | chemokine (C-C motif) ligand 2 | Extracellular Space | cytokine | 1.061 |
| CCR1 | chemokine (C-C motif) receptor 1 | Plasma Membrane | G-protein coupled receptor | 1.034 |
| CD69 | CD69 molecule | Plasma Membrane | transmembrane receptor | 1.028 |
| CDKN2C | cyclin-dependent kinase inhibitor 2C (p18, inhibits CDK4) | Nucleus | transcription regulator | 1.056 |
| CEACAM1 (includes others) | carcinoembryonic antigen-related cell adhesion molecule 1 (biliary glycoprotein) | Plasma Membrane | transmembrane receptor | 1.079 |
| CEP68 | centrosomal protein 68 kDa | Cytoplasm | other | 1.036 |
| COL1A2 | collagen, type I, alpha 2 | Extracellular Space | other | 1.043 |
| CPXM2 | carboxypeptidase X (M14 family), member 2 | Extracellular Space | peptidase | 1.026 |
| CREB3L4 | cAMP responsive element binding protein 3-like 4 | Nucleus | transcription regulator | 1.064 |
| CRP | C-reactive protein, pentraxin-related | Extracellular Space | other | 1.104 |
| CTDSP1 | CTD (carboxy-terminal domain, RNA polymerase II, polypeptide A) small phosphatase 1 | Nucleus | phosphatase | 1.098 |
| DCAF12L1 | DDB1 and CUL4 associated factor 12-like 1 | unknown | other | 1.030 |
| DCD | dermcidin | Extracellular Space | other | 1.159 |
| DRP2 | dystrophin related protein 2 | Plasma Membrane | other | 1.043 |
| EBF2 | early B-cell factor 2 | Nucleus | other | 1.028 |
| ENTPD8 | ectonucleoside triphosphate diphosphohydrolase 8 | unknown | enzyme | 1.071 |
| FAM43B | family with sequence similarity 43, member B | unknown | other | 1.061 |
| FAM64A | family with sequence similarity 64, member A | Nucleus | other | 1.214 |
| FCGBP | Fc fragment of IgG binding protein | Extracellular Space | other | 1.057 |
| FGF11 | fibroblast growth factor 11 | Extracellular Space | growth factor | 1.169 |
| FJX1 | four jointed box 1 (Drosophila) | Extracellular Space | other | 1.123 |
| FLJ35946 | uncharacterized protein FLJ35946 | unknown | other | 1.148 |

TABLE 2-continued

Rapamycin-sensitive genes differentially regulated in brain of Alzheimer's disease patients with mild disease (112 known genes)

| Symbol | Entrez Gene Name | Location | Type(s) | Fold Change |
|---|---|---|---|---|
| FN3K | fructosamine 3 kinase | Cytoplasm | kinase | 1.258 |
| GLI2 | GLI family zinc finger 2 | Nucleus | transcription regulator | 1.032 |
| GLP1R | glucagon-like peptide 1 receptor | Plasma Membrane | G-protein coupled receptor | 1.031 |
| GLRA1 | glycine receptor, alpha 1 | Plasma Membrane | ion channel | 1.041 |
| GPR176 | G protein-coupled receptor 176 | Plasma Membrane | G-protein coupled receptor | 1.092 |
| HCAR3 | hydroxycarboxylic acid receptor 3 | Plasma Membrane | G-protein coupled receptor | 1.041 |
| HDAC5 | histone deacetylase 5 | Nucleus | transcription regulator | 1.112 |
| HHIPL1 | HHIP-like 1 | unknown | other | 1.057 |
| HMGCS2 | 3-hydroxy-3-methylglutaryl-CoA synthase 2 (mitochondrial) | Cytoplasm | enzyme | 1.044 |
| HOXD10 | homeobox D10 | Nucleus | transcription regulator | 1.024 |
| HYDIN | HYDIN, axonemal central pair apparatus protein | unknown | other | 1.077 |
| IL6 | interleukin 6 (interferon, beta 2) | Extracellular Space | cytokine | 1.034 |
| KLF2 | Kruppel-like factor 2 (lung) | Nucleus | transcription regulator | 1.084 |
| LECT1 | leukocyte cell derived chemotaxin 1 | Extracellular Space | other | 1.062 |
| LINC00473 | long intergenic non-protein coding RNA 473 | unknown | other | 1.097 |
| LOC100129775 | uncharacterized LOC100129775 | unknown | other | 1.047 |
| LOC100505890 | uncharacterized LOC100505890 | unknown | other | 1.025 |
| LOC100506206 | uncharacterized LOC100506206 | unknown | other | 1.192 |
| LOC100506236 | uncharacterized LOC100506236 | unknown | other | 1.126 |
| LOC100507492 | uncharacterized LOC100507492 | unknown | other | 1.086 |
| LOC100507520 | uncharacterized L0C100507520 | unknown | other | 1.495 |
| LOC285740 | uncharacterized LOC285740 | unknown | other | 1.027 |
| LOC389043 | uncharacterized LOC389043 | unknown | other | 1.330 |
| LOC400752 | uncharacterized LOC400752 | unknown | other | 1.115 |
| LOC401317 | uncharacterized LOC401317 | unknown | other | 1.034 |
| LOC728724 | hCG1814486 | unknown | other | 1.051 |
| LOXL4 | lysyl oxidase-like 4 | Extracellular Space | enzyme | 1.122 |
| LUM | lumican | Extracellular Space | other | 1.073 |
| LYPD2 | LY6/PLAUR domain containing 2 | unknown | other | 1.101 |
| MAPK4 | mitogen-activated protein kinase 4 | Cytoplasm | kinase | 1.103 |
| MFAP5 | microfibrillar associated protein 5 | Extracellular Space | other | 1.024 |
| MGC24103 | uncharacterized MGC24103 | unknown | other | 1.045 |
| MGC39545 | uncharacterized LOC403312 | unknown | other | 1.026 |
| MOXD1 | monooxygenase, DBH-like 1 | Cytoplasm | enzyme | 1.124 |
| MYF6 | myogenic factor 6 (herculin) | Nucleus | transcription regulator | 1.127 |
| NCKAP1 | NCK-associated protein 1 | Plasma Membrane | other | 1.043 |
| NR3C1 | nuclear receptor subfamily 3, group C, member 1 (glucocorticoid receptor) | Nucleus | ligand-dependent nuclear receptor | 1.058 |
| NTSR1 | neurotensin receptor 1 (high affinity) | Plasma Membrane | G-protein coupled receptor | 1.058 |
| OR52B2 | olfactory receptor, family 52, subfamily B, member 2 | Plasma Membrane | G-protein coupled receptor | 1.051 |
| OTOGL | otogelin-like | unknown | other | 1.039 |
| PAOX | polyamine oxidase (exo-N4-amino) | Cytoplasm | enzyme | 1.043 |
| PBX1 | pre-B-cell leukemia homeobox 1 | Nucleus | transcription regulator | 1.021 |
| PHLDA3 | pleckstrin homology-like domain, family A, member 3 | Plasma Membrane | other | 1.056 |
| PIM1 | pim-1 oncogene | Cytoplasm | kinase | 1.041 |
| PLD4 | phospholipase D family, member 4 | unknown | enzyme | 1.087 |
| POU4F2 | POU class 4 homeobox 2 | Nucleus | transcription regulator | 1.040 |
| PRKCH | protein kinase C, eta | Cytoplasm | kinase | 1.169 |
| PRODH2 | proline dehydrogenase (oxidase) 2 | Cytoplasm | enzyme | 1.056 |
| PVRL3 | poliovirus receptor-related 3 | Plasma Membrane | other | 1.064 |
| RELN | reelin | Extracellular Space | peptidase | 1.113 |
| RHO | rhodopsin | Plasma Membrane | G-protein coupled receptor | 1.024 |
| RHOT1 | ras homolog family member T1 | Cytoplasm | enzyme | 1.029 |
| RPS6KB2 | ribosomal protein S6 kinase, 70 kDa, polypeptide 2 | Cytoplasm | kinase | 1.077 |
| RUNX1T1 | runt-related transcription factor 1; translocated to, 1 (cyclin D-related) | Nucleus | transcription regulator | 1.053 |
| SEMA4C | sema domain, immunoglobulin domain (Ig), transmembrane domain (TM) and short cytoplasmic domain, (semaphorin) 4C | Plasma Membrane | other | 1.135 |
| SEMA5A | sema domain, seven thrombospondin repeats (type 1 and type 1-like), transmembrane domain (TM) and short cytoplasmic domain, (semaphorin) 5A | Plasma Membrane | transmembrane receptor | 1.092 |
| SERPIND1 | serpin peptidase inhibitor, clade D (heparin cofactor), member 1 | Extracellular Space | other | 1.030 |
| SERPINE1 | serpin peptidase inhibitor, clade E (nexin, plasminogen activator inhibitor type 1), member 1 | Extracellular Space | other | 1.091 |
| SHE | Src homology 2 domain containing E | Cytoplasm | other | 1.030 |
| SLC18A3 | solute carrier family 18 (vesicular acetylcholine), member 3 | Plasma Membrane | transporter | 1.056 |
| SLC22A18 | solute carrier family 22, member 18 | Plasma Membrane | transporter | 1.173 |

TABLE 2-continued

Rapamycin-sensitive genes differentially regulated in brain of Alzheimer's disease patients with mild disease (112 known genes)

| Symbol | Entrez Gene Name | Location | Type(s) | Fold Change |
|---|---|---|---|---|
| SLC22A7 | solute carrier family 22 (organic anion transporter), member 7 | Plasma Membrane | transporter | 1.077 |
| SLC38A3 | solute carrier family 38, member 3 | Plasma Membrane | transporter | 1.033 |
| SMAD3 | SMAD family member 3 | Nucleus | transcription regulator | 1.042 |
| STARD13 | StAR-related lipid transfer (START) domain containing 13 | Cytoplasm | other | 1.269 |
| TM4SF4 | transmembrane 4 L six family member 4 | Plasma Membrane | other | 1.024 |
| TNFRSF10C | tumor necrosis factor receptor superfamily, member 10c, decoy without an intracellular domain | Plasma Membrane | transmembrane receptor | 1.030 |
| TRIB1 | tribbles homolog 1 (*Drosophila*) | Cytoplasm | kinase | 1.041 |
| TRPV1 | transient receptor potential cation channel, subfamily V, member 1 | Plasma Membrane | ion channel | 1.037 |
| TTC18 | tetratricopeptide repeat domain 18 | unknown | other | 1.072 |
| UCA1 | urothelial cancer associated 1 (non-protein coding) | unknown | other | 1.041 |
| WFDC9 | WAP four-disulfide core domain 9 | Extracellular Space | other | 1.052 |
| XRN1 | 5'-3' exoribonuclease 1 | Cytoplasm | enzyme | 1.027 |
| ZADH2 | zinc binding alcohol dehydrogenase domain containing 2 | Cytoplasm | enzyme | 1.129 |
| ZBTB20 | zinc finger and BTB domain containing 20 | Nucleus | other | 1.044 |

TABLE 3

Rapamycin-sensitive genes differentially regulated in brain of Alzheimer's disease patients with advanced disease (178 known genes)

| Symbol | Entrez Gene Name | Location | Type(s) | Fold Change |
|---|---|---|---|---|
| ABLIM2 | actin binding LIM protein family, member 2 | Cytoplasm | other | 0.905 |
| ABTB1 | ankyrin repeat and BTB (POZ) domain containing 1 | Cytoplasm | translation regulator | 1.058 |
| ACSL6 | acyl-CoA synthetase long-chain family member 6 | Cytoplasm | enzyme | 0.937 |
| ACTRT1 | actin-related protein T1 | Cytoplasm | other | 1.025 |
| ACVR2B | activin A receptor, type IIB | Plasma Membrane | kinase | 1.038 |
| ADAMTS2 | ADAM metallopeptidase with thrombospondin type 1 motif, 2 | Extracellular Space | peptidase | 1.082 |
| ADAMTSL5 | ADAMTS-like 5 | Extracellular Space | other | 1.094 |
| AHNAK2 | AHNAK nucleoprotein 2 | unknown | other | 1.056 |
| ANKRD36BP2 | ankyrin repeat domain 36B pseudogene 2 | unknown | other | 0.913 |
| AP1S1 | adaptor-related protein complex 1, sigma 1 subunit | Cytoplasm | transporter | 0.955 |
| ATAD3A/ATAD3B | ATPase family, AAA domain containing 3A | Nucleus | other | 1.078 |
| ATF7IP | activating transcription factor 7 interacting protein | Nucleus | transcription regulator | 0.934 |
| ATRNL1 | attractin-like 1 | unknown | other | 0.865 |
| BARX2 | BARX homeobox 2 | Nucleus | transcription regulator | 1.080 |
| BCOR | BCL6 corepressor | Nucleus | transcription regulator | 1.032 |
| BMP7 | bone morphogenetic protein 7 | Extracellular Space | growth factor | 1.046 |
| BPI | bactericidal/permeability-increasing protein | Plasma Membrane | transporter | 1.036 |
| BTNL9 | butyrophilin-like 9 | unknown | other | 1.063 |
| C17orf99 | chromosome 17 open reading frame 99 | unknown | other | 1.039 |
| C18orf26 | chromosome 18 open reading frame 26 | unknown | other | 0.960 |
| C1orf127 | chromosome 1 open reading frame 127 | unknown | other | 1.087 |
| C3orf80 | chromosome 3 open reading frame 80 | unknown | other | 0.952 |
| CACNA1D | calcium channel, voltage-dependent, L type, alpha 1D subunit | Plasma Membrane | ion channel | 1.070 |
| CARD14 | caspase recruitment domain family, member 14 | Cytoplasm | other | 1.025 |
| CC2D2A | coiled-coil and C2 domain containing 2A | unknown | other | 1.098 |
| CCL1 | chemokine (C-C motif) ligand 1 | Extracellular Space | cytokine | 1.063 |
| CCL11 | chemokine (C-C motif) ligand 11 | Extracellular Space | cytokine | 1.039 |
| CCL2 | chemokine (C-C motif) ligand 2 | Extracellular Space | cytokine | 1.082 |
| CCNB2 | cyclin B2 | Cytoplasm | other | 1.073 |
| CCR1 | chemokine (C-C motif) receptor 1 | Plasma Membrane | G-protein coupled receptor | 1.032 |
| CEACAM1 (includes others) | carcinoembryonic antigen-related cell adhesion molecule 1 (biliary glycoprotein) | Plasma Membrane | transmembrane receptor | 1.081 |
| CEP68 | centrosomal protein 68 kDa | Cytoplasm | other | 1.040 |
| CLU | clusterin | Extracellular Space | other | 0.911 |
| CPLX2 | complexin 2 | Cytoplasm | other | 0.918 |
| CPXM2 | carboxypeptidase X (M14 family), member 2 | Extracellular Space | peptidase | 1.030 |
| CREB3L4 | cAMP responsive element binding protein 3-like 4 | Nucleus | transcription regulator | 1.054 |
| CRP | C-reactive protein, pentraxin-related | Extracellular Space | other | 1.111 |
| CTDSP1 | CTD (carboxy-terminal domain, RNA polymerase II, polypeptide A) small phosphatase 1 | Nucleus | phosphatase | 1.119 |
| CUX1 | cut-like homeobox 1 | Nucleus | transcription regulator | 0.969 |
| DCAF12L1 | DDB1 and CUL4 associated factor 12-like 1 | unknown | other | 1.038 |
| DCD | dermcidin | Extracellular Space | other | 1.152 |
| DCLK1 | doublecortin-like kinase 1 | Plasma Membrane | kinase | 0.939 |
| DLG2 | discs, large homolog 2 (*Drosophila*) | Plasma Membrane | kinase | 0.917 |

TABLE 3-continued

Rapamycin-sensitive genes differentially regulated in brain of Alzheimer's disease patients with advanced disease (178 known genes)

| Symbol | Entrez Gene Name | Location | Type(s) | Fold Change |
|---|---|---|---|---|
| DNAH6 | dynein, axonemal, heavy chain 6 | unknown | other | 0.957 |
| DRP2 | dystrophin related protein 2 | Plasma Membrane | other | 1.038 |
| DYNC2LI1 | dynein, cytoplasmic 2, light intermediate chain 1 | Cytoplasm | other | 0.946 |
| DZIP3 | DAZ interacting protein 3, zinc finger | Cytoplasm | enzyme | 0.905 |
| EBF2 | early B-cell factor 2 | Nucleus | other | 1.024 |
| EIF4E | eukaryotic translation initiation factor 4E | Cytoplasm | translation regulator | 0.920 |
| ELAVL4 | ELAV (embryonic lethal, abnormal vision, *Drosophila*)-like 4 (Hu antigen D) | Cytoplasm | other | 0.931 |
| ENTPD8 | ectonucleoside triphosphate diphosphohydrolase 8 | unknown | enzyme | 1.063 |
| FAM155A | family with sequence similarity 155, member A | unknown | other | 0.860 |
| FAM171B | family with sequence similarity 171, member B | unknown | other | 0.948 |
| FAM64A | family with sequence similarity 64, member A | Nucleus | other | 1.154 |
| FAT3 | FAT tumor suppressor homolog 3 (*Drosophila*) | unknown | other | 0.954 |
| FGF11 | fibroblast growth factor 11 | Extracellular Space | growth factor | 1.185 |
| FJX1 | four jointed box 1 (*Drosophila*) | Extracellular Space | other | 1.104 |
| FLJ35946 | uncharacterized protein FLJ35946 | unknown | other | 1.137 |
| FN3K | fructosamine 3 kinase | Cytoplasm | kinase | 1.269 |
| GABBR2 | gamma-aminobutyric acid (GABA) B receptor, 2 | Plasma Membrane | G-protein coupled receptor | 0.862 |
| GALNT10 | UDP-N-acetyl-alpha-D-galactosamine:polypeptide N-acetylgalactosaminyltransferase 10 (GalNAc-T10) | Cytoplasm | enzyme | 1.064 |
| GFAP | glial fibrillary acidic protein | Cytoplasm | other | 1.091 |
| GIGYF1 | GRB10 interacting GYF protein 1 | unknown | other | 1.042 |
| GLI2 | GLI family zinc finger 2 | Nucleus | transcription regulator | 1.033 |
| GLRA1 | glycine receptor, alpha 1 | Plasma Membrane | ion channel | 1.043 |
| GNG8 | guanine nucleotide binding protein (G protein), gamma 8 | Plasma Membrane | enzyme | 1.059 |
| GPM6A | glycoprotein M6A | Plasma Membrane | ion channel | 0.920 |
| GPR176 | G protein-coupled receptor 176 | Plasma Membrane | G-protein coupled receptor | 1.098 |
| GSG1L | GSG1-like | unknown | other | 1.025 |
| HCAR3 | hydroxycarboxylic acid receptor 3 | Plasma Membrane | G-protein coupled receptor | 1.053 |
| HDAC5 | histone deacetylase 5 | Nucleus | transcription regulator | 1.125 |
| HHIPL1 | HHIP-like 1 | unknown | other | 1.063 |
| HIST1H4A (includes others) | histone cluster 1, H4a | Nucleus | other | 0.894 |
| HMGCS2 | 3-hydroxy-3-methylglutaryl-CoA synthase 2 (mitochondrial) | Cytoplasm | enzyme | 1.034 |
| HOXD10 | homeobox D10 | Nucleus | transcription regulator | 1.038 |
| HYDIN | HYDIN, axonemal central pair apparatus protein | unknown | other | 1.090 |
| IL1RAPL1 | interleukin 1 receptor accessory protein-like 1 | Plasma Membrane | transmembrane receptor | 1.029 |
| IL6 | interleukin 6 (interferon, beta 2) | Extracellular Space | cytokine | 1.037 |
| IRS2 | insulin receptor substrate 2 | Cytoplasm | enzyme | 0.925 |
| IRS2 | insulin receptor substrate 2 | Cytoplasm | enzyme | 0.941 |
| IRX4 | iroquois homeobox 4 | Nucleus | transcription regulator | 1.032 |
| ITGBL1 | integrin, beta-like 1 (with EGF-like repeat domains) | unknown | other | 1.038 |
| KCNAB1 | potassium voltage-gated channel, shaker-related subfamily, beta member 1 | Plasma Membrane | ion channel | 0.936 |
| KCND2 | potassium voltage-gated channel, Shal-related subfamily, member 2 | Plasma Membrane | ion channel | 0.958 |
| KCNG4 | potassium voltage-gated channel, subfamily G, member 4 | Plasma Membrane | ion channel | 1.152 |
| KIAA1683 | KIAA1683 | Cytoplasm | other | 1.046 |
| KLF2 | Kruppel-like factor 2 (lung) | Nucleus | transcription regulator | 1.103 |
| KRTAP9-2 | keratin associated protein 9-2 | unknown | other | 1.022 |
| LECT1 | leukocyte cell derived chemotaxin 1 | Extracellular Space | other | 1.060 |
| LINC00473 | long intergenic non-protein coding RNA 473 | unknown | other | 1.085 |
| LOC100129775 | uncharacterized LOC100129775 | unknown | other | 1.051 |
| LOC100287803 | uncharacterized LOC100287803 | unknown | other | 0.854 |
| LOC100506206 | uncharacterized LOC100506206 | unknown | other | 1.199 |
| LOC100506236 | uncharacterized LOC100506236 | unknown | other | 1.127 |
| LOC100507492 | uncharacterized LOC100507492 | unknown | other | 1.080 |
| LOC100507520 | uncharacterized LOC100507520 | unknown | other | 1.497 |
| LOC285740 | uncharacterized LOC285740 | unknown | other | 1.024 |
| LOC389043 | uncharacterized LOC389043 | unknown | other | 1.255 |
| LOC400752 | uncharacterized LOC400752 | unknown | other | 1.113 |
| LOC401317 | uncharacterized LOC401317 | unknown | other | 1.037 |
| LOC728323 | uncharacterized LOC728323 | unknown | other | 0.921 |
| LOC728724 | hCG1814486 | unknown | other | 1.070 |
| LOXL4 | lysyl oxidase-like 4 | Extracellular Space | enzyme | 1.136 |
| LRRC71 | leucine rich repeat containing 71 | unknown | other | 1.052 |
| LUM | lumican | Extracellular Space | other | 1.069 |
| LYPD2 | LY6/PLAUR domain containing 2 | unknown | other | 1.102 |
| MAPK1 | mitogen-activated protein kinase 1 | Cytoplasm | kinase | 0.912 |
| MAPK4 | mitogen-activated protein kinase 4 | Cytoplasm | kinase | 1.100 |

TABLE 3-continued

Rapamycin-sensitive genes differentially regulated in brain of Alzheimer's disease patients with advanced disease (178 known genes)

| Symbol | Entrez Gene Name | Location | Type(s) | Fold Change |
|---|---|---|---|---|
| MBD3L2 (includes others) | methyl-CpG binding domain protein 3-like 2 | unknown | other | 1.025 |
| MCTP1 | multiple C2 domains, transmembrane 1 | unknown | other | 0.914 |
| MECOM | MDS1 and EVI1 complex locus | Nucleus | transcription regulator | 1.024 |
| MFAP5 | microfibrillar associated protein 5 | Extracellular Space | other | 1.026 |
| MGC24103 | uncharacterized MGC24103 | unknown | other | 1.050 |
| MMP16 | matrix metallopeptidase 16 (membrane-inserted) | Extracellular Space | peptidase | 0.928 |
| MOXD1 | monooxygenase, DBH-like 1 | Cytoplasm | enzyme | 1.103 |
| MYF6 | myogenic factor 6 (herculin) | Nucleus | transcription regulator | 1.136 |
| NAV2 | neuron navigator 2 | Nucleus | other | 1.037 |
| NCKAP1 | NCK-associated protein 1 | Plasma Membrane | other | 1.043 |
| NHSL1 | NHS-like 1 | unknown | other | 0.960 |
| NR3C1 | nuclear receptor subfamily 3, group C, member 1 (glucocorticoid receptor) | Nucleus | ligand-dependent nuclear receptor | 1.078 |
| NTSR1 | neurotensin receptor 1 (high affinity) | Plasma Membrane | G-protein coupled receptor | 1.053 |
| OIP5-AS1 | OIP5 antisense RNA 1 (non-protein coding) | unknown | other | 0.888 |
| OR52B2 | olfactory receptor, family 52, subfamily B, member 2 | Plasma Membrane | G-protein coupled receptor | 1.065 |
| OTOGL | otogelin-like | unknown | other | 1.031 |
| PEX5L | peroxisomal biogenesis factor 5-like | Cytoplasm | ion channel | 0.932 |
| PHLDA3 | pleckstrin homology-like domain, family A, member 3 | Plasma Membrane | other | 1.067 |
| PIM1 | pim-1 oncogene | Cytoplasm | kinase | 1.054 |
| PLD4 | phospholipase D family, member 4 | unknown | enzyme | 1.085 |
| POU4F2 | POU class 4 homeobox 2 | Nucleus | transcription regulator | 1.034 |
| PRKCH | protein kinase C, eta | Cytoplasm | kinase | 1.156 |
| PRODH2 | proline dehydrogenase (oxidase) 2 | Cytoplasm | enzyme | 1.062 |
| PVRL3 | poliovirus receptor-related 3 | Plasma Membrane | other | 1.066 |
| PYCR1 | pyrroline-5-carboxylate reductase 1 | Cytoplasm | enzyme | 1.048 |
| RAB3C (includes EG:115827) | RAB3C, member RAS oncogene family | Cytoplasm | enzyme | 0.941 |
| RELN | reelin | Extracellular Space | peptidase | 1.081 |
| RMI2 | RMI2, RecQ mediated genome instability 2, homolog (*S. cerevisiae*) | unknown | other | 1.069 |
| RND3 | Rho family GTPase 3 | Cytoplasm | enzyme | 1.026 |
| RNF128 | ring finger protein 128, E3 ubiquitin protein ligase | Cytoplasm | enzyme | 0.952 |
| RPS6KB2 | ribosomal protein S6 kinase, 70 kDa, polypeptide 2 | Cytoplasm | kinase | 1.098 |
| RUNX1T1 | runt-related transcription factor 1; translocated to, 1 (cyclin D-related) | Nucleus | transcription regulator | 1.055 |
| SCGN | secretagogin, EF-hand calcium binding protein | Cytoplasm | other | 1.037 |
| SCN8A | sodium channel, voltage gated, type VIII, alpha subunit | Plasma Membrane | ion channel | 0.924 |
| SEMA4C | sema domain, immunoglobulin domain (Ig), transmembrane domain (TM) and short cytoplasmic domain, (semaphorin) 4C | Plasma Membrane | other | 1.146 |
| SEMA5A | sema domain, seven thrombospondin repeats (type 1 and type 1-like), transmembrane domain (TM) and short cytoplasmic domain, (semaphorin) 5A | Plasma Membrane | transmembrane receptor | 1.083 |
| SERPINA10 | serpin peptidase inhibitor, clade A (alpha-1 antiproteinase, antitrypsin), member 10 | Extracellular Space | other | 1.029 |
| SERPIND1 | serpin peptidase inhibitor, clade D (heparin cofactor), member 1 | Extracellular Space | other | 1.036 |
| SERPINE1 | serpin peptidase inhibitor, clade E (nexin, plasminogen activator inhibitor type 1), member 1 | Extracellular Space | other | 1.093 |
| SHE | Src homology 2 domain containing E | Cytoplasm | other | 1.043 |
| SLC18A3 | solute carrier family 18 (vesicular acetylcholine), member 3 | Plasma Membrane | transporter | 1.056 |
| SLC22A18 | solute carrier family 22, member 18 | Plasma Membrane | transporter | 1.176 |
| SLC22A7 | solute carrier family 22 (organic anion transporter), member 7 | Plasma Membrane | transporter | 1.082 |
| SLC25A27 | solute carrier family 25, member 27 | Cytoplasm | transporter | 0.952 |
| SLC38A3 | solute carrier family 38, member 3 | Plasma Membrane | transporter | 1.046 |
| SLITRK1 | SLIT and NTRK-like family, member 1 | unknown | other | 0.917 |
| SLITRK1 | SLIT and NTRK-like family, member 1 | unknown | other | 0.948 |
| SMAD3 | SMAD family member 3 | Nucleus | transcription regulator | 1.042 |
| SORBS2 | sorbin and SH3 domain containing 2 | Plasma Membrane | other | 0.961 |
| STAG3L1 | stromal antigen 3-like 1 | unknown | other | 1.088 |
| STARD13 | StAR-related lipid transfer (START) domain containing 13 | Cytoplasm | other | 1.221 |
| STX1B | syntaxin 1B | Plasma Membrane | ion channel | 0.915 |
| SYCP3 | synaptonemal complex protein 3 | Nucleus | other | 1.023 |
| TAOK1 | TAO kinase 1 | Cytoplasm | kinase | 0.965 |
| TGM4 | transglutaminase 4 (prostate) | Extracellular Space | enzyme | 1.086 |
| TIMM17B | translocase of inner mitochondrial membrane 17 homolog B (yeast) | Cytoplasm | transporter | 1.035 |
| TMEM56 | transmembrane protein 56 | unknown | other | 0.947 |
| TNFRSF10C | tumor necrosis factor receptor superfamily, member 10c, decoy without an intracellular domain | Plasma Membrane | transmembrane receptor | 1.028 |
| TP73 | tumor protein p73 | Nucleus | transcription regulator | 1.045 |

TABLE 3-continued

Rapamycin-sensitive genes differentially regulated in brain of Alzheimer's disease patients with advanced disease (178 known genes)

| Symbol | Entrez Gene Name | Location | Type(s) | Fold Change |
| --- | --- | --- | --- | --- |
| TRPV1 | transient receptor potential cation channel, subfamily V, member 1 | Plasma Membrane | ion channel | 1.032 |
| TSC2 | tuberous sclerosis 2 | Cytoplasm | other | 1.045 |
| UCA1 | urothelial cancer associated 1 (non-protein coding) | unknown | other | 1.040 |
| VEGFA | vascular endothelial growth factor A | Extracellular Space | growth factor | 1.090 |
| VSNL1 | visinin-like 1 | Cytoplasm | other | 0.848 |
| WFDC11 | WAP four-disulfide core domain 11 | Extracellular Space | other | 1.030 |
| XRN1 | 5'-3' exoribonuclease 1 | Cytoplasm | enzyme | 1.023 |
| YPEL1 | yippee-like 1 (*Drosophila*) | Nucleus | enzyme | 0.934 |
| ZADH2 | zinc binding alcohol dehydrogenase domain containing 2 | Cytoplasm | enzyme | 1.133 |
| ZBTB20 | zinc finger and BTB domain containing 20 | Nucleus | other | 1.052 |
| ZC3H6 | zinc finger CCCH-type containing 6 | unknown | other | 0.928 |

TABLE 4

Rapamycin-sensitive genes differentially regulated in brain of Alzheimer's disease patients with mild disease - new targets

| Symbol | Entrez Gene Name | Location | Type(s) | Fold Change |
| --- | --- | --- | --- | --- |
| ABTB1 | ankyrin repeat and BTB (POZ) domain containing 1 | Cytoplasm | translation regulator | 1.057 |
| AHNAK2 | AHNAK nucleoprotein 2 | unknown | other | 1.056 |
| BARX2 | BARX homeobox 2 | Nucleus | transcription regulator | 1.077 |
| BTNL9 | butyrophilin-like 9 | unknown | other | 1.056 |
| CACNA1D | calcium channel, voltage-dependent, L type, alpha 1D subunit | Plasma Membrane | ion channel | 1.063 |
| CARD14 | caspase recruitment domain family, member 14 | Cytoplasm | other | 1.034 |
| CC2D2A | coiled-coil and C2 domain containing 2A | unknown | other | 1.102 |
| CEP68 | centrosomal protein 68 kDa | Cytoplasm | other | 1.036 |
| CPXM2 | carboxypeptidase X (M14 family), member 2 | Extracellular Space | peptidase | 1.026 |
| CREB3L4 | cAMP responsive element binding protein 3-like 4 | Nucleus | transcription regulator | 1.064 |
| CTDSP1 | CTD (carboxy-terminal domain, RNA polymerase II, polypeptide A) small phosphatase 1 | Nucleus | phosphatase | 1.098 |
| DCAF12L1 | DDB1 and CUL4 associated factor 12-like 1 | unknown | other | 1.030 |
| FAM64A | family with sequence similarity 64, member A | Nucleus | other | 1.214 |
| FCGBP | Fc fragment of IgG binding protein | Extracellular Space | other | 1.057 |
| FJX1 | four jointed box 1 (*Drosophila*) | Extracellular Space | other | 1.123 |
| FN3K | fructosamine 3 kinase | Cytoplasm | kinase | 1.258 |
| GLI2 | GLI family zinc finger 2 | Nucleus | transcription regulator | 1.032 |
| GLRA1 | glycine receptor, alpha 1 | Plasma Membrane | ion channel | 1.041 |
| GPR176 | G protein-coupled receptor 176 | Plasma Membrane | G-protein coupled receptor | 1.092 |
| HHIPL1 | HHIP-like 1 | unknown | other | 1.057 |
| HOXD10 | homeobox D10 | Nucleus | transcription regulator | 1.024 |
| HYDIN | HYDIN, axonemal central pair apparatus protein | unknown | other | 1.077 |
| KLF2 | Kruppel-like factor 2 (lung) | Nucleus | transcription regulator | 1.084 |
| MFAP5 | microfibrillar associated protein 5 | Extracellular Space | other | 1.024 |
| PHLDA3 | pleckstrin homology-like domain, family A, member 3 | Plasma Membrane | other | 1.056 |
| POU4F2 | POU class 4 homeobox 2 | Nucleus | transcription regulator | 1.040 |
| RHO | rhodopsin | Plasma Membrane | G-protein coupled receptor | 1.024 |
| RUNX1T1 | runt-related transcription factor 1; translocated to, 1 (cyclin D-related) | Nucleus | transcription regulator | 1.053 |
| STARD13 | StAR-related lipid transfer (START) domain containing 13 | Cytoplasm | other | 1.269 |
| TRIB1 | tribbles homolog 1 (*Drosophila*) | Cytoplasm | kinase | 1.041 |

TABLE 5

Rapamycin-sensitive genes differentially regulated in brain of Alzheimer's disease patients with advanced disease - new targets

| Symbol | Entrez Gene Name | Location | Type(s) | Fold Change |
| --- | --- | --- | --- | --- |
| ABLIM2 | actin binding LIM protein family, member 2 | Cytoplasm | other | 0.905 |
| ABTB1 | ankyrin repeat and BTB (POZ) domain containing 1 | Cytoplasm | translation regulator | 1.058 |
| ACSL6 | acyl-CoA synthetase long-chain family member 6 | Cytoplasm | enzyme | 0.937 |
| ACTRT1 | actin-related protein T1 | Cytoplasm | other | 1.025 |
| AHNAK2 | AHNAK nucleoprotein 2 | unknown | other | 1.056 |
| AP1S1 | adaptor-related protein complex 1, sigma 1 subunit | Cytoplasm | transporter | 0.955 |
| ATAD3A/ATAD3B | ATPase family, AAA domain containing 3A | Nucleus | other | 1.078 |
| ATF7IP | activating transcription factor 7 interacting protein | Nucleus | transcription regulator | 0.934 |

TABLE 5-continued

Rapamycin-sensitive genes differentially regulated in brain of Alzheimer's disease patients with advanced disease - new targets

| Symbol | Entrez Gene Name | Location | Type(s) | Fold Change |
|---|---|---|---|---|
| ATRNL1 | attractin-like 1 | unknown | other | 0.865 |
| BARX2 | BARX homeobox 2 | Nucleus | transcription regulator | 1.080 |
| BCOR | BCL6 corepressor | Nucleus | transcription regulator | 1.032 |
| BTNL9 | butyrophilin-like 9 | unknown | other | 1.063 |
| CACNA1D | calcium channel, voltage-dependent, L type, alpha 1D subunit | Plasma Membrane | ion channel | 1.070 |
| CARD14 | caspase recruitment domain family, member 14 | Cytoplasm | other | 1.025 |
| CC2D2A | coiled-coil and C2 domain containing 2A | unknown | other | 1.098 |
| CEP68 | centrosomal protein 68 kDa | Cytoplasm | other | 1.040 |
| CPXM2 | carboxypeptidase X (M14 family), member 2 | Extracellular Space | peptidase | 1.030 |
| CREB3L4 | cAMP responsive element binding protein 3-like 4 | Nucleus | transcription regulator | 1.054 |
| CTDSP1 | CTD (carboxy-terminal domain, RNA polymerase II, polypeptide A) small phosphatase 1 | Nucleus | phosphatase | 1.119 |
| DCLK1 | doublecortin-like kinase 1 | Plasma Membrane | kinase | 0.939 |
| DLG2 | discs, large homolog 2 (*Drosophila*) | Plasma Membrane | kinase | 0.917 |
| DNAH6 | dynein, axonemal, heavy chain 6 | unknown | other | 0.957 |
| DYNC2LI1 | dynein, cytoplasmic 2, light intermediate chain 1 | Cytoplasm | other | 0.946 |
| DZIP3 | DAZ interacting protein 3, zinc finger | Cytoplasm | enzyme | 0.905 |
| ELAVL4 | ELAV (embryonic lethal, abnormal vision, *Drosophila*)-like 4 (Hu antigen D) | Cytoplasm | other | 0.931 |
| FAM155A | family with sequence similarity 155, member A | unknown | other | 0.860 |
| FAM64A | family with sequence similarity 64, member A | Nucleus | other | 1.154 |
| FAT3 | FAT tumor suppressor homolog 3 (*Drosophila*) | unknown | other | 0.954 |
| FJX1 | four jointed box 1 (*Drosophila*) | Extracellular Space | other | 1.104 |
| FN3K | fructosamine 3 kinase | Cytoplasm | kinase | 1.269 |
| GABBR2 | gamma-aminobutyric acid (GABA) B receptor, 2 | Plasma Membrane | G-protein coupled receptor | 0.862 |
| GALNT10 | UDP-N-acetyl-alpha-D-galactosamine:polypeptide N-acetylgalactosaminyltransferase 10 (GalNAc-T10) | Cytoplasm | enzyme | 1.064 |
| GLI2 | GLI family zinc finger 2 | Nucleus | transcription regulator | 1.033 |
| GLRA1 | glycine receptor, alpha 1 | Plasma Membrane | ion channel | 1.043 |
| GPR176 | G protein-coupled receptor 176 | Plasma Membrane | G-protein coupled receptor | 1.098 |
| GSG1L | GSG1-like | unknown | other | 1.025 |
| HHIPL1 | HHIP-like 1 | unknown | other | 1.063 |
| HOXD10 | homeobox D10 | Nucleus | transcription regulator | 1.038 |
| HYDIN | HYDIN, axonemal central pair apparatus protein | unknown | other | 1.090 |
| IRX4 | iroquois homeobox 4 | Nucleus | transcription regulator | 1.032 |
| KLF2 | Kruppel-like factor 2 (lung) | Nucleus | transcription regulator | 1.103 |
| KRTAP9-2 | keratin associated protein 9-2 | unknown | other | 1.022 |
| MBD3L2 (includes others) | methyl-CpG binding domain protein 3-like 2 | unknown | other | 1.025 |
| MCTP1 | multiple C2 domains, transmembrane 1 | unknown | other | 0.914 |
| MFAP5 | microfibrillar associated protein 5 | Extracellular Space | other | 1.026 |
| MMP16 | matrix metallopeptidase 16 (membrane-inserted) | Extracellular Space | peptidase | 0.928 |
| PEX5L | peroxisomal biogenesis factor 5-like | Cytoplasm | ion channel | 0.932 |
| PHLDA3 | pleckstrin homology-like domain, family A, member 3 | Plasma Membrane | other | 1.067 |
| POU4F2 | POU class 4 homeobox 2 | Nucleus | transcription regulator | 1.034 |
| PYCR1 | pyrroline-5-carboxylate reductase 1 | Cytoplasm | enzyme | 1.048 |
| RND3 | Rho family GTPase 3 | Cytoplasm | enzyme | 1.026 |
| RNF128 | ring finger protein 128, E3 ubiquitin protein ligase | Cytoplasm | enzyme | 0.952 |
| RUNX1T1 | runt-related transcription factor 1; translocated to, 1 (cyclin D-related) | Nucleus | transcription regulator | 1.055 |
| SLITRK1 | SLIT and NTRK-like family, member 1 | unknown | other | 0.917 |
| SLITRK1 | SLIT and NTRK-like family, member 1 | unknown | other | 0.948 |
| SORBS2 | sorbin and SH3 domain containing 2 | Plasma Membrane | other | 0.961 |
| STAG3L1 | stromal antigen 3-like 1 | unknown | other | 1.088 |
| STARD13 | StAR-related lipid transfer (START) domain containing 13 | Cytoplasm | other | 1.221 |
| STX1B | syntaxin 1B | Plasma Membrane | ion channel | 0.915 |
| TGM4 | transglutaminase 4 (prostate) | Extracellular Space | enzyme | 1.086 |
| TMEM56 | transmembrane protein 56 | unknown | other | 0.947 |
| WFDC11 | WAP four-disulfide core domain 11 | Extracellular Space | other | 1.030 |
| YPEL1 | yippee-like 1 (*Drosophila*) | Nucleus | enzyme | 0.934 |

The invention will now be further understood with reference to the following non-limiting examples.

EXAMPLES

Example 1 Gene Expression Microarray Analysis of Brain Samples from Alzheimer's Disease Patients 1.1 Patients and Biomaterials Human brain tissue collected by the Oxford Project to Investigate Memory and Aging (OPTIMA) was made available through the Thomas Willis brain bank. In total, samples from 252 brains were available from a mix of elderly controls and patients suffer from preclinical, mild and severe AD at the time of death (as determined by Braak staging). The number of cases included in the study was based on availability, not statistical power calculations, as the outcome, and hence number of patients in each group-of-interest, was unknown. The tissue was snap frozen at the time of autopsy: and available from the lateral temporal lobe (severely affected by AD pathology), frontal lobe (affected by AD pathology) and occipital lobe (largely unaffected by AD pathology). A wealth of clinical information was available about each patient, including: Braak stage (severity of AD); additional pathology; age of onset and age at death; personal and family history of cancer; plasma homocysteine levels, and the results of annual clinical tests including test of cognitive performance (CAMCOG).

1.2 DNA, RNA and Protein Extraction

RNA, DNA and protein were isolated from lateral temporal, frontal and occipital lobe tissue of each patient by TRI-reagent extraction. 100 mg of frozen tissue was homogenised in 1 ml TRI-reagent, incubated at room temperature (RT) for 5 minutes, and supplemented with 100 µl 1-bromo-3-chloropropane. The solution was vigorously mixed for 15 seconds, incubated for 2 minutes, and centrifuged at 12,000 rotational centrifugal force (g) for 15 minutes at 4° C. to separate the RNA, DNA and protein layers.

The aqueous RNA layer was transferred to an eppendorf, supplemented with 500 µl isopropanol and mixed gently by inversion. After five minute incubation, the solution was centrifuged at 12,000 g for 8 minutes at 4° C. The pellet was washed in 1 ml 75% ethanol, centrifuged at 7,500 g for 5 minutes at 4° C., and ethanol wash removed. The pellet was air-dried for 30 minutes and rehydrated in 100 µl nuclease free water by incubation at 55° C. for 15 minutes, prior to storage at −80° C.

RNA was converted to cDNA by reverse transcription: 50 µl of 200 ng/µl RNA was added to 50 µl of Reverse Transcriptase master mix (composed of 10 µl 10×reverse transcriptase buffer; 4 µl dNTP mix (100 mM); 10 µl random primers; 5 µl MultiScribe Reverse Transcriptase (50 U/µl); and 21 µl nuclease free water), and incubated at 25° C. for 10 minutes; 37° C. for 120 minutes and 85° C. for 5 seconds in a Thermal cycler. The cDNA was precipitated with isopropanol (100 µl cDNA supplemented with 20 µl of 3M sodium citrate at pH 5 and 400 µl isopropanol), centrifuged at high speed for 10 minutes, and the resulting pellet washed in ice cold 100% ethanol. Following high speed centrifugation and supernatant removal, the pellet was air dried overnight, and rehydrated in 100 µl nuclease free water, prior to storage at 4° C.

The remaining TRI-reagent layers were supplemented with 300 µl ethanol and centrifuged at 12,000 g for 5 minutes at 4° C. to produce the DNA pellet. The pink supernatant was transferred to a clean eppendorf in preparation for protein extraction. The DNA pellet was washed three times, 1 hour per wash, in 0.1M sodium citrate in 10% ethanol, with centrifugation at 12,000 g for 5 minutes between washes. Following a 30 minute wash in 75% ethanol, the pellet was centrifuged at 2,000 g for 5 minutes to allow wash removal, and the pellet air dried overnight. The pellet was dissolved in nuclease free water for 24 hours, centrifuged at 16,000 g for 10 minutes, and supernatant transferred to a clean tube to separate DNA from any insoluble material. The DNA was stored at 4° C.

The protein was precipitated from the pink layer by 15 minute incubation with 3 volumes acetone prior to centrifugation at 12,000 g for 10 min at 4° C. The protein pellet was subjected to three 10 minute washes in 0.3M guanidine hydrochloride in 95% ethanol and 2.5% glycerol, and dissolved in radio-immunoprecipitation (RIPA) buffer (composition: 0.1M sodium chloride, 0.01M Tris hydrochloride, 1:500 EDTA, 400 ug/ml phenylmethanesulfonylfluoride, 2 ug/ml aprotinin and 1% sodium dodecyl sulphate). The protein was stored at −20° C.

1.3 One-Colour Custom Microarray Based Gene Expression Analysis (Agilent)

8×15K Custom Microarrays (Agilent Technologies: able to accommodate up to 15,000 genes) were designed to include various housekeeping genes (719 genes), internal controls (3141 genes), and genes that were differentially expressed in AD brain relative to control brain based on a published dataset (Xu, P. T. et al. Differences in apolipoprotein E3/3 and E4/4 allele-specific gene expression in hippocampus in Alzheimer disease. Neurobiol. Dis. 21, 256-275 (2006); Xu, P. T. et al. A SAGE study of apolipoprotein E3/3, E3/4 and E4/4 allele-specific gene expression in hippocampus in Alzheimer disease. Mol. Cell Neurosci. 36, 313-331 (2007) (3718 genes). The remaining 7422 spaces were filled with known rapamycin-regulated genes (based on an IPA Ingenuity search) and the genes that were identified as rapamycin-regulated in lymphocytes based on two-colour microarray based gene expression analysis.

Of the 252 patients for whom tissue was available through the Thomas Willis brain bank, 32 patients were selected for one-colour custom microarray based gene expression analysis. They included control subjects and patients with mild and advanced AD. The exclusion criteria were as follows: vascular disease; Parkinson's disease; ApoE ε2/ε2, ApoE ε2/ε3 and ApoE ε4/ε4 genotypes (not enough patients for meaningful statistical analysis); and high plasma homocysteine level (>35 µM).

1.3.1 Sample Preparation

RNA was extracted from the frontal lobe of each subject by TRI-reagent protocol as described in 1.2. The RNA was treated with DNase. The suitability of the RNA for microarray based gene expression analysis was determined by Agilent RNA nano-chip analysis. RIN values ranged from 2-3 indicating relatively poor quality RNA. However, this was unavoidable, as the source brain tissue had significant post-mortem time prior to freezing, resulting in inevitable degradation.

1.3.2 Conversion of RNA to Labelled cRNA 200 ng of RNA was converted to cDNA, and subsequently to labelled cRNA, with the low-input quick amplification labelling kit. The spike mix was incubated at 37° C. for 5 minutes, and diluted in the provided dilution buffer (Agilent Techologies) as shown in Table 6. 2 µl of the diluted spike mix was added to the RNA (200 ng) in a 1.5 µl volume. Cyanine 3-CTP was used to label all samples. The labelled and amplified cRNA samples were purified by standard Qiagen RNeasy mini column protocol, and quality assessed and quantified.

TABLE 6

Preparation of Spike Mix

| Starting amount of RNA | | Serial dilutions | | | | Spike mix volume per labelling (µl) |
|---|---|---|---|---|---|---|
| Total RNA (ng) | Concentration (ng/µl) | First | Second | Third | Fourth | |
| 200 | 133.3 | 1:20 | 1:25 | 1:10 | | 2 |

1.3.3 Hybridisation 600 ng of labelled cRNA was added to various fragmentation components (Table 7), incubated at 60° C. for 30 minutes, and cooled on ice for 1 min. 25 µl of GEx Hybridisation buffer HI-RPM was added to stop fragmentation. The sample was gently mixed, centrifuged at 13,000 rpm for 1 min, and placed on ice in preparation for hybridisation. The microarray was assembled and incubated overnight: the Custom 8×15K Microarray was used and 40 µl of sample was added per 15K array. After 17 hour hybridisation, the microarrays were washed and scanned on the Agilent C Scanner on programme AgilentHD_GX_1 color, with the settings amended as shown in Table 8.

TABLE 7

Fragmentation components

| Components (Agilent) | Volume/Mass (for 8 × 15K microarray) |
|---|---|
| Cy3-labelled cRNA | 600 ng |
| 10 × blocking agent | 5 µl |
| Nuclease free water | Bring total volume to 24 µl |
| 25 × fragmentation buffer | 1 µl |
| Total volume | 25 µl |

TABLE 8

Microarray scanner settings for one-colour microarray based gene expression analysis (Agilent)

| | 8 × 15K HD microarray format |
|---|---|
| Dye Channel | Green |
| Scan region | Scan area (61 × 21.6 mm) |
| Scan resolution (µM) | 5 |
| Tiff | 20 bit |

1.3.4. Data Analysis

The feature extraction programme was used to collate the Custom Microarray layout with the output of the scanner. The results from individual patients were grouped based on subject diagnosis, disease severity (as defined by Braak stage) and ApoE genotype. For the purposes of this study, the groups-of-interest were as follows (see Table 9):

TABLE 9

| Patient diagnosis | ApoE genotype | Number of patients |
|---|---|---|
| Control (entorhinal stage) | ApoE ε3/ε3 | 5 |
| Mild AD (limbic stage) | ApoE ε3/ε3 | 5 |
| Advanced AD (neocortical stage) | ApoE ε3/ε3 | 4 |
| Advanced AD (neocortical stage) | ApoE ε3/ε4 | 18 |

Statistical Analysis of Microarray (SAM) was used to carry out unpaired, two-sample T tests for each gene in a group-of-interest compared to control. SAM identifies genes that are differentially expressed at RNA level in the group-of-interest compared to control group; the direction of expression; fold change; and an estimate of the false discovery rate (FDR). For the purpose of our study, we selected an estimated FDR of 10% as acceptable for identifying differentially expressed genes. SAM was carried out with 1000 permutations, and the output processed to remove duplicates. The output was analysed with the IPA Ingenuity software (www.ingenuity.com).

Tables 2 shows differentially expressed transcripts in brain from early AD patients (limbic stage) relative to control (entorhinal stage). Table 3 shows differentially expressed transcripts in brain from advanced AD patients (neocortical stage) relative to control (entorhinal stage).

Example 2 Q-PCR Validation of Microarray Results

Real-time PCR (Q-PCR) allows relative quantification of a gene-of-interest by calculating the expression of the gene relative to a housekeeping gene such as beta-actin, allowing patient to patient comparison. The validation study was carried out on cDNA obtained from the same patients and brain regions that were used for the microarray study. The genes were selected as they were shown to be either significantly up- or down-regulated in advanced AD (neocortical stage) compared to control in the microarray study. The Universal probe library design centre (Roche Diagnostic Website) was used to design Q-PCR systems for the genes (see Table 10); and primers and probes ordered from Sigma Genosys and Roche respectively.

TABLE 10

Roche probe, primer sequences, and optimal annealing temperature corresponding to each gene-of-interest

| Gene | Roche Probe | Forward primer (5'-3') | Backward primer (5'-3') | Optimal annealing temperature (° C.) |
|---|---|---|---|---|
| Beta actin | 24 | TCAGCTGTGGGGTCCTGT | GAAGGGGACAGGCAGTGAG | 62 |

TABLE 10-continued

Roche probe, primer sequences, and optimal annealing temperature corresponding to each gene-of-interest

| Gene | Roche Probe (5'-3') | Forward primer (5'-3') | Backward primer (5'-3') | Optimal annealing temperature (° C.) |
|---|---|---|---|---|
| EIF4E (Variant 1 and 2) | 35 | GATGGCGACTGTCG AACC | TGGGTTAGCAACCTC CTGAT | 60 |
| EIF4E (Variant 3) | 35 | GTGTAGCGCACACT TTCTGG | TGGGTTAGCAACCTC CTGAT | 60 |
| MAPK1 (Variant 1 and 2) | 62 | CCGTGACCTCAAGC CTTC | GCCAGGCCAAAGTCA CAG | 58 |
| GABBR2 | 3 | GCGAAGGACAGTGG AGAAGT | GAGAGGGCGGATGGA GATA | 62 |
| SEMA4C | 14 | TTGTGCCGCGTAAG ACAGT | CAGCGTCAGTGTCAG GAAGT | 60 |
| DZIP3 | 39 | TGCCCAAGATCTGA TACAAGG | CTCCAACACACCACC GTACA | 60 |
| SERPINE1 | 80 | CTCCTGGTTCTGCC CAAGT | CAGGTTCTCTAGGGG CTTCC | 58 |

For the composition of each 20 μl Q-PCR mix see Table 11. Two negative controls (water) and a cDNA standard curve (five serial dilutions starting with neat cDNA) were included per Q-PCR run. The samples were denatured at 96° C. for 15 minutes and amplified by 40 cycles of 96° C. for 15 seconds, optimal annealing temperature (Table 10) for 30 seconds and 72° C. for 30 seconds. FAM output was read in the annealing phase.

TABLE 11

| Composition of Q-PCR reaction | Manufacturer |
|---|---|
| 0.5 μl Universal probe (10 μM) | Roche |
| 10 μl Absolute Q-PCR mix (Compositition: 0.625 Units ThermoPrime Taq DNA polymerase, 75 mM Tris HCl (pH 8.8 at 25° C.), 20 mM $(NH_4)_2SO_4$, 1.5 mM $MgCl_2$, 0.01% (v/v) tween 20, 0.2 mM each of dATP, dCTP, dGTP, dTTP). | ThermoScientific |
| 0.5 μl forward primer (20 μM) | Sigma Genosys |
| 0.5 μl backward primer (20 μM) | Sigma Genosys |
| 6.5 μl nuclease free water | Qiagen |
| 2 μl cDNA (neat, 1:4 and 1:16) | Prepared as above |

2.1 Data Analysis

Each of the cDNA standard curve serial dilutions were assigned an arbitrary copy number (1:1=10,000; 1:2=5,000; 1:4=2500; 1:8=1250; 1:16=625). The Rotor gene-6 programme automatically identifies the optimal threshold and determines the copy number of the gene-of-interest relative to the standard curve for each sample. The Q-PCR was considered fully optimised when the calculated standard curve copy number varied less than 10% from the assigned copy number. The values obtained for each gene were normalised to the corresponding beta-actin values to allow quantitative comparison of samples.

Example 2 Modulation of Rapamycin-Sensitive Genes has the Same Beneficial Effect on Alzheimer's Disease-Related Protein Expression as Rapamycin 2.1 Methods The genes identified as rapamycin-sensitive genes (existing Table 1) were used for computer based (in silico) molecular network modelling and analysis (using the IPA molecular network tools). In silico simulation of molecular interactions in the AD brain was also carried out based on the expression pattern of the rapamycin-sensitive genes shown in Table 2. Selected rapamycin-sensitive genes were used for further simulations to predict the effect of silencing these rapamycin-sensitive genes on AD-related pathology.

The simulations were followed by experiments to verify whether the modulation of the downstream effectors of mTOR (rapamycin-sensitive genes) would lead to measureable changes in MAPT (microtubule associated protein tau) similar to rapamycin.

In the cellular models used, the mTOR activation is achieved by growth factors in the serum. The inhibition of mTOR by the addition of rapamycin counteracts this effect and reduces the production of AD-type phospho-tau in the cultures.

Cell Culture

SH-SY5Y human neuroblastoma cells were purchased from ECACC and cultured in DMEM/F-12 (Sigma) supplemented with 10% FCS Gold (PAA), 100 U penicillin-streptomycin (Invitrogen) and 2 mM L-glutamine (Sigma). Cells were kept in a humidified atmosphere at 37° C. and 5% $CO_2$. Cells were seeded in 96-well plates and cultured for 24 hours before siRNA treatment.

siRNA Treatment of SH-SY5Y Cells siRNA was purchased from Origene and applied at 1 nM concentration for 48 hours. siRNA duplexes (Origene) were supplied as 20 μM stock solutions. siRNA was diluted in OPTIMEM to a 300 nM concentration and incubated at room temperature (RT) for 10 min. Lipofectamine (RNAiMAX) was also diluted in OPTIMEM and incubated at RT for 10 min. The lipofectamine mix and the duplex mix were added to the culture medium (antibiotic free) to achieve the final concentration of 1 nM siRNA and 0.3% lipofectamine. Cells were incubated at 37° C. for 4 hours, and then media was replaced with antibiotic free media until collection. Some cultures were treated with additional rapamycin for the last 24 hours of the culture period.

Immunostaining

Cells were sequentially fixed in Glyo-Fixx (Thermo Scientific) for 2 hours at RT and in 85% cold ethanol for 30 min. Blocking (of non-specific staining) was performed for 30 min at RT using 5% BSA and 0.1% Triton-X-100 in PBS. Cells were incubated with primary antibody overnight at 4° C. (for the negative controls, cells were incubated with PBS-Triton only). Cells were washed in PBS-0.1% Triton and incubated with secondary antibody (FITC conjugated) for 2 hours at 4° C. Cells were washed in PBS-0.1% Triton and propidium iodide counterstained. The antibodies used were mouse polyclonal to phospho-Tau (Abcam, 1:200) and anti-mouse IgG-FITC (Abcam, 1:400).

Propidium Iodide Staining

Cells were incubated with propidium iodide (Invitrogen, 10 μg/ml) supplemented with RNaseA (Sigma, 100 μg/ml) for 20 min at 37° C. and scanned.

Cytometry

Cytometry was performed using the Acumen Explorer TTP Lab Tech, Ltd. (Software version 3.1.12).

The propidium iodide staining was used to determine the cell cycle phase of the cells based on DNA content. It was measured using a 488 nm excitation laser triggering the 3° channel (bandpass filter 585-620 nm).

The immunostaining was used to measure the content of phospho-Tau in the cells. Measurement was carried out using a laser triggering the 1° channel (bandpass filter 500-530 nm).

Cell Cycle Analysis

To determine cut-offs for cells in different phases of the cell cycle, gate setting was performed based on the G1 and G2 peaks on the DNA content histogram. To determine the G1 and G2 peaks, the 3° total intensity in 20% histograms was analysed for each plate. Gates calculated were manually entered into the Acumen software.

The data exported and quantified included separately all cells and single cells. Single cells were further subcategorised into euploid, apoptotic and polyploid cells. Euploid cells were additionally classified into cells in G1S and G2M phases of the cell cycle.

Cellular Protein Measurement

The total fluorescence intensity from the 1° channel was used to compare total protein levels in the different cell populations defined above. Mean fluorescence intensity per cell (for the whole of the population) and mean fluorescence intensity per cell (for positive cells only) were analysed separately. Additionally the proportion of positive cells in each population was calculated.

2.2 Results 2.2.1 The Effects of Rapamycin

The in silico simulations (using the IPA molecular network modelling tool) indicated that the rapamycin regulated molecules interact with the AD-related proteins APP (amyloid precursor protein) and the microtubule associated protein tau (MAPT). The in silico analysis indicated that the activation of mTOR in normal circumstances would lead to the inhibition of MAPT and APP.

The gene expression patterns of rapamycin-sensitive genes in early stage AD patients (as shown in existing Table 2) were used to predict the activation state of APP and MAPT in the brain. Based on the expression pattern of rapamycin-sensitive genes in the early (limbic) stage of AD, the inhibition of MAPT and APP was predicted. The in silico simulation also predicted that this gene expression pattern is associated with the activation of mTOR. However, the expression pattern of many rapamycin-sensitive genes in the brain of AD patients is inconsistent with the known normal molecular interactions. This indicates that the AD-related deregulation of the mTOR pathway is also associated with unexpected variations from normal molecular interactions that are compatible with the idea that these molecules have variants (SNPs or other genetic variations) that interfere with their normal interactions.

The simulated inhibition of mTOR in this system (using rapamycin) will reverse the AD-associated inhibition of MAPT and APP, indicating that rapamycin could reverse the molecular expression changes seen in AD.

In the experimental paradigm mTOR is activated in the neuronal cells (in the presence of growth factors from the serum). The addition of rapamycin (100 ng/ml) will inhibit mTOR, leading to the down regulation of AD-related phospho-tau (p-tau) in the cells.

In the SH-SY5Y cellular model, p-tau expression was regulated in a cell-cycle dependent manner and protein content of cells was generally higher in the cells that were in the G2 phase of the cell cycle relative to cells in the G1 phase of the cell cycle (FIG. 1: White bars represent the G1 phase cell population; black bars represent the G2 phase population).

Figure 2:
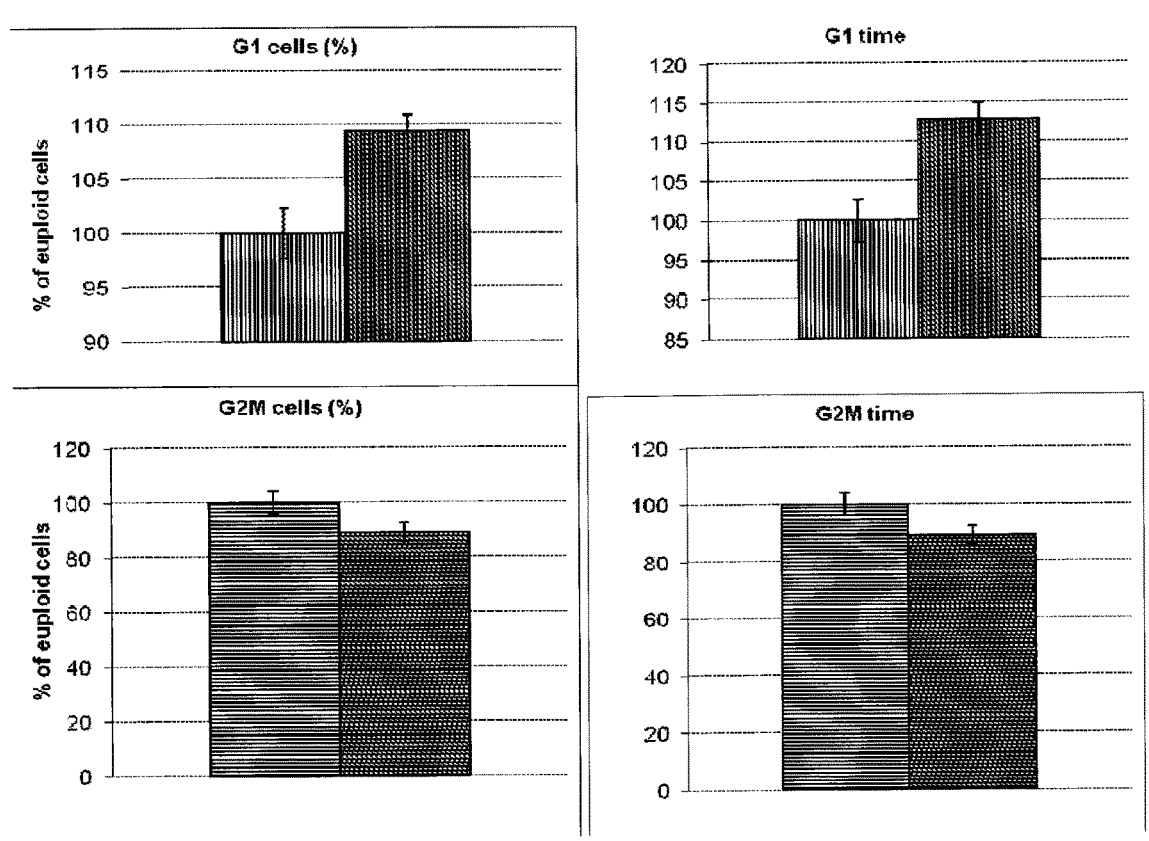
FIG. 2 Effect of rapamycin on cell cycle kinetics in SH-SY5Y neuroblastoma cells. Vertically-shaded bars=G1 population; Horizontally-shaded bars=G2 population; Lighter shading=control cells treated with culture medium; Darker shading=cells treated with 100 ng/ml rapamycin.
Figure 3:
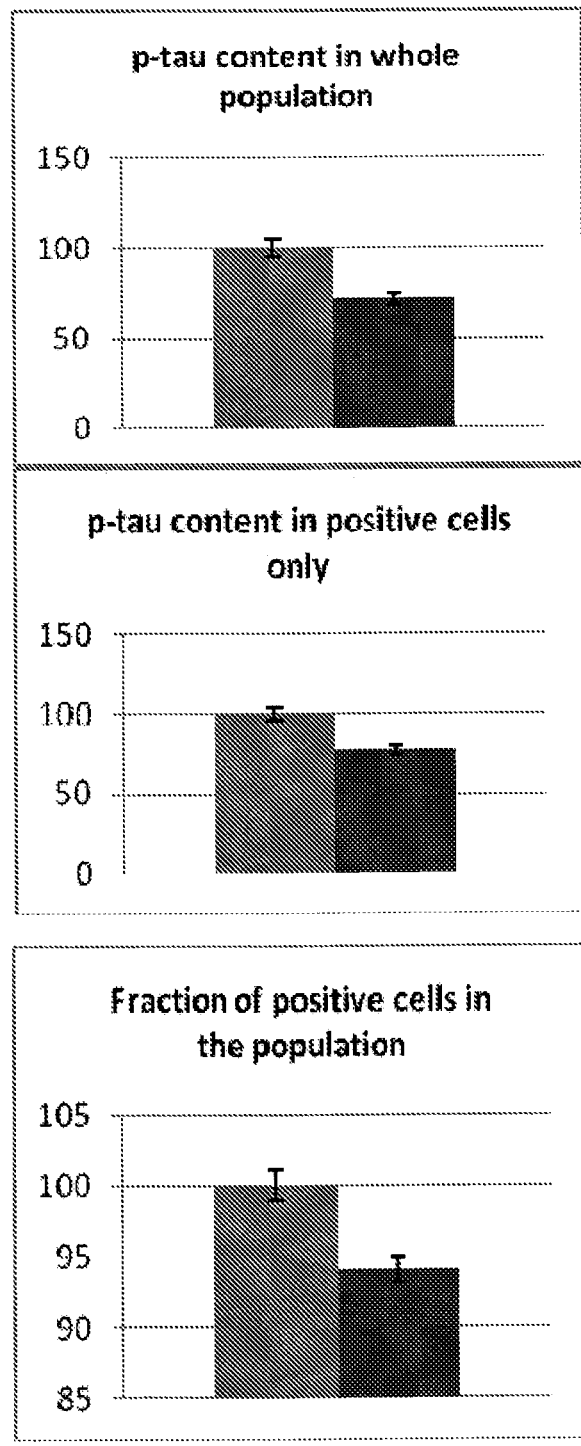
FIG. 3 Effect of rapamycin on p-tau expression in SH-SY5Y neuroblastoma cells. Grey bars=all single cells; Vertically-shaded bars=G1 population; Horizontally-shaded bars=G2 population; Lighter shading=control cells treated with culture medium; Darker shading=cells treated with 100 ng/ml rapamycin. All data are normalised to Control (100%).
Figure 3:
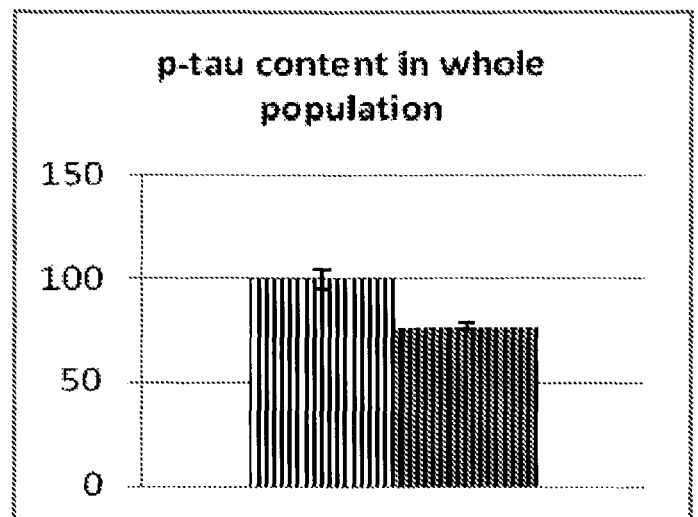
Figure 3:
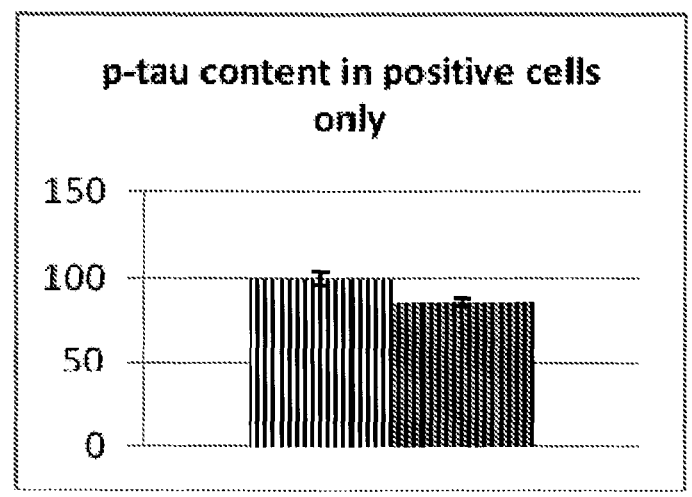
Figure 3:
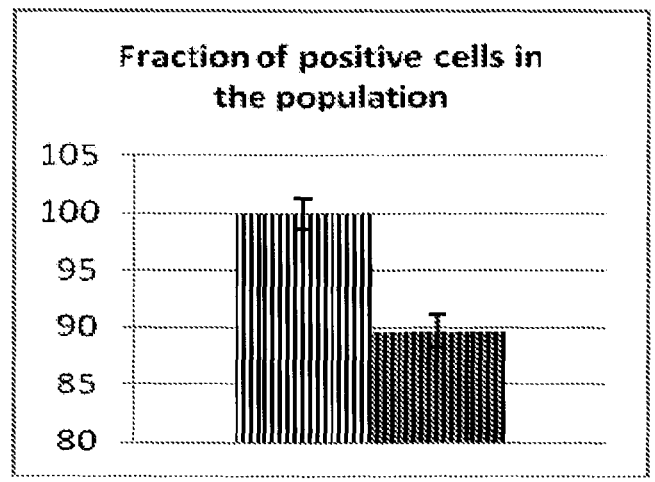
Figure 3:
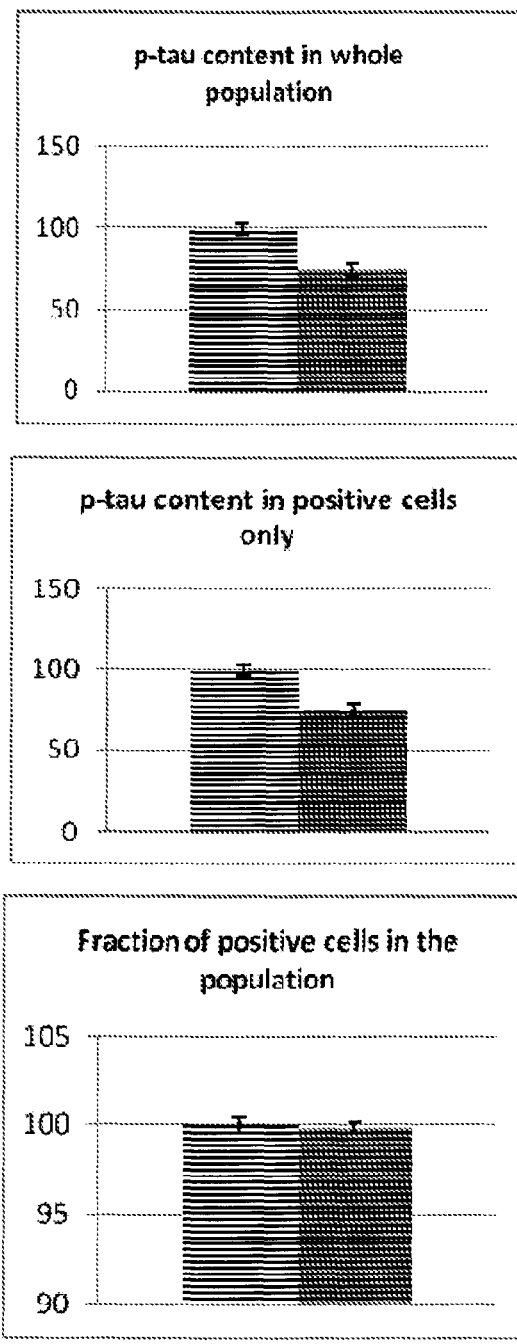

The effects of mTOR inhibition by rapamycin had the following effects. Firstly, the cell cycle kinetics were altered such that the G1 phase became longer and the G2 phase was shortened, as reflected by the accumulation of cells in the G1 phase of the cell cycle at the expense of the G2 phase (FIG. 2: Vertically shaded bars represent the G1 population; the horizontally shaded bars represent the G2 cell population. Lighter shades represent cells treated with Culture medium alone. Darker shades represent cells treated with Culture medium containing 100 ng/ml rapamycin. All data is normalised to Control (100%)). Secondly, the rapamycin induced a reduction of p-tau content in the whole cell culture. This is partly due to the alterations in cell cycle kinetics (reduction of the G2 cell population with the generally higher p-tau content). However, the rapamycin also had a cell cycle independent effect on p-tau leading to further reductions in this protein (FIG. 3: Grey bars represent all single cells; Vertically shaded bars represent the G1 population; the horizontally shaded bars represent the G2 cell population. Lighter shades represent cells treated with Culture medium alone. Darker shades represent cells treated with Culture medium containing 100 ng/ml rapamycin. All data are normalised to Control (100%)).

These findings indicate, in accordance with previous studies, that rapamycin is able to modulate the accumulation of AD-type p-tau both in a cell cycle dependent and independent manner.

The possibility that modulation of downstream effectors of mTOR (shown in Table 1) would have a similar effect to that observed with rapamycin was subsequently investigated.

2.2.2 CACNA1D

CACNA1D was not previously known to be a rapamycin-sensitive gene. Subsequently, the in silico molecular simulation of CACNA1D knockdown did not predict alteration in the expression of MAPT or APP.

Figure 4:
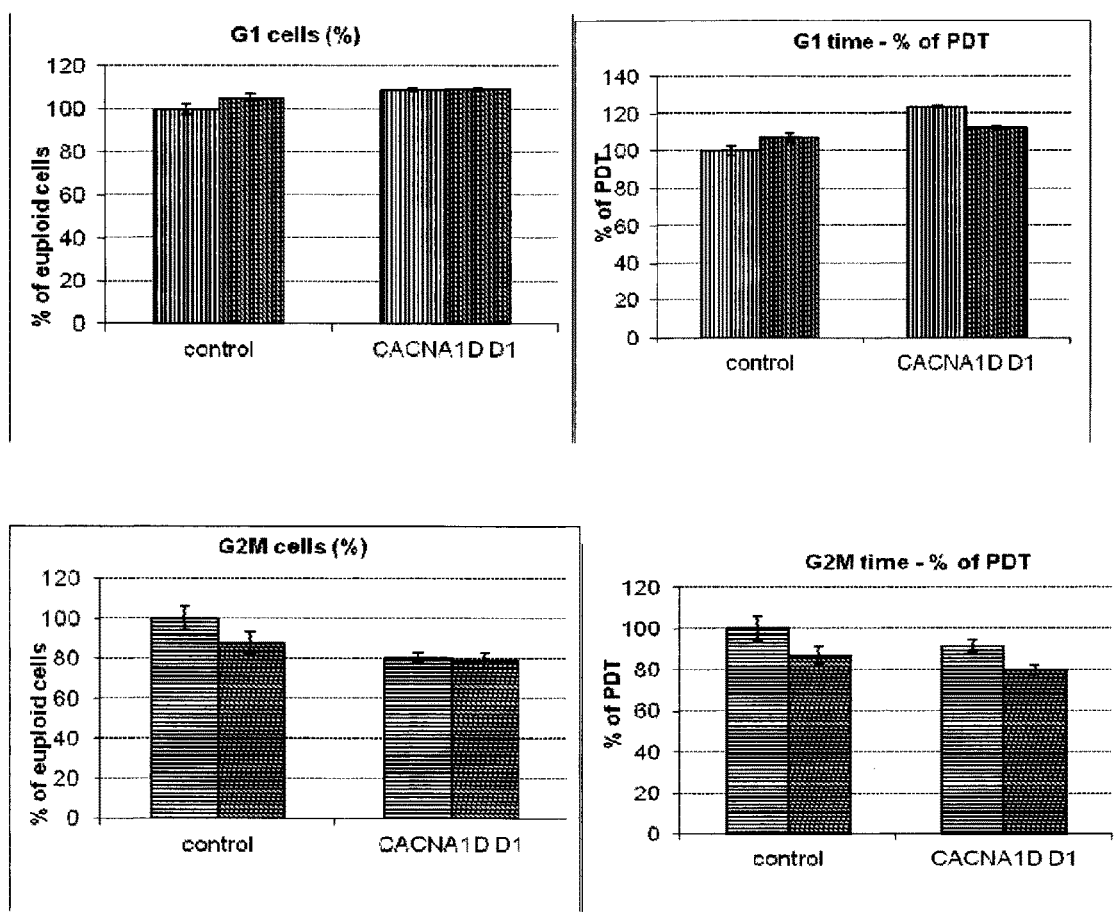
FIG. 4 Effect of siRNA-mediated down-regulation of CACNA1D on cell cycle kinetics in SH-SY5Y neuroblastoma cells. Vertically-shaded bars=G1 population; Horizontally-shaded bars=G2 population; Lighter shading=cells treated with Culture medium, siRNA Control and CACNA1D siRNA alone; Darker shading=cells treated with additional 100 ng/ml rapamycin.

However, the experimental data showed that the cell cycle effects of CACNA1D knock-down by siRNA were similar to that of rapamycin (FIG. 4: Vertically shaded bars represent the cell population in the G1 phase of the cell cycle, and the G1 time; horizontally shaded bars represent the cells in the G2 phase of the cell cycle and the G2 time. Lighter shades represent cells treated with Culture medium, siRNA control and CACNA1D siRNA alone. Darker shades represent cells treated with an additional 100 ng/ml rapamycin. All data is normalised to Control (100%)). The effect of CACNA1D knock-down by siRNA did not alter the effect of rapamycin. This is consistent with the cell cycle modulator effect of CACNA1D downstream of mTOR.

Figure 5:
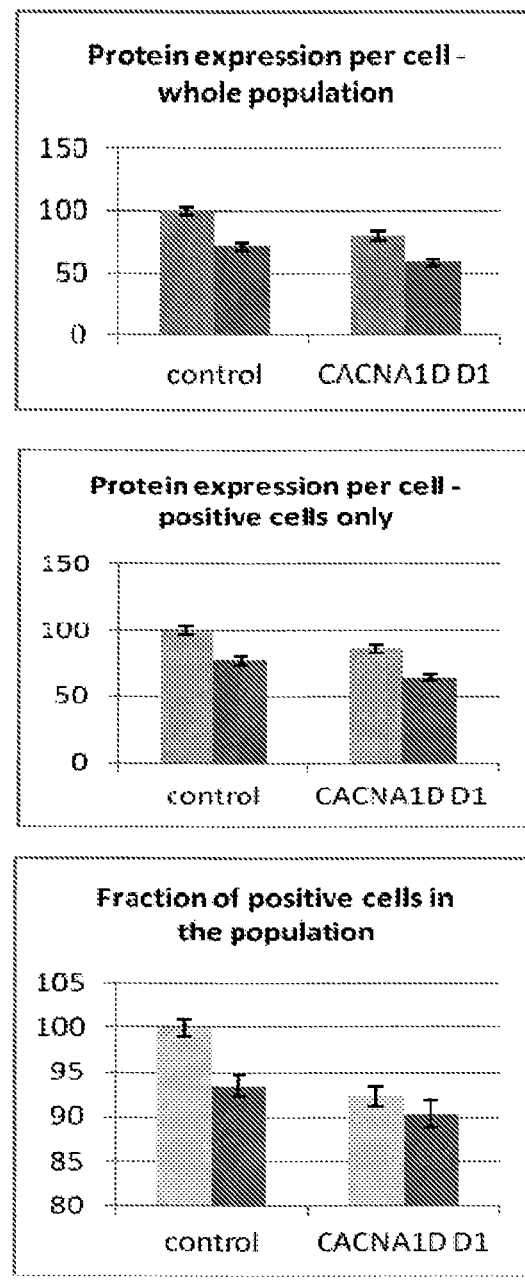
FIG. 5 Effect of siRNA-mediated down-regulation of CACNA1D on p-tau expression in SH-SY5Y neuroblastoma cells. Grey bars=all single cells; Vertically-shaded bars=G1 population; Horizontally-shaded bars=G2 population; Lighter shading=cells treated with Culture medium, siRNA Control and CACNA1D siRNA alone; Darker shades represent cells treated with additional 100 ng/ml rapamycin. All data are normalised to Control (100%).
Figure 5:
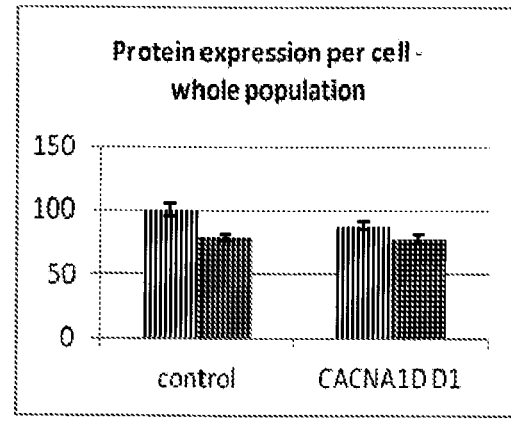
Figure 5:
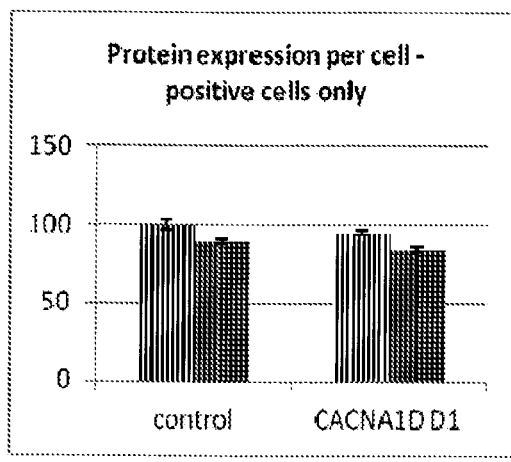
Figure 5:
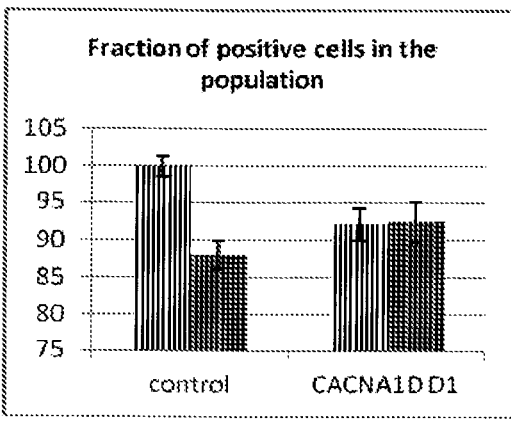
Figure 5:
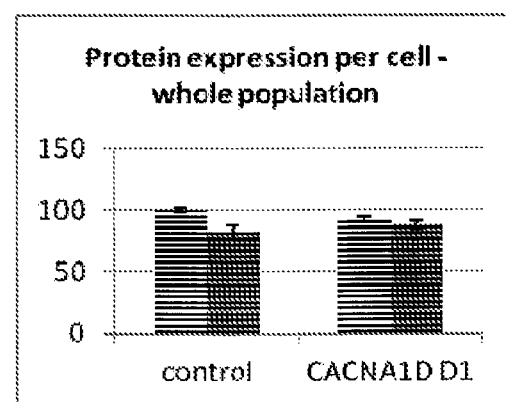
Figure 5:
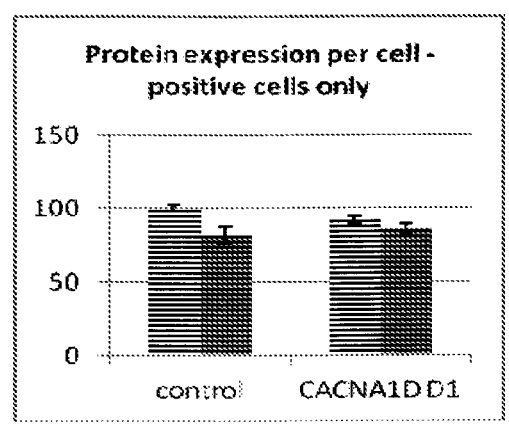
Figure 5:
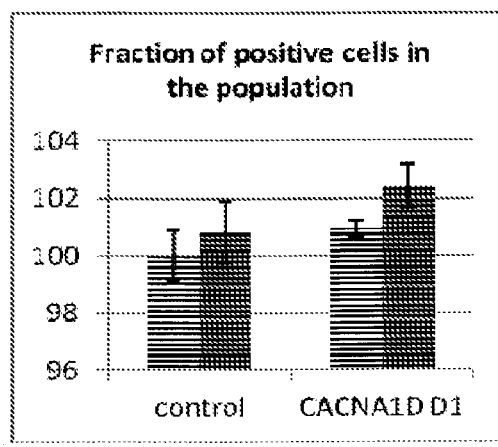

Protein expression analysis indicated that the effect of CACNA1D knockdown is similar to that induced by rapamycin. However, the CACNA1D knockdown did not alter the effect of rapamycin on p-tau expression in cells (FIG. 5: Grey bars represent all single cells; Vertically shaded bars represent the cell population in the G1 phase of the cell cycle; horizontally shaded bars represent the cells in the G2 phase of the cell cycle. Lighter shades represent cells treated with Culture medium, siRNA Control and CACNA1D siRNA alone. Darker shades represent cells treated with additional 100 ng/ml rapamycin. All data are normalised to Control (100%)).

The data provide evidence that, contrary to prior knowledge, the CACNA1D gene expression is mTOR dependent. The data also provide evidence that modulation of CACNA1D has a similar effect to rapamycin in terms of cell cycle and AD-related p-tau expression.

The data provide evidence that the modulation of a downstream effector of mTOR has the same beneficial effect on AD-related cell cycle and protein changes as rapamycin.
2.2.3 GABBR2

The GABBR2 receptor has not previously been identified as a downstream effector of mTOR i.e. is not a known rapamycin-sensitive gene. Thus the in silico simulation of GABBR2 receptor knockdown did not predict a similar effect to rapamycin with respect to AD-related protein expression.

Figure 6:
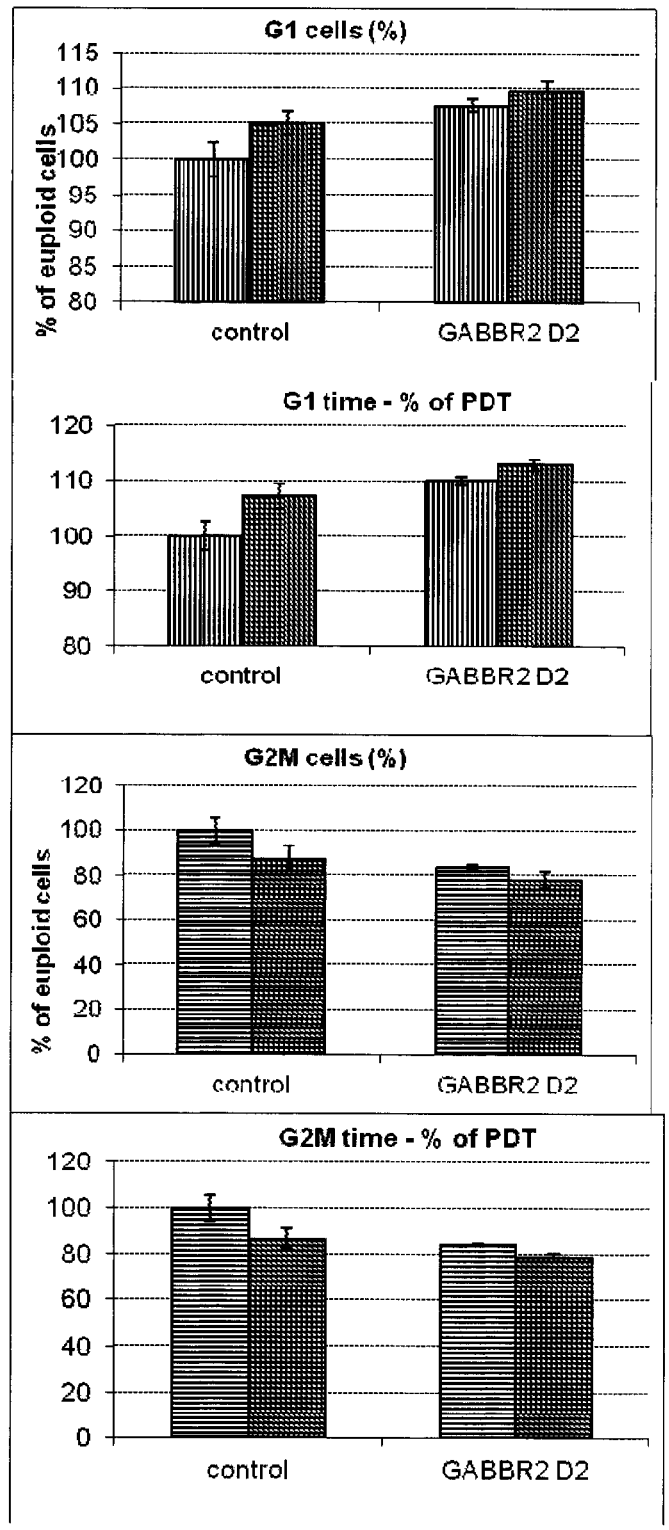
FIG. 6 Effect of siRNA-mediated down-regulation of GABBR2 on cell cycle kinetics in SH-SY5Y neuroblastoma cells. Vertically-shaded bars=G1 population; Horizontally-shaded bars=G2 population; Lighter shading=cells treated with Culture medium, siRNA Control and GABBR2 siRNA alone; Darker shading=cells treated with additional 100 ng/ml rapamycin.

However, the effects of GABBR2 knockdown by siRNA in the experimental model were similar to that of rapamycin. The GABBR2 knockdown did not affect the rapamycin response significantly (FIG. 6: Vertically shaded bars represent the cell population in the G1 phase of the cell cycle, and the G1 time; horizontally shaded bars represent the cells in the G2 phase of the cell cycle and the G2 time. Lighter shades represent cells treated with Culture medium, siRNA Control and GABBR2 siRNA alone. Darker shades represent cells treated with additional 100 ng/ml rapamycin. All data is normalised to Control (100%)). These data are consistent with the cell cycle modulator effect of GABBR2 downstream of mTOR.

Figure 7:
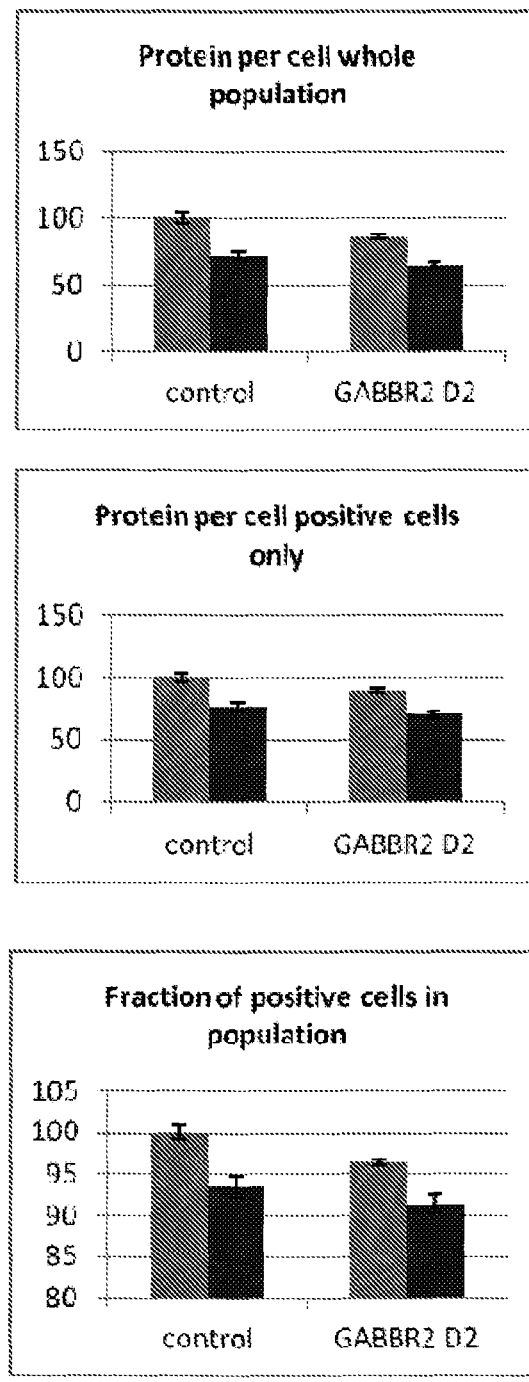
FIG. 7 Effect of siRNA-mediated down-regulation of GABBR2 on p-tau expression in SH-SY5Y neuroblastoma cells. Grey bars=all single cells; Vertically-shaded bars=G1 population; Horizontally-shaded bars=G2 population; Lighter shading=cells treated with Culture medium, siRNA Control and GABBR2 siRNA alone; Darker shades represent cells treated with additional 100 ng/ml rapamycin. All data are normalised to Control (100%).
Figure 7:
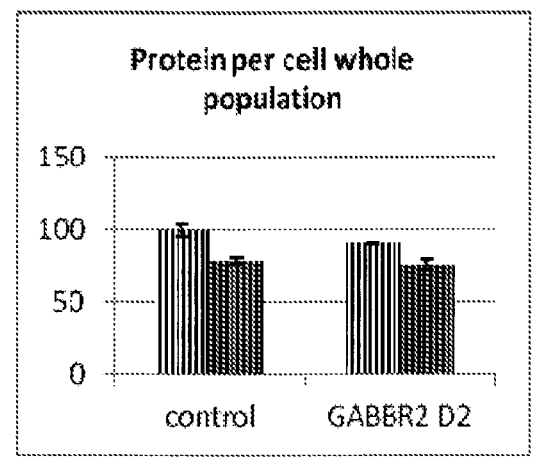
Figure 7:
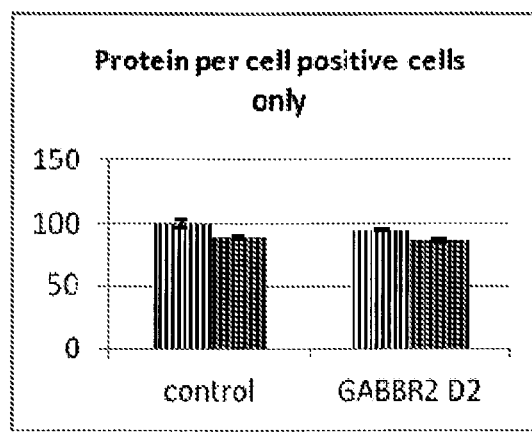
Figure 7:
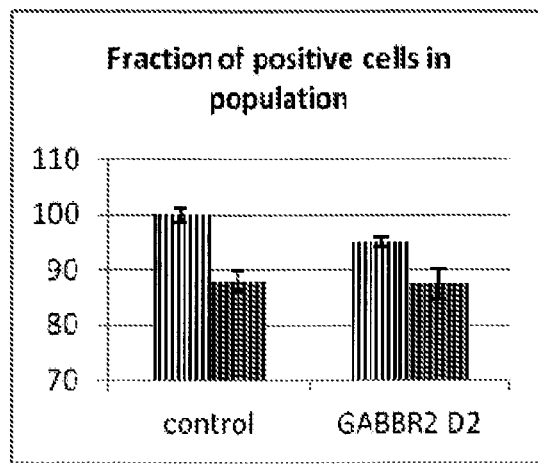
Figure 7:
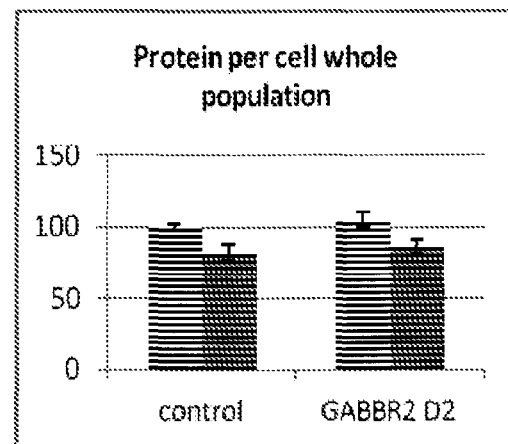
Figure 7:
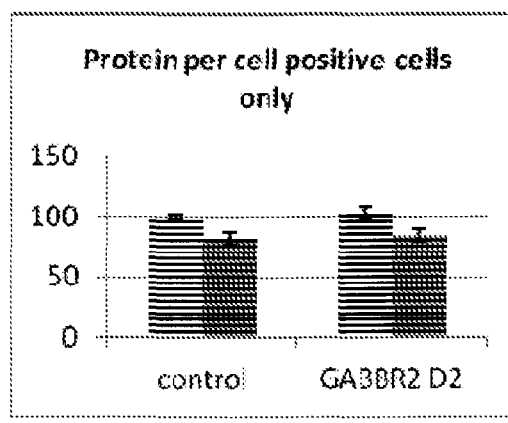
Figure 7:
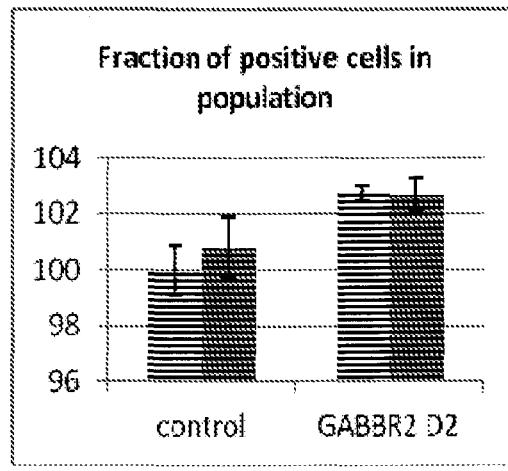

The effect of GABBR2 knockdown on p-tau expression was similar to that induced by rapamycin, albeit weaker. However, in the presence of rapamycin, GABBR2 knockdown had no further significant effect on p-tau expression in cells (FIG. 7: Grey bars represent all single cells; vertically shaded bars represent the cell population in the G1 phase of the cell cycle; horizontally shaded bars represent the cells in the G2 phase of the cell cycle. Lighter shades represent cells treated with Culture medium, siRNA Control and GABBR2 siRNA alone. Darker shades represent cells treated with additional 100 ng/ml rapamycin. All data are normalised to Control (100%)).

The data provide evidence that, contrary to prior knowledge, the GABBR2 gene expression is mTOR dependent. The data also provide evidence that modulation of GABBR2 has a similar effect to rapamycin in terms of cell cycle and AD-related p-tau expression.

The data provides evidence that the modulation of a downstream effector of mTOR has the same beneficial effect on AD-related cell cycle and protein changes as rapamycin.
2.2.4 HOXD10

The HOXD10 gene was not previously known to be rapmycin-sensitive. Thus the in silico simulation of HOXD10 knockdown did not predict a similar effect to rapamycin with respect to AD-related protein expression.

Figure 8:
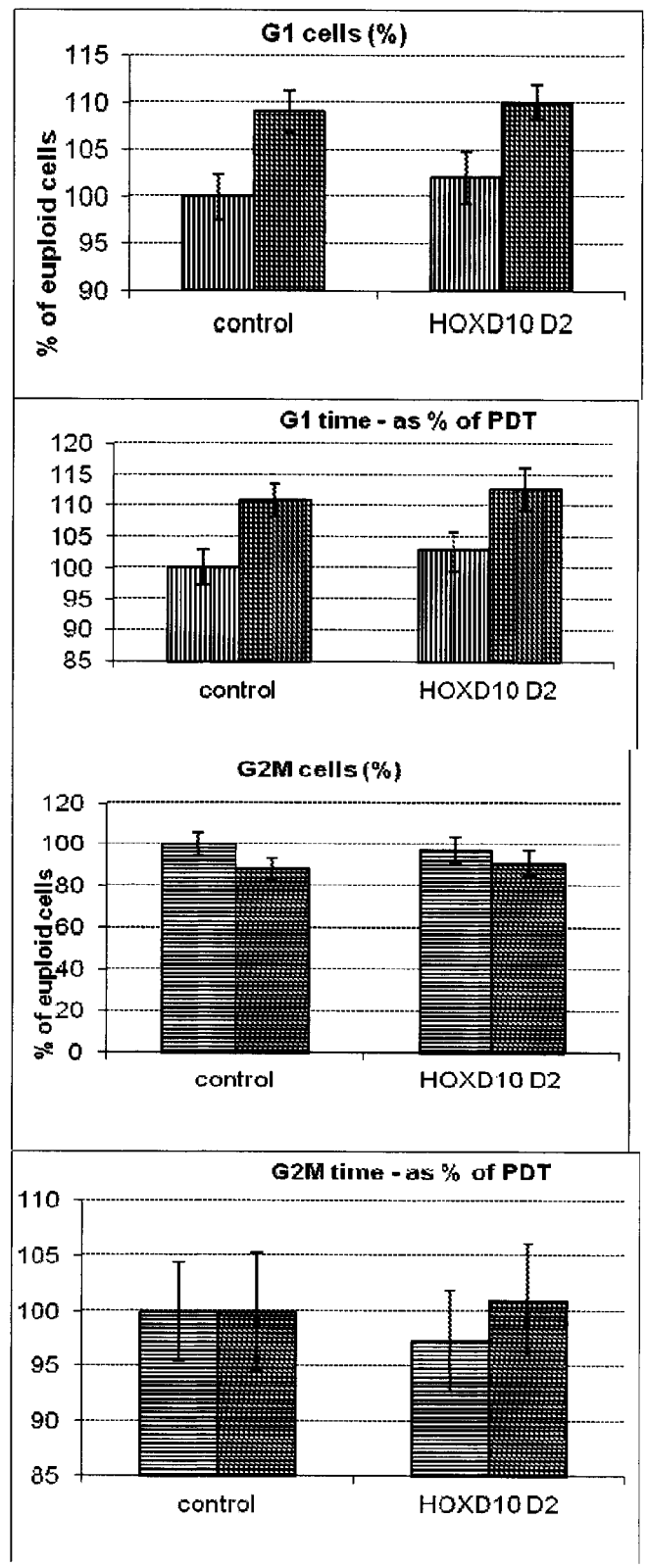
FIG. 8 Effect of siRNA-mediated down-regulation of HOXD10 on cell cycle kinetics in SH-SY5Y neuroblastoma cells. Vertically-shaded bars=G1 population; Horizontally-shaded bars=G2 population; Lighter shading=cells treated with Culture medium, siRNA Control and HOXD10 siRNA alone; Darker shading=cells treated with additional 100 ng/ml rapamycin.

In the experimental model, the siRNA to HOX10D did not affect the cell cycle in a similar fashion to rapamycin (FIG. 8: Vertically shaded bars represent the cell population in the G1 phase of the cell cycle, and the G1 time; horizontally shaded bars represent the cells in the G2 phase of the cell cycle and the G2 time. Lighter shades represent cells treated with Culture medium, siRNA Control and HOX10D siRNA alone. Darker shades represent cells treated with additional 100 ng/ml rapamycin. All data are normalised to Control (100%)). However, rapamycin was able to exert its cell cycle modulator effect even when HOX10D was not expressed (FIG. 8). This would indicate that HOX10D does not play a role in the rapamycin induced cell cycle modulation.

Figure 9:
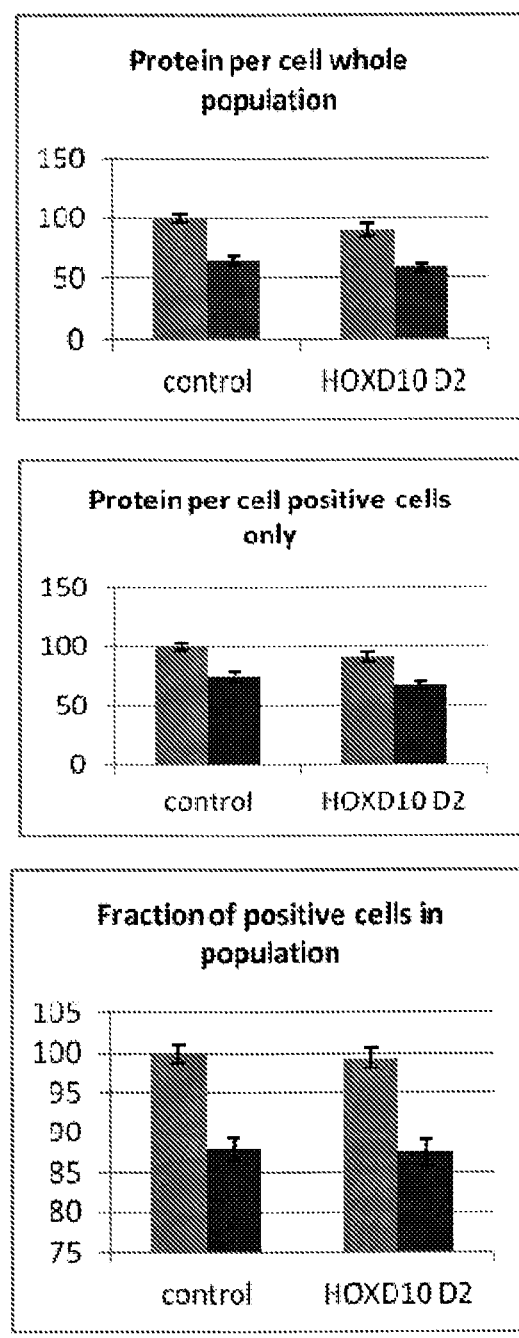
FIG. 9 Effect of siRNA-mediated down-regulation of HOXD10 on p-tau expression in SH-SY5Y neuroblastoma cells. Grey bars=all single cells; Vertically-shaded bars=G1 population; Horizontally-shaded bars=G2 population; Lighter shading=cells treated with Culture medium, siRNA Control and HOXD10 siRNA alone; Darker shades represent cells treated with additional 100 ng/ml rapamycin. All data are normalised to Control (100%).
Figure 9:
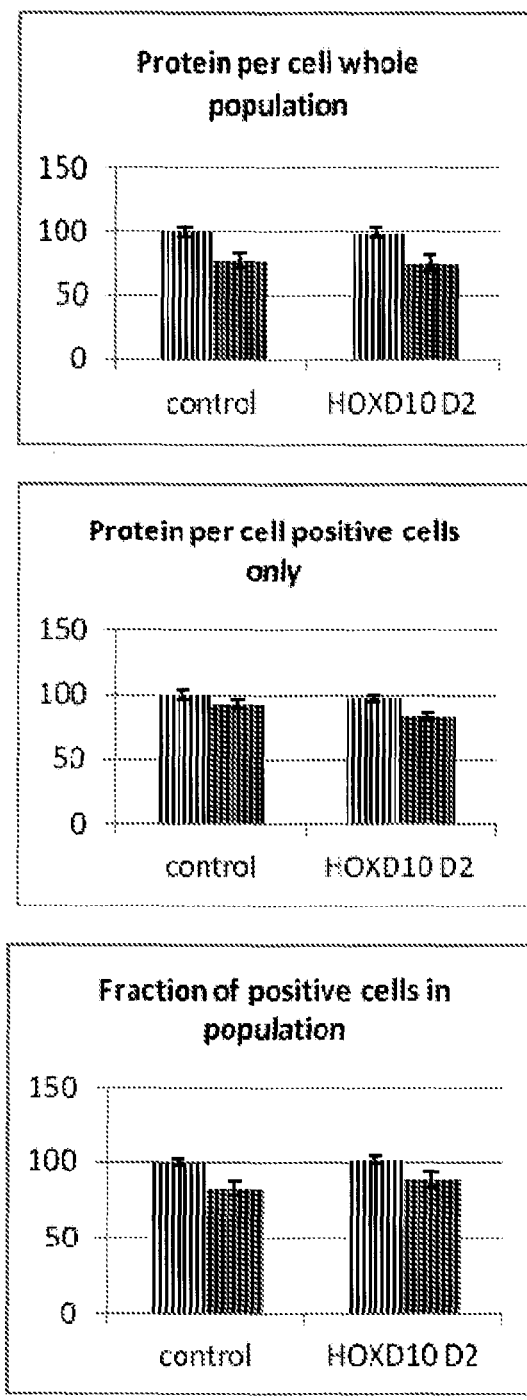
Figure 9:
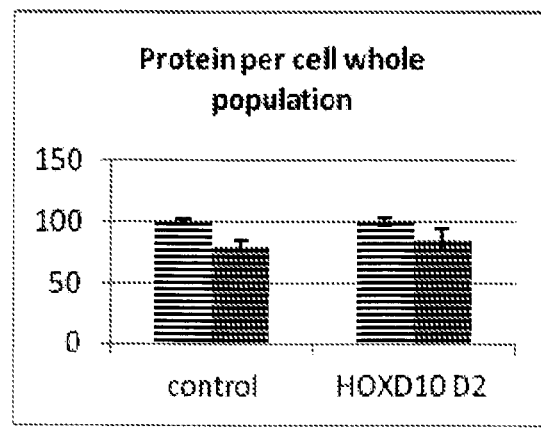
Figure 9:
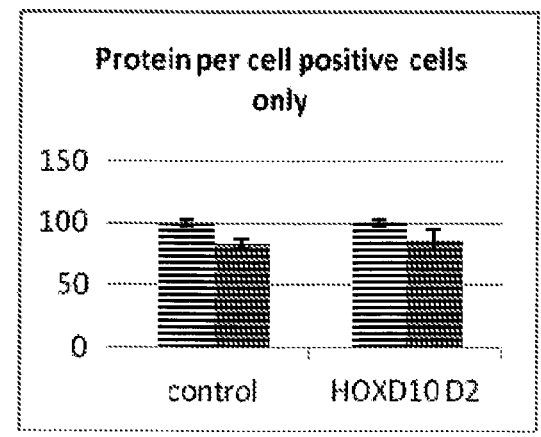
Figure 9:
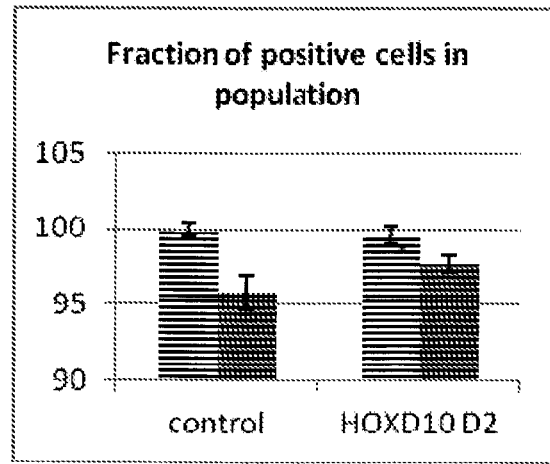

HOX10D knockdown had a weak effect in reducing p-tau expression in the cellular model, mainly by reducing the amount of p-tau in the G1 cell population. The effects were significantly weaker than that of rapamycin and the HOXD10 knockdown did not affect the rapamycin effect (FIG. 9: Grey bars represent all single cells; Vertically shaded bars represent the cell population in the G1 phase of the cell cycle; horizontally shaded bars represent the cells in the G2 phase of the cell cycle. Lighter shades represent cells treated with Culture medium, siRNA Control and HOX10D siRNA alone. Darker shades represent cells treated with additional 100 ng/ml rapamycin. All data are normalised to Control (100%)). The data provide evidence that the modulation of a downstream effector of mTOR has the same beneficial effect on AD-related protein changes as rapamycin.
2.2.5 KLF2

Although KLF2 was not previously identified as a rapamycin-sensitive gene, the indirect molecular interactions allowed the simulation of the effect of mTOR on KLF2. However, in AD the expression of KLF2 was found to be opposite to what would normally be expected in response to mTOR activation. The effects of KLF2 knockdown in the AD brain were simulated, and found to closely mimic the effects of rapamycin in terms of AD-related protein expression (MAPT and APP).

Figure 10:
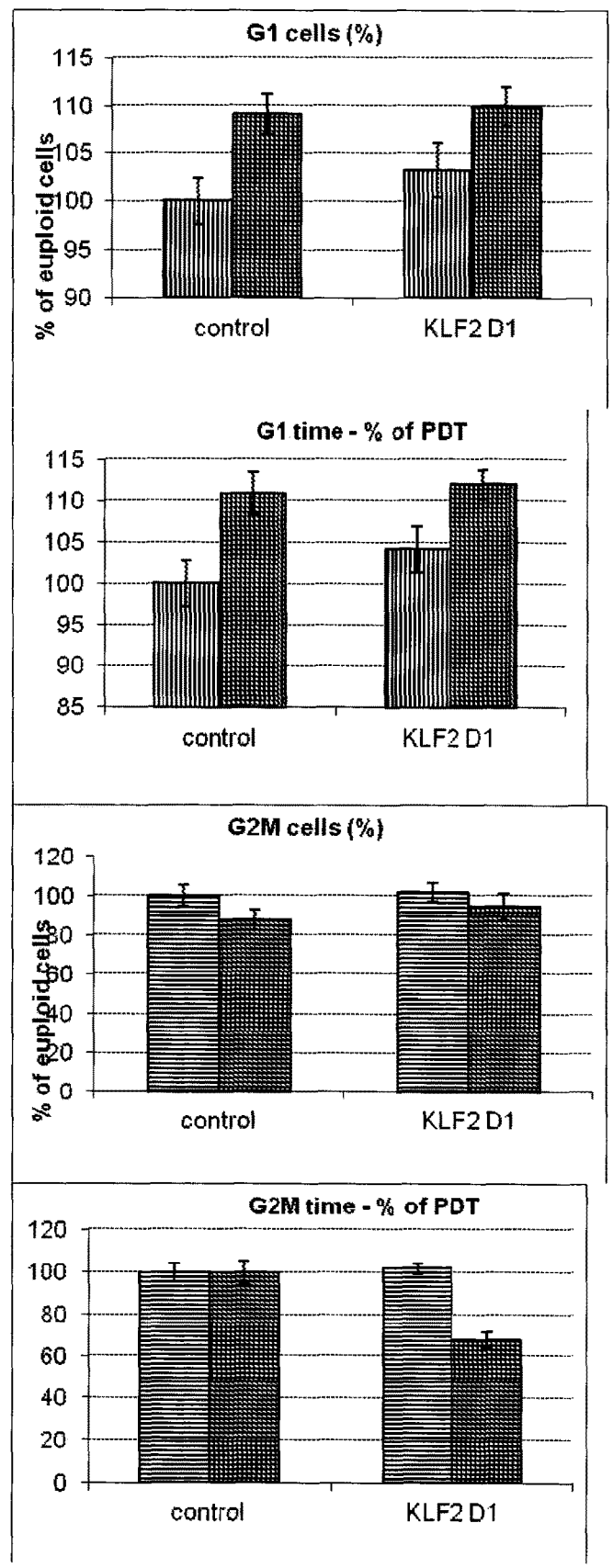
FIG. 10 Effect of siRNA-mediated down-regulation of KLF2 on cell cycle kinetics in SH-SY5Y neuroblastoma cells. Vertically-shaded bars=G1 population; Horizontally-shaded bars=G2 population; Lighter shading=cells treated with Culture medium, siRNA Control and KLF2 siRNA alone; Darker shading=cells treated with additional 100 ng/ml rapamycin.

In the experimental model, the knockdown of KLF2 produced similar but weaker cell cycle effects relative to rapamycin. The KLF2 knockdown did not affect significantly the effect of rapamycin on the G1 phase of the cell cycle. However, the KLF2 knockdown led to a significant alteration of the G2 effect of rapamycin (FIG. 10: Vertically shaded bars represent the cell population in the G1 phase of the cell cycle, and the G1 time; horizontally shaded bars represent the cells in the G2 phase of the cell cycle and the G2 time. Lighter shades represent cells treated with Culture medium, siRNA Control and KLF2 siRNA alone. Darker shades represent cells treated with additional 100 ng/ml rapamycin. All data are normalised to Control (100%)). The data indicate that KLF2 is a downstream effector of the mTOR induced cell cycle response and it is essential for the G2 regulator effects of mTOR.

Figure 11:
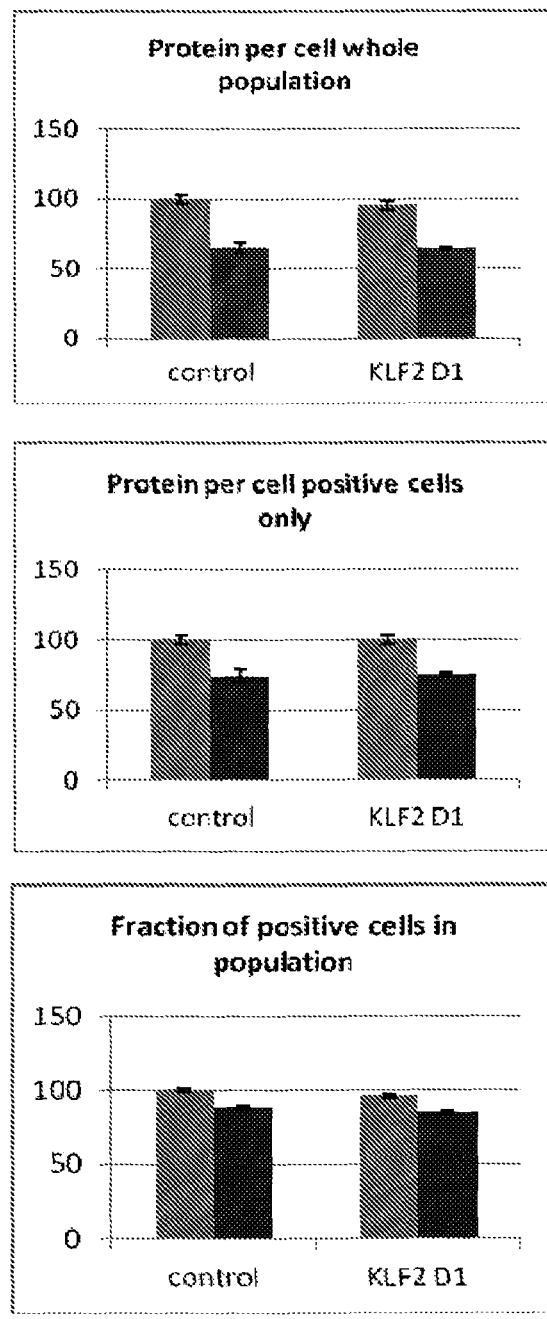
FIG. 11 Effect of siRNA-mediated down-regulation of KLF2 on p-tau expression in SH-SY5Y neuroblastoma cells. Grey bars=all single cells; Vertically-shaded bars=G1 population; Horizontally-shaded bars=G2 population; Lighter shading=cells treated with Culture medium, siRNA Control and KLF2 siRNA alone; Darker shades represent cells treated with additional 100 ng/ml rapamycin. All data are normalised to Control (100%).
Figure 11:
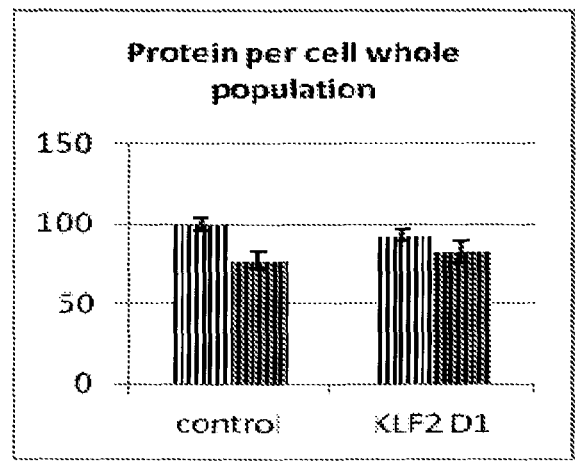
Figure 11:
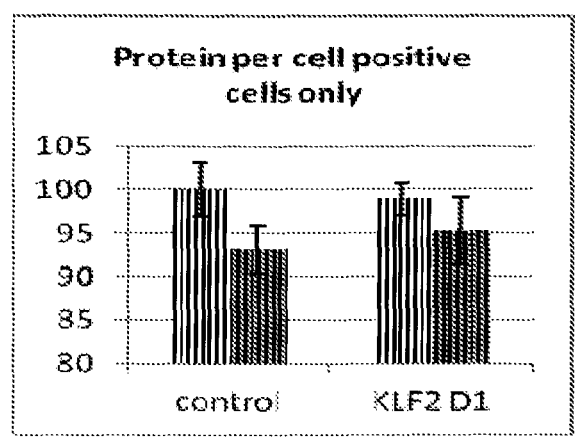
Figure 11:
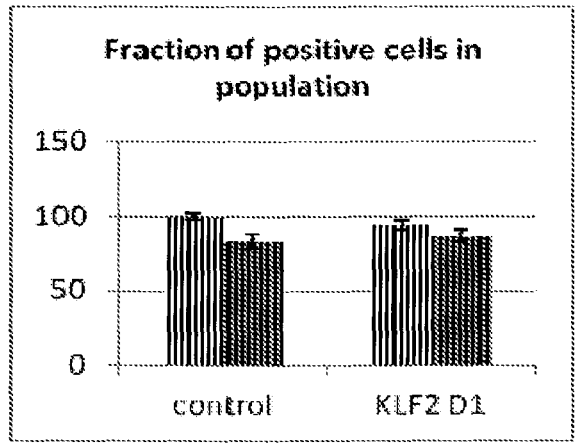
Figure 11:
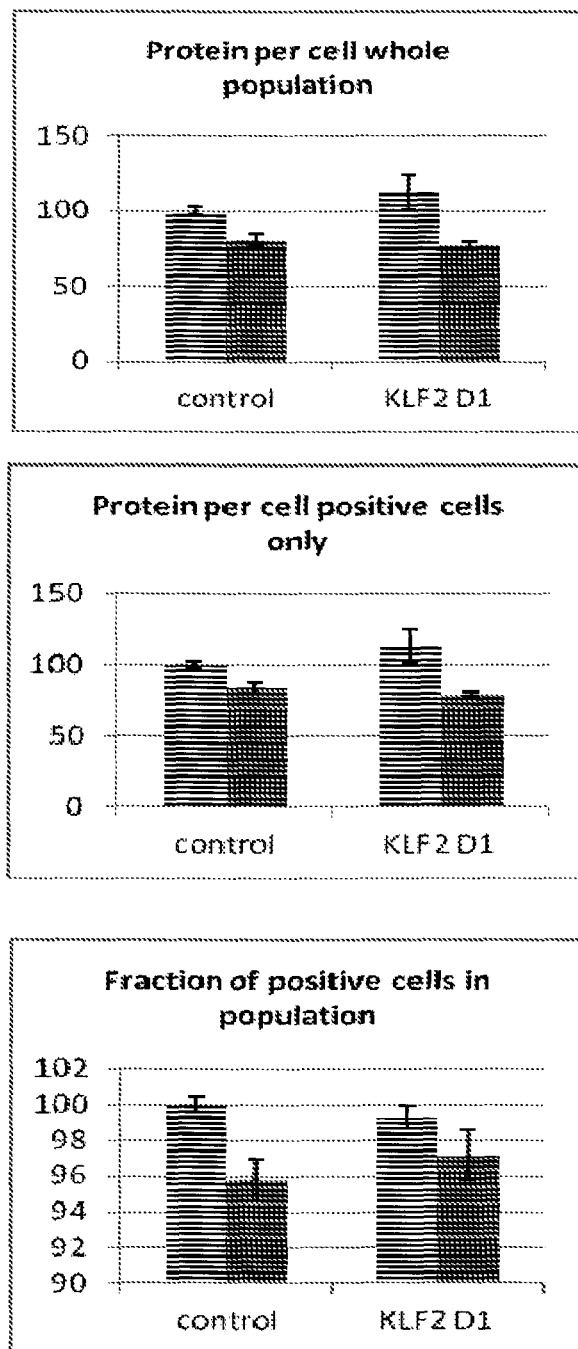

The effects of KLF2 knockdown on p-tau expression were similar to those of rapamycin, albeit a lot weaker. The KLF2 knockdown did not affect the rapamycin effect on p-tau expression (FIG. 11: Grey bars represent all single cells; Vertically shaded bars represent the cell population in the G1 phase of the cell cycle; horizontally shaded bars represent the cells in the G2 phase of the cell cycle. Lighter shades represent cells treated with Culture medium, siRNA Control and KLF2 siRNA alone. Darker shades represent cells treated with additional 100 ng/ml rapamycin. All data are normalised to Control (100%)).

These data also indicate that the modulation of a rapamycin-sensitive gene will lead to effects that are similar to rapamycin.

2.2.6 RHO

RHO was not previously known to be a rapamycin-sensitive gene. However, the molecular interactions of RHO allowed the simulation of the effect of RHO knockdown in the AD brain. The in silico simulation indicated that RHO knockdown will lead to changes in the AD-related molecules (MAPT and APP) similar to that seen with Rapamycin.

Figure 12:
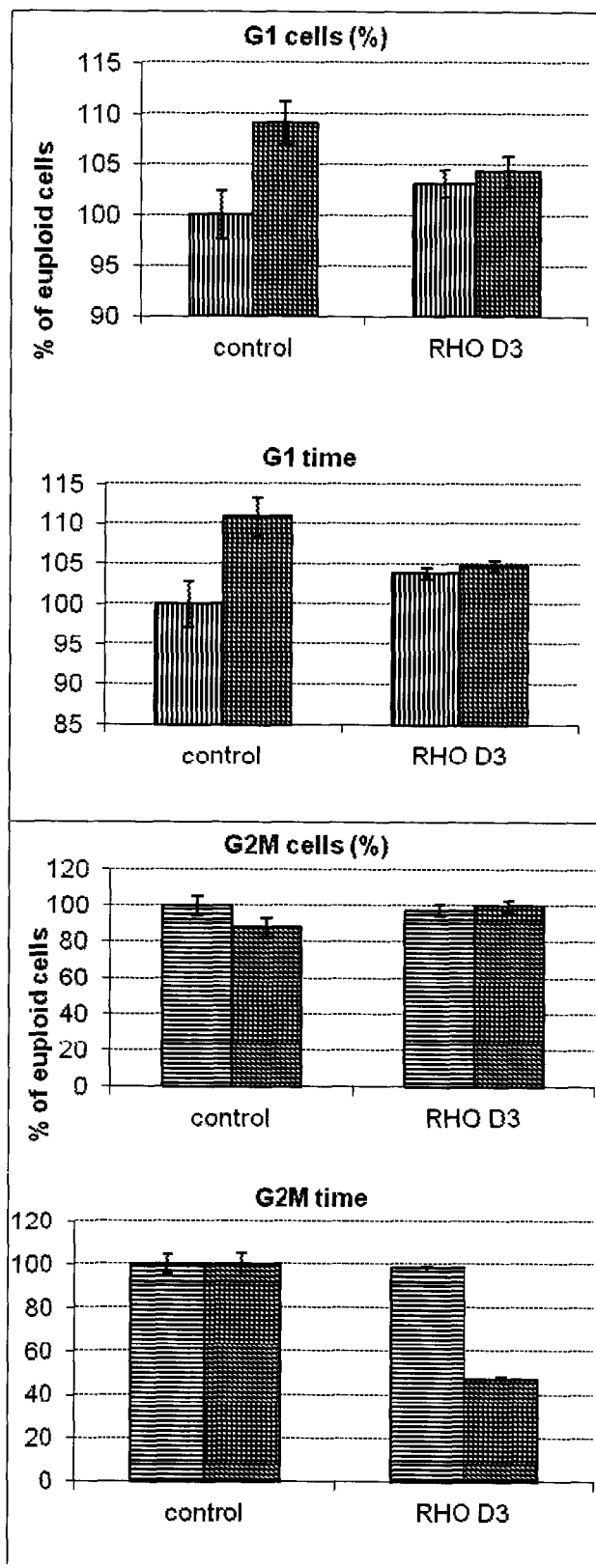
FIG. 12 Effect of siRNA-mediated down-regulation of RHO on cell cycle kinetics in SH-SY5Y neuroblastoma cells. Vertically-shaded bars=G1 population; Horizontally-shaded bars=G2 population; Lighter shading=cells treated with Culture medium, siRNA Control and RHO siRNA alone; Darker shading=cells treated with additional 100 ng/ml rapamycin.

In the experimental model the knockdown of RHO produced similar, but weaker cell cycle effects relative to rapamycin. The RHO knockdown did not affect significantly the effect of rapamycin on the G1 phase of the cell cycle. However, the RHO knockdown led to a significant alteration of the G2 effect of rapamycin (FIG. 12: Vertically shaded bars represent the cell population in the G1 phase of the cell cycle, and the G1 time; horizontally shaded bars represent the cells in the G2 phase of the cell cycle and the G2 time. Lighter shades represent cells treated with Culture medium, siRNA Control and RHO siRNA alone. Darker shades represent cells treated with additional 100 ng/ml rapamycin. All data are normalised to Control (100%)). The data indicate that RHO is a downstream effector of the mTOR induced cell cycle response and it is essential for the G2 regulator effects of mTOR.

Figure 13:
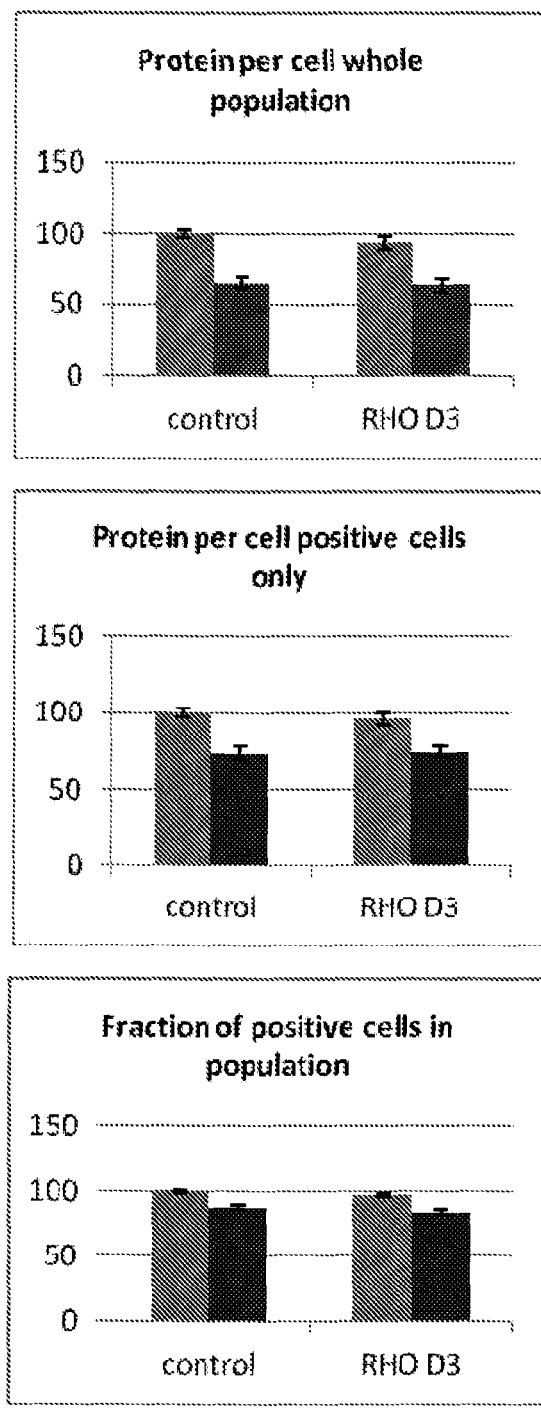
FIG. 13 Effect of siRNA-mediated down-regulation of RHO on p-tau expression in SH-SY5Y neuroblastoma cells. Grey bars=all single cells; Vertically-shaded bars=G1 population; Horizontally-shaded bars=G2 population; Lighter shading=cells treated with Culture medium, siRNA Control and RHO siRNA alone; Darker shades represent cells treated with additional 100 ng/ml rapamycin. All data are normalised to Control (100%).
Figure 13:
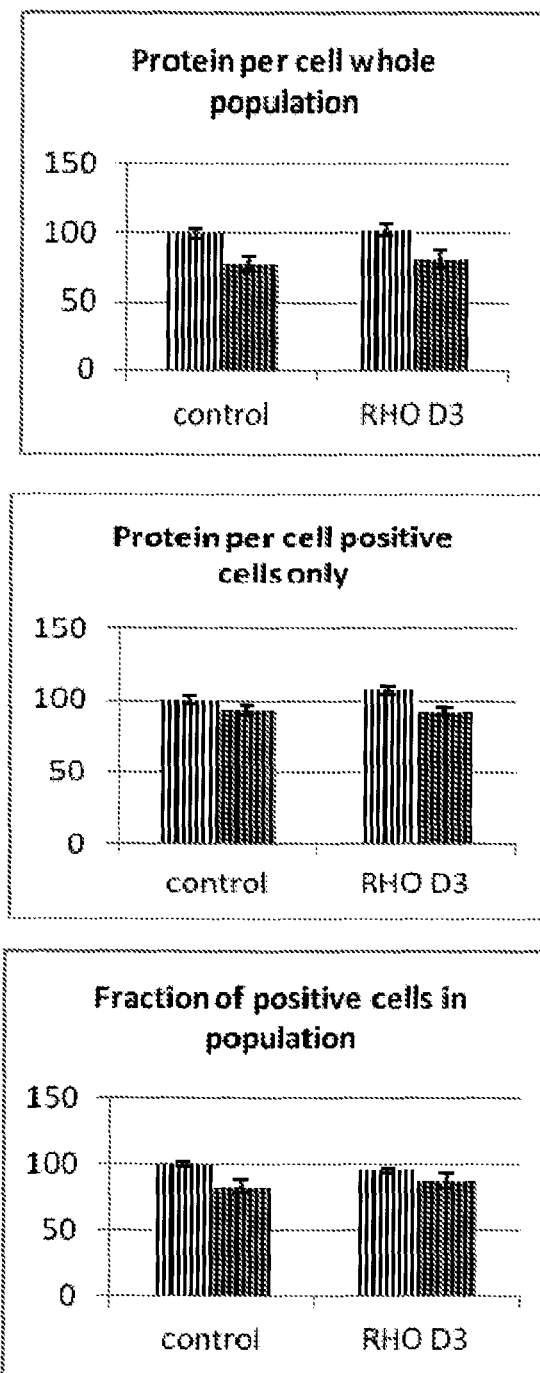
Figure 13:
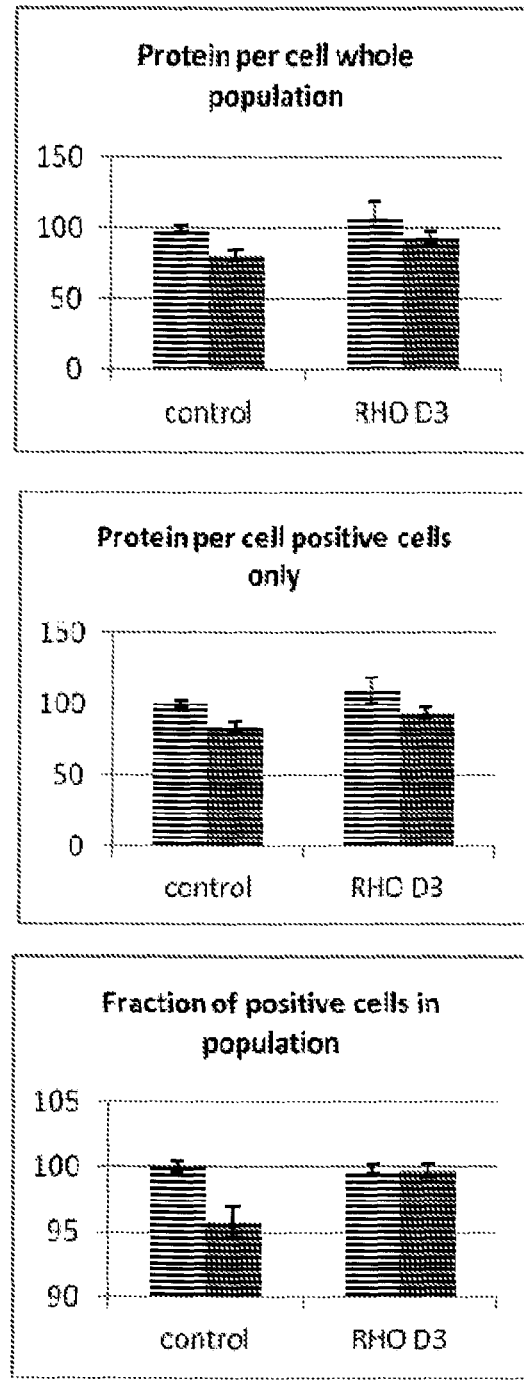

The effects of RHO knockdown on p-tau expression were similar to those of rapamycin, albeit a lot weaker. The RHO knockdown did not affect the rapamycin effect on p-tau expression (FIG. 13: Grey bars represent all single cells; Vertically shaded bars represent the cell population in the G1 phase of the cell cycle; horizontally shaded bars represent the cells in the G2 phase of the cell cycle. Lighter shades represent cells treated with Culture medium, siRNA Control and RHO siRNA alone. Darker shades represent cells treated with additional 100 ng/ml rapamycin. All data are normalised to Control (100%)). These data are consistent with RHO acting downstream of mTOR.

The data also indicate that the modulation of a rapamycin-sensitive gene will lead to effects that are similar to rapamycin.

2.2.7 GLI2

Based on known molecular interactions it could be predicted in silico that GL12 (although not previously identified as a rapamycin-sensitive gene) would be differentially regulated by mTOR activation. The AD brain expression studies however indicated that the expression of GL12 is not consistent with the activation of mTOR. The in silico simulations carried out to predict the effects of GL12 knockdown in the AD brain indicated that the knockdown of GL12 would lead to effects that are very similar to that of rapamycin in terms of AD-related protein (MAPT and APP) expression in the brain.

Figure 14:
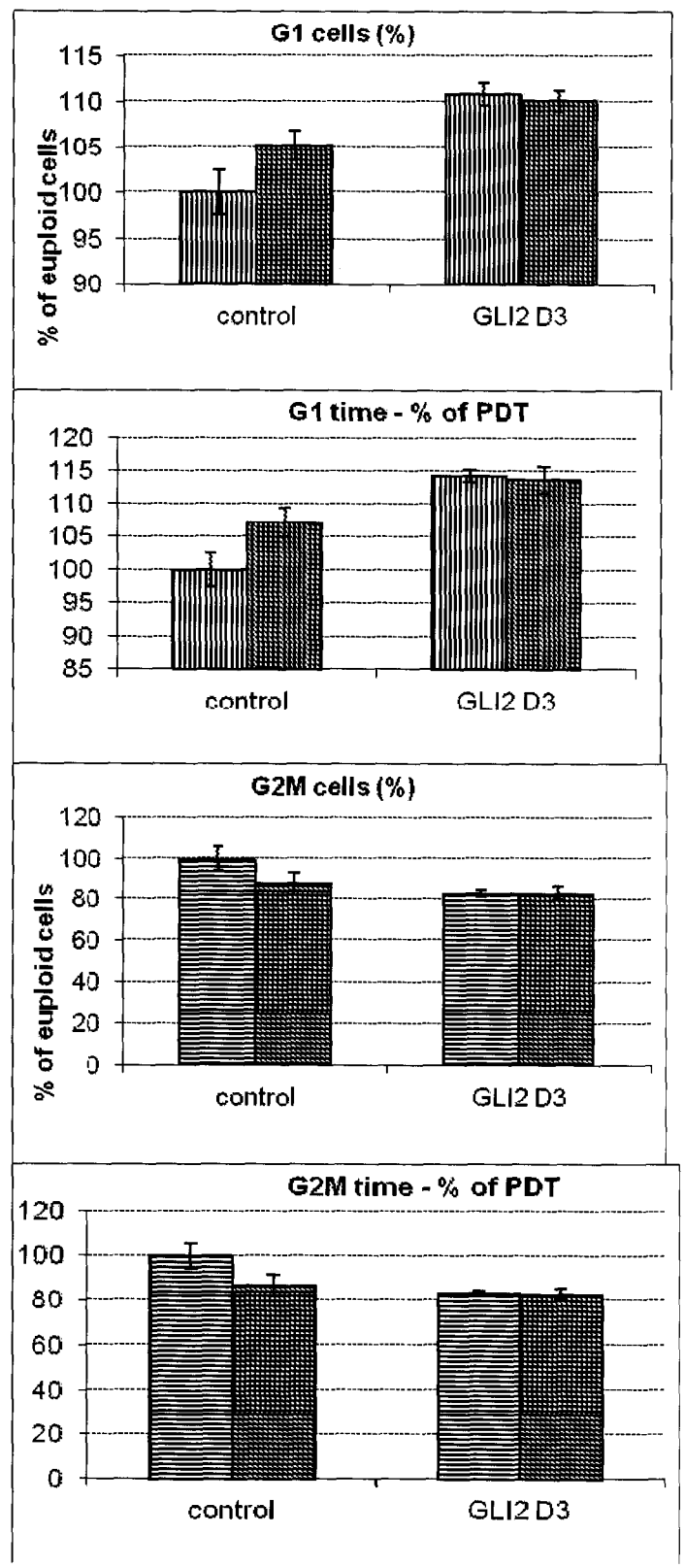
FIG. 14 Effect of siRNA-mediated down-regulation of GL12 on cell cycle kinetics in SH-SY5Y neuroblastoma cells. Vertically-shaded bars=G1 population; Horizontally-shaded bars=G2 population; Lighter shading=cells treated with Culture medium, siRNA Control and GL12 siRNA alone; Darker shading=cells treated with additional 100 ng/ml rapamycin.

The effects of GL12 knockdown by siRNA on the cell cycle were similar to that of rapamycin, but had no effect on rapamycin response (FIG. 14: Vertically shaded bars represent the cell population in the G1 phase of the cell cycle, and the G1 time; horizontally shaded bars represent the cells in the G2 phase of the cell cycle and the G2 time. Lighter shades represent cells treated with Culture medium, siRNA Control and GL12 siRNA alone. Darker shades represent cells treated with additional 100 ng/ml rapamycin. All data are normalised to Control (100%)).

Figure 15:
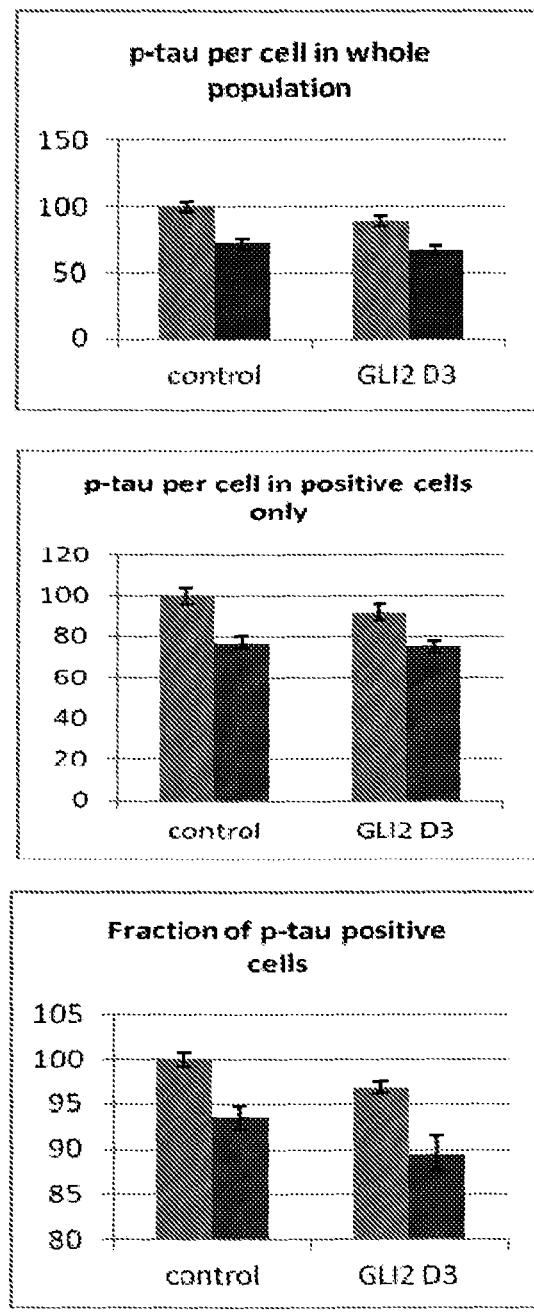
FIG. 15 Effect of siRNA-mediated down-regulation of GL12 on p-tau expression in SH-SY5Y neuroblastoma cells. Grey bars=all single cells; Vertically-shaded bars=G1 population; Horizontally-shaded bars=G2 population; Lighter shading=cells treated with Culture medium, siRNA Control and GL12 siRNA alone; Darker shades represent cells treated with additional 100 ng/ml rapamycin. All data are normalised to Control (100%).
Figure 15:
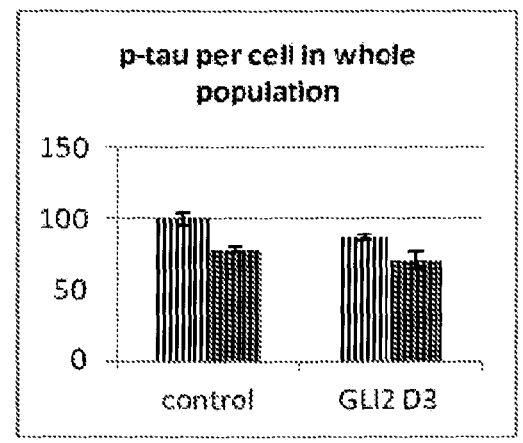
Figure 15:
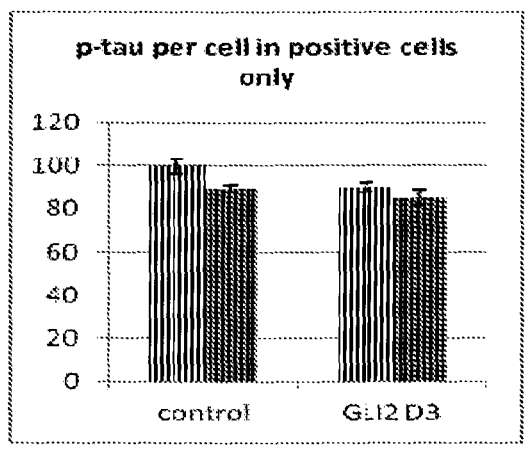
Figure 15:
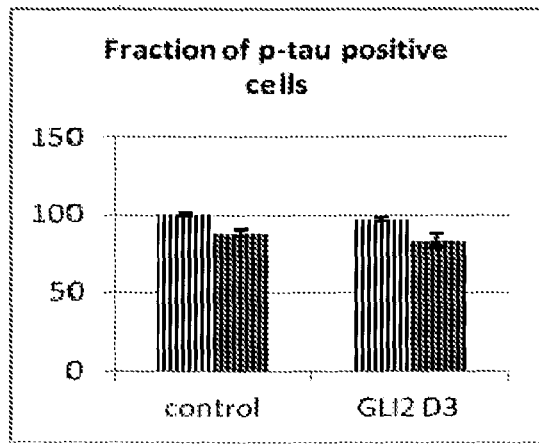
Figure 15:
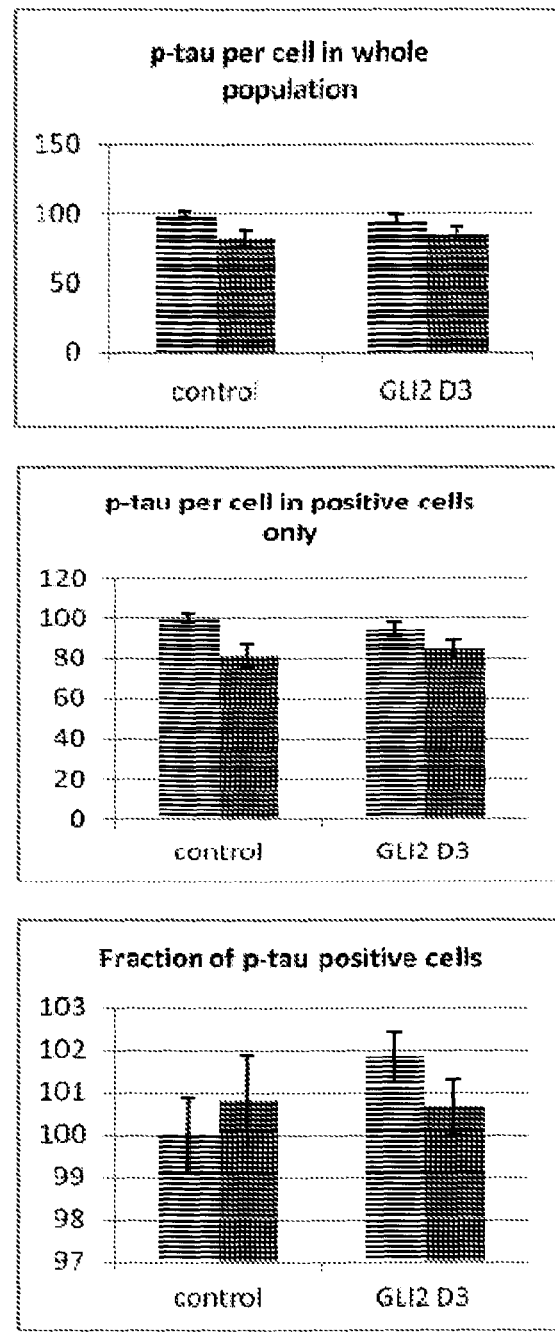

The data indicate that in the absence of rapamycin the effect of GL12 knockdown is similar to that induced by rapamycin, albeit weaker (FIG. 15: Grey bars represent all single cells; Vertically shaded bars represent the cell population in the G1 phase of the cell cycle; horizontally shaded bars represent the cells in the G2 phase of the cell cycle. Lighter shades represent cells treated with Culture medium, siRNA Control and GL12 siRNA alone. Darker shades represent cells treated with additional 100 ng/ml rapamycin. All data are normalised to Control (100%)). However, in the presence of rapamycin GL12 knockdown had no further significant effect on p-tau expression in cells.

The data provide evidence that modulation of GL12 has a similar effect to rapamycin in terms of cell cycle and AD-related p-tau expression.

In summary, the modulation of individual rapamycin-sensitive genes can achieve the same beneficial effect on neurones as rapamycin.

Example 3 Modulation of mTOR Activity can be Detected by Imaging Metabolic Markers Associated with Rapamycin-Sensitive Genes 3.1 MRI To analyse the effect of mTOR activation and inhibition on the brain, SD rats (170-220 g) were treated with rapamycin (inhibitor of mTOR; 0.2 mg/kg i.p.) and ketamine (activator of mTOR; 30 mg/kg i.p) and neuroimaging results from these experiments were compared to control (untreated) animals. There were three animals (n=3) in each group. Animals were sacrificed and the brain removed and frozen for imaging studies.

Whole organs were fixed in 0.154 M LiCl in 10:1 $H_2O$:formaldehyde prior to MRI experiments. All imaging experiments were performed on a Bruker DMX300 spectrometer, at a $^1H$ NMR resonance frequency of 300 MHz at 289.5±0.2 K. All images were acquired using a 30 mm radiofrequency resonator. Images were acquired using a spin-echo imaging technique [1]. A set of either 7 or 8 equally spaced, coronal slices of 1 mm thickness, with a matrix size of 128×32 pixels and field-of-view of 30 mm×10 mm, were collected along the length of the brain. The recovery time was 15 s, to ensure full T1 relaxation between each acquisition. A T2 map, for each coronal slice, was produced by acquiring between 16 and 24 echo images and varying the echo time from a minimum value of 3 ms to a maximum value of 80 ms. These echo images were then fitted to Equation 1, resulting in a T2 value for each pixel in the coronal slice.

$$M_x = M_0 e^{\frac{-t}{T_2}} \quad (1)$$

where $M_x$ is the signal intensity for each pixel at time t and $M_0$ is the signal intensity at t=0.

A transverse T2 map was acquired for each brain using the method described for the coronal maps. Each image comprised 128×128 pixel array, with a field of view of 3 cm×3 cm. A total of 24 echo images were acquired for each transverse $T_2$ map, with echo times from 3-80 ms. Each transverse slice was positioned in the centre of the brain.

Figure 16A:
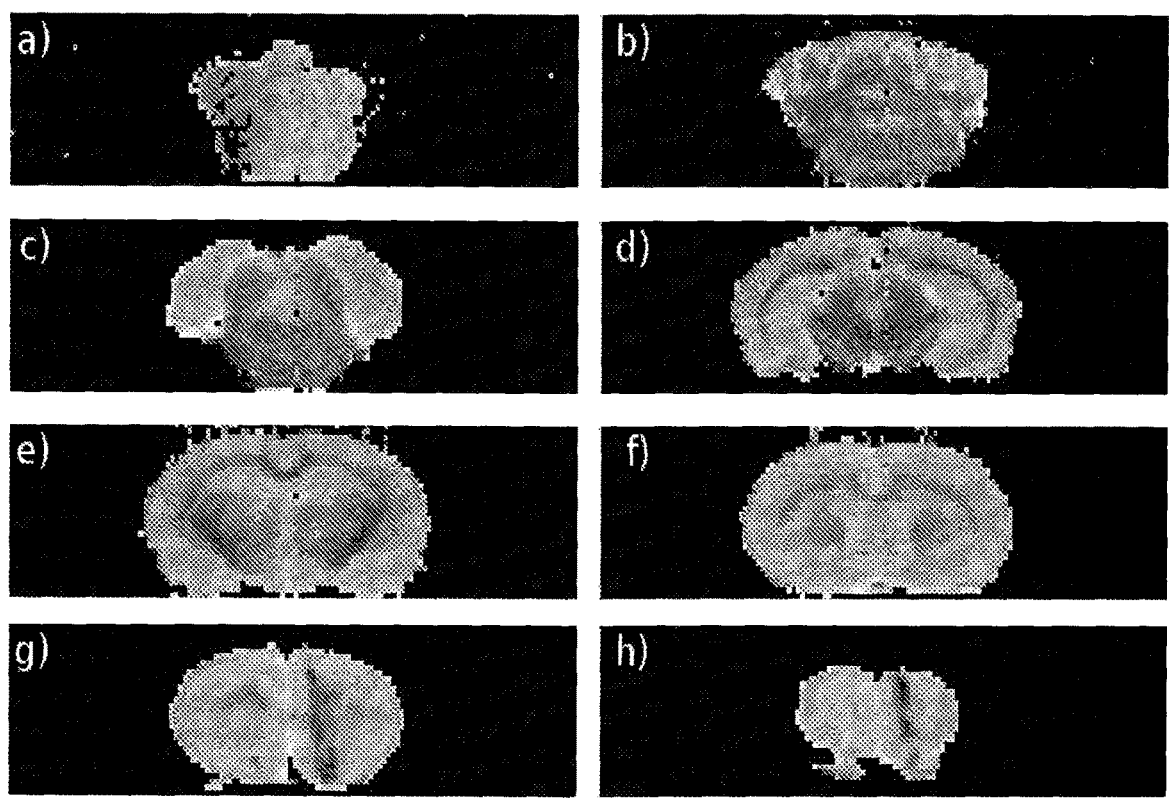
FIG. 16 $T_2$ weighted MRI images of (A) rapamycin-treated animals, (B) ketamine-treated animals and (C) control animals.
Figure 16B:
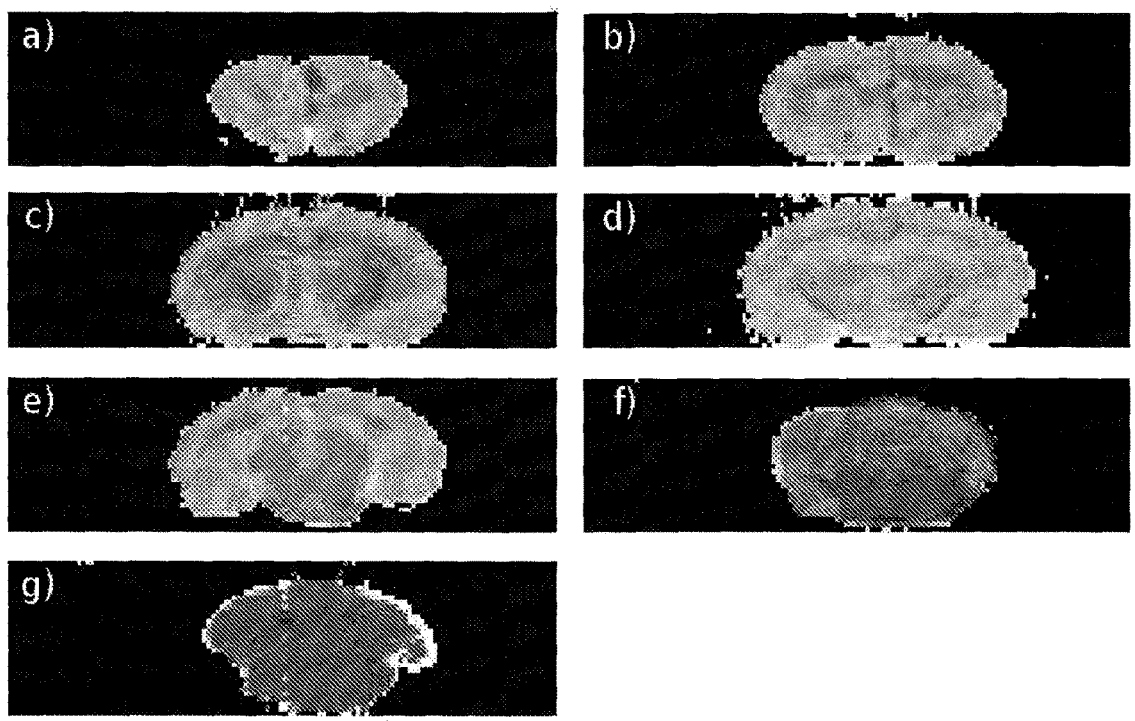
Figure 16C:
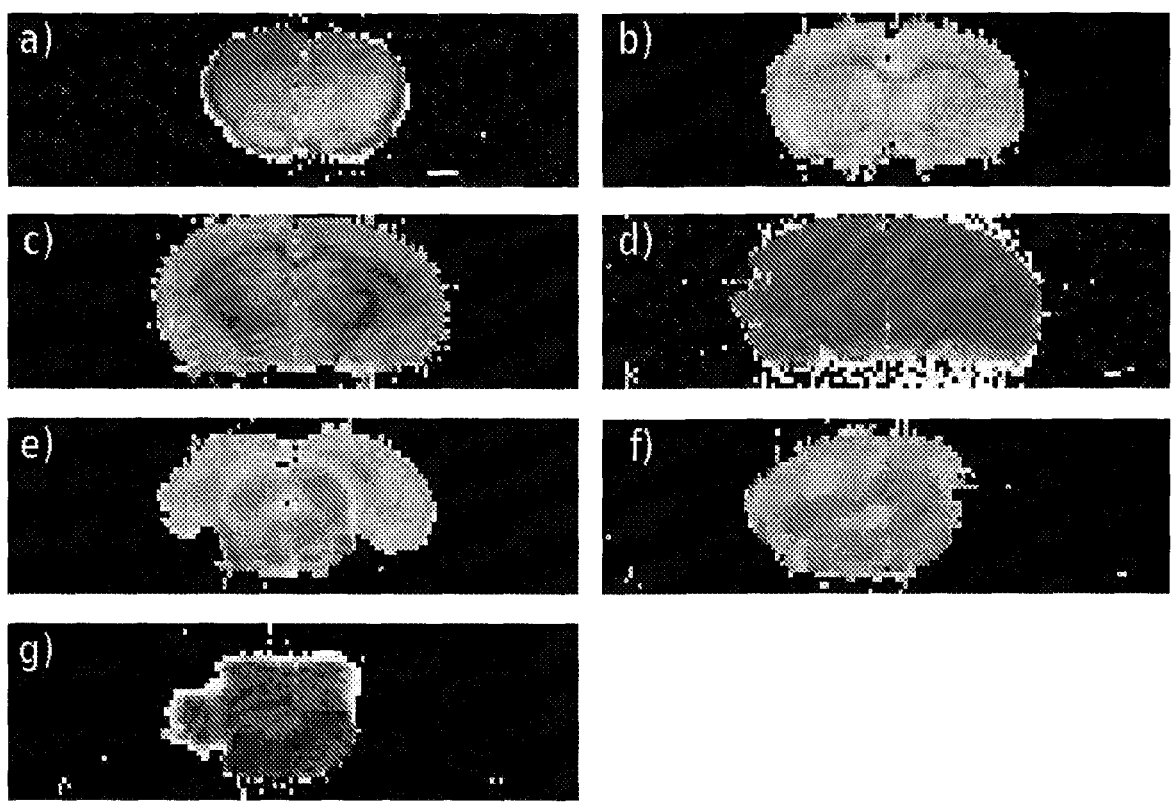

FIGS. 16A-C show clear differences in the T2 weighted MRI images obtained from Rapamycin treated, ketamine treated and Control animals.

3.2 Magnetic Resonance Spectroscopy Imaging

In silico simulations of the effects of mTOR activation and inhibition on the accumulation of choline and creatine have been carried out. These simulations indicated that mTOR modulation leads to significant changes in choline and creatine levels. This is consistent with the possibility of imaging mTOR activation/inhibition in the brain using magnetic spectroscopy.

Methods

All MSI imaging experiments were performed on a Bruker ultrafleXtreme TOF/TOF mass spectrometer. For matrix evaluation, 4 serial sections of thickness 10 μm from sham control brain S2 were acquired using a Leica CM 1850 Cryostat and subsequently thaw mounted onto an ITO coated glass slide. Each section in turn was coated with 15 mL of 20 mg mL$^{-1}$ of CHCA in $CH_3OH$, 0.1% TFA) using an artist airbrush while the remaining 2 sections were covered. Data were collected over the mass range m/z 60-1400. MSI experiments of a single section from each group (Rapa, Ket and Control) were conducted. Data were collected over the mass range m/z 60-1400. Images were acquired with a pixel size of 100 μm×100 μm.

Figure 17:
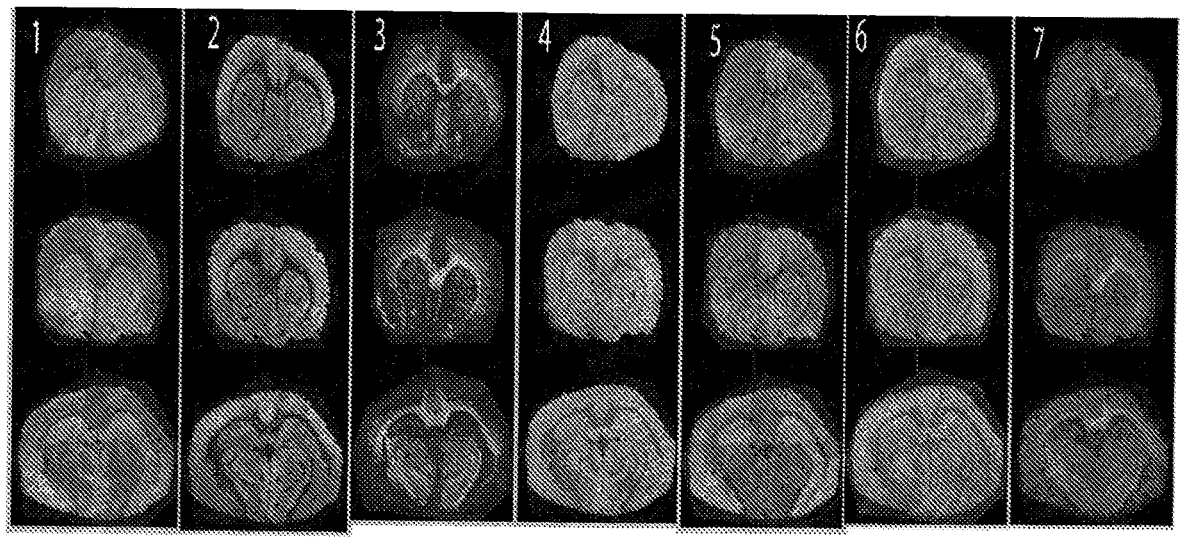
FIG. 17 The effect of mTOR modulation on phosphatidylcholine species in the brain.

The data set contains numerous ion images which demonstrate grey and white anatomical differences and clear differences induced by mTOR inhibition or activation (by rapamycin and ketamine respectively relative to control). These molecular species belong to the group of Phosphatidylcholines (FIG. 17. First row Rapamycin treated; Second row—Ketamine treated; Third row—Control. Columns: 1) m/z 769, 2) m/z 868, 3) m/z 866, 4) m/z 752, 5) m/z 844, 6) m/z 840, 7) m/z 780).

Figure 18:
FIG. 18 The effect of mTOR modulation on choline (A) and creatine (B) levels in the brain.
Figure 18:
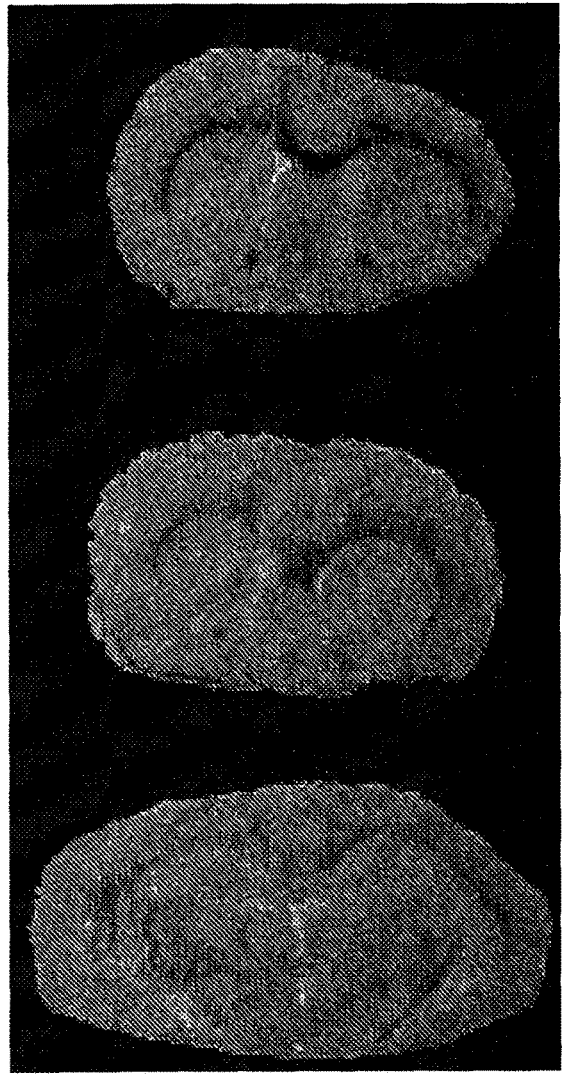

Additionally there is evidence that, similar to the simulated models, mTOR modulation (by rapamycin or Ketamine) leads to measureable changes of choline (FIG. 18A. First row—Rapamycin treated, Second row—Ketamine treated, Third row—Control) and creatine (FIG. 18B. First row—Rapamycin treated, Second row—Ketamine treated, Third row—Control) levels in the brain.

The clear differences in the MRI imaging as well as the differences in the magnetic spectroscopy indicate that changes in brain metabolism induced by mTOR inhibition or activation can clearly be identified using methods already used in human imaging technology.

Example 4 the Effect of Genetic Polymorphisms on the Rapamycin-Regulated Genes is Associated with the Rapamycin Response in Human Lymphocytes from Individual Patients and the Diagnosis of AD 4.1 in Silico Data Mining Existing databases were analysed to identify the mTOR regulated genes on the chromosomal regions identified to be linked to AD (linkage studies, AlzGene).

The AlzGene database identifies the following chromosomal regions in linkage with AD (Table 12)

TABLE 12

| Chromosome | Location (Mb) | Hamshere et al. (2007) LOD (Mb) | Butler et al. (2009) P-value |
|---|---|---|---|
| 1p31.1-q31.1 | 83-185 | | 0.004-0.05 |
| 3q12.3-q25.31 | 103-173 | | 0.03 |
| 6p21.1-q15 | 43-91 | | 0.02 |
| 7pter-q21.11 | 0-78 | | 0.008-0.04 |
| 8p22-p21.1 | 13-28 | | 0.001 |
| 9p22.3-p13.3 | 20-35 | 1.2 (~23 Mb) | |
| 9q21.31-q32 | 80-100 | 2.5 (~101 Mb) | |
| 10p14-q24 | 10-100 | 3.3 (~61 Mb) | |
| 17q24.3-qter | 67-79 | | 0.03 |
| 19p13.3-qter | 8-54 | 2.0 (~52 Mb) | 0.01-0.05 |

Linkage regions in this table are based on results of the joint and meta-analyses of previously published genome-wide linkage (GWL) data (Hamshere, M. L., P. A. Holmans, et al. (2007). Genome-wide linkage analysis of 723 affected relative pairs with late-onset Alzheimer's disease. Hum Mol Genet 16(22): 2703-12; Butler, A. W., M. Y. Ng, et al. (2009). Meta-analysis of linkage studies for Alzheimer's disease—a web resource. Neurobiol. Aging 30(7): 1037-47).

Genes on the regions identified by AlzGene to be in linkage with AD were identified from the Ensembl database (http://www.ensembl.org). Variations on the genes in the region were identified using BioMart and the Ensembl variation 72 database, the contents of which are incorporated herein in their entirety. The results indicate that 22.17% of rapamycin-regulated genes were found on these AD-related chromosomal regions. Interestingly enough a much smaller number of genes were found to be related to AD in prior studies (see Table 13)

SNPs selected for analysis are shown in Table 14. Further details of each of these SNPs can be found in the NCBI database dbSNP (http://www.ncbi.nlm.nih.gov/SNP/). The contents of the dbSNP database entries for each of the SNPs listed in Table 14 are expressly incorporated herein by reference, in particular for the purposes of further defining the location and identity of the SNP.

TABLE 13

| Region | No of genes on region | No of rapa-regulated genes on the region | Genes in region % of whole genome | % genes regulated by Rapa in region | % of Rapa regulated genes in this region | No of genes associated with AD (from existing databases) | % genes associated with AD in this region | % of AD associated genes in this region |
|---|---|---|---|---|---|---|---|---|
| 1p31.1-q31.1 | 1575 | 46 | 7.88 | 2.92 | 4.38 | 13 | 0.83 | 3.19 |
| 3q12.3-q25.31 | 640 | 34 | 3.20 | 5.31 | 3.24 | 5 | 0.78 | 1.23 |
| 6p21.1-q15 | 204 | 10 | 1.02 | 4.90 | 0.95 | 0 | 0.00 | 0.00 |
| 7pter-q21.11 | 991 | 40 | 4.96 | 4.04 | 3.81 | 7 | 0.71 | 1.72 |
| 8p22-p21.1 | 167 | 7 | 0.84 | 4.19 | 0.67 | 5 | 2.99 | 1.23 |
| 9p22.3-p13.3 | 275 | 6 | 1.38 | 2.18 | 0.57 | 2 | 0.73 | 0.49 |

TABLE 13-continued

| Region | No of genes on region | No of rapa-regulated genes on the region | Genes in region % of whole genome | % genes regulated by Rapa in region | % of Rapa regulated genes in this region | No of genes associated with AD (from existing databases) | % genes associated with AD in this region | % of AD associated genes in this region |
|---|---|---|---|---|---|---|---|---|
| 9q21.31-q32 | 430 | 12 | 2.15 | 2.79 | 1.14 | 5 | 1.16 | 1.23 |
| 10p14-q24 | 1072 | 37 | 5.36 | 3.64 | 3.71 | 11 | 1.03 | 2.70 |
| 17q24.3-qter | 335 | 17 | 1.68 | 5.07 | 1.62 | 1 | 0.30 | 0.25 |
| 19p13.3-qter | 1164 | 22 | 5.82 | 1.89 | 2.09 | 11 | 0.95 | 2.70 |
| Total | 6853 | 233 | 34.27 | 3.40 | 22.17 | 60 | 0.88 | 14.74 |

TABLE 14

SNPs selected for analysis

| Code | Variation Name | Chromosome | Position on Chromosome (bp) | Variant Alleles | 1000 genomes global MAF (ALL) | Associated gene with phenotype | Distance to transcript |
|---|---|---|---|---|---|---|---|
| pr1 | rs798893 | 19 | 54793830 | G/C | 0.2921 | LILRB2, intronic | 4072 |
| pr10 | rs725106 | 1 | 190347665 | G/A | 0.375 | FAM5C intronic | 99094 |
| pr11 | rs1341665 | 1 | 159691559 | G/A | 0.3814 | CRP | |
| pr12 | rs1359059 | 1 | 167234166 | G/A | 0.4725 | POU2F1 intronic* | 44038 |
| pr13 | rs1532278 | 8 | 27466315 | T/C | 0.2821 | CLU | 2420 |
| pr14 | rs1801274 | 1 | 161479745 | A/G | 0.4304 | FCGR2A | 395 |
| pr15 | rs2036108 | 8 | 26663100 | C/T | 0.2688 | ADRA1A intronic** | 57433 |
| pr2 | rs811925 | 6 | 106547372 | C/G | 0.136 | PRDM1, intronic**** | 212 |
| pr3 | rs883524 | 8 | 23194591 | T/C | 0.1401 | LOXL2 intronic*** | 3583 |
| pr4 | rs1065457 | 1 | 158324425 | A/G | 0.4469 | CD1E intronic | 646 |
| pr5 | rs1148613 | 1 | 190337300 | A/C | 0.3723 | FAM5C intronic | 106583 |
| pr6 | rs295 | 8 | 19816238 | A/C | 0.2596 | LPL | 4576 |
| pr7 | rs290258 | 9 | 93555739 | A/G | 0.2592 | SYK | |
| pr8 | rs365836 | 7 | 101809851 | A/G | 0.2601 | CUX1 | 117399 |
| pr9 | rs569214 | 8 | 27487790 | G/T | 0.3539 | CLU | 3595 |

The SNPs selected were either SNPs on mTOR-sensitive genes or their direct upstream regulators (POU2F1 is a transcriptional regulator of the mTOR genes A2M, CRP, CSF1R, CYP2C9, ESR1, GSTM3, IL2, IL6, PRKAA2, SPP1, TLR4 from Table 1; ADRA1A is a regulator of mTOR regulated genes: CDKN1B, EGR1, FGF7, FN1, IL6, JUN, LOX, NR4A1, NR4A2 from Table 1; LOXL2 is an upstream regulator of mTOR regulated genes: CDH1, FN1, MMP9 from Table 1; PRDM1 is the upstream regulator of mTOR regulated genes: ESR1, IGHG1, IL10, IL2, IL6, MYC, RELN, SCGN from Table 1).

Methods

The rapamycin response in peripheral lymphocytes was measured in 39 patients. The method has been described previously (Yates et al, Dysfunction of the mTOR pathway is a risk factor for Alzheimer's disease, Acta Neuropathological Communications, 2013).

Genomic DNA was extracted from the same lymphocyte samples (using established protocols). Primers were designed for the SNPs in Table 13 using Primer3 tool. PCR was carried out using the 2×Reddymix PCR master mix (Thermo scientific, AB-0575/DC/LD/B) with a final composition of: 0.625 units ThermoPrime Taq DNA polymerase, 75 mM Tris-HCl (pH 8.8 at 25° C.), 20 mM $(NH_4)_2SO_4$, 1.5 Mm $MgCl_2$, 0.01% (v/v) Tween 20, 0.2 mM each of dATP, dCTP, dGTP and dTTP, and precipitant and red dye for electrophoresis.

PCR Mix was Assembled as Follows:

| | |
|---|---|
| P21 ex2 (Forward Primer) | 0.2 μl |
| P21 ex2' (Reverse Primer) | 0.2 μl |
| Nuclease free water | 15.6 μl |
| 2 x Reddy Mix PCR master mix | 20 μl |

The reagents were added in the volumes as stated above to give a 36 μl Master Mix'. The Master Mix is dispensed in 36 μl aliquots, to which is added 4 μl of test DNA. The PCR was carried out as follows: 95° C. for 5 minutes, followed by 40 cycles of 95° C. for 60 sec, 57° C. for 60 sec and 72° C. for 60 sec.

Following the PCR 4 μl of each sample was denatured in 12 μl SSCP denaturing solution (95% Formamide, 10 mM NaOH, 0.01% w/v xylene cyanole and 0.01% w/v bromophenol blue). Samples were denatured at 95° C. for 6 minutes and placed on ice for at least 10 minutes. Gel electrophoresis was performed using 3% Metaphore agarose+0.5% multipurpose agarose gels, at 400 V for 45 minutes.

The SNPs on the samples lead to single stranded variants that ran at different speeds on the gel (SSCP analysis).

The variant with the lower frequency was regarded the minor allele and labelled "1"; while the more frequent allele was labelled "0".

4.2 Minor Allele Frequencies and the Association of these Alleles with AD.

As the Chi-squared analyses indicated, none of the SNPs investigated was significantly associated on their own with the diagnosis of AD (see Tables 15-29).

TABLE 15

Frequency table & Chi-squared test

| Codes X | | pr1 | |
|---|---|---|---|
| Codes Y | | DG | |

| | Codes X | | |
|---|---|---|---|
| Codes Y | 0 | 1 | |
| CONTROL | 13 | 7 | 20 (51.3%) |
| PROB. AD | 14 | 5 | 19 (48.7%) |
| | 27 (69.2%) | 12 (30.8%) | 39 |

| Chi-squared | 0.058 |
|---|---|
| DF | 1 |
| Significance level | P = 0.8101 |
| Contingency coefficient | 0.038 |

TABLE 16

Frequency table & Chi-squared test

| Codes X | | pr10 | |
|---|---|---|---|
| Codes Y | | DG | |

| | Codes X | | |
|---|---|---|---|
| Codes Y | 0 | 1 | |
| CONTROL | 17 | 3 | 20 (51.3%) |
| PROB. AD | 13 | 6 | 19 (48.7%) |
| | 30 (76.9%) | 9 (23.1%) | 39 |

| Chi-squared | 0.719 |
|---|---|
| DF | 1 |
| Significance level | P = 0.3964 |
| Contingency coefficient | 0.135 |

TABLE 17

Frequency table & Chi-squared test

| Codes X | | pr11 | |
|---|---|---|---|
| Codes Y | | DG | |

| | Codes X | | |
|---|---|---|---|
| Codes Y | 0 | 1 | |
| CONTROL | 14 | 6 | 20 (51.3%) |
| PROB. AD | 13 | 6 | 19 (48.7%) |
| | 27 (69.2%) | 12 (30.8%) | 39 |

| Chi-squared | 0.058 |
|---|---|
| DF | 1 |
| Significance level | P = 0.8101 |
| Contingency coefficient | 0.038 |

TABLE 18

Frequency table & Chi-squared test

| Codes X | | pr12 | |
|---|---|---|---|
| Codes Y | | DG | |

| | Codes X | | |
|---|---|---|---|
| Codes Y | 0 | 1 | |
| CONTROL | 15 | 5 | 20 (51.3%) |
| PROB. AD | 13 | 6 | 19 (48.7%) |
| | 28 (71.8%) | 11 (28.2%) | 39 |

| Chi-squared | 0.010 |
|---|---|
| DF | 1 |
| Significance level | P = 0.9200 |
| Contingency coefficient | 0.016 |

TABLE 19

Frequency table & Chi-squared test

| Codes X | | pr13 | |
|---|---|---|---|
| Codes Y | | DG | |

| | Codes X | | |
|---|---|---|---|
| Codes Y | 0 | 1 | |
| CONTROL | 13 | 7 | 20 (51.3%) |
| PROB. AD | 11 | 8 | 19 (48.7%) |
| | 24 (61.5%) | 15 (38.5%) | 39 |

| Chi-squared | 0.016 |
|---|---|
| DF | 1 |
| Significance level | P = 0.8992 |
| Contingency coefficient | 0.020 |

TABLE 20

Frequency table & Chi-squared test

| Codes X | | pr14 | |
|---|---|---|---|
| Codes Y | | DG | |

| | Codes X | | |
|---|---|---|---|
| Codes Y | 0 | 1 | |
| CONTROL | 15 | 5 | 20 (51.3%) |
| PROB. AD | 15 | 4 | 19 (48.7%) |
| | 30 (76.9%) | 9 (23.1%) | 39 |

| Chi-squared | 0.008 |
|---|---|
| DF | 1 |
| Significance level | P = 0.9301 |
| Contingency coefficient | 0.014 |

TABLE 21

Frequency table & Chi-squared test

| Codes X | | pr15 | |
|---|---|---|---|
| Codes Y | | DG | |

| | Codes X | | |
|---|---|---|---|
| Codes Y | 0 | 1 | |
| CONTROL | 12 | 8 | 20 (51.3%) |
| PROB. AD | 12 | 7 | 19 (48.7%) |
| | 24 (61.5%) | 15 (38.5%) | 39 |

| Chi-squared | 0.016 |
|---|---|
| DF | 1 |
| Significance level | P = 0.8992 |
| Contingency coefficient | 0.020 |

TABLE 22

Frequency table & Chi-squared test

| Codes X | | pr2 | |
|---|---|---|---|
| Codes Y | | DG | |

| | Codes X | | |
|---|---|---|---|
| Codes Y | 0 | 1 | |
| CONTROL | 16 | 4 | 20 (51.3%) |
| PROB. AD | 17 | 2 | 19 (48.7%) |
| | 33 (84.6%) | 6 (15.4%) | 39 |

| Chi-squared | 0.141 |
|---|---|
| DF | 1 |
| Significance level | P = 0.7072 |
| Contingency coefficient | 0.060 |

TABLE 23

Frequency table & Chi-squared test

| Codes X | | pr3 | |
|---|---|---|---|
| Codes Y | | DG | |

| | Codes X | | |
|---|---|---|---|
| Codes Y | 0 | 1 | |
| CONTROL | 10 | 10 | 20 (51.3%) |
| PROB. AD | 10 | 9 | 19 (48.7%) |
| | 20 (51.3%) | 19 (48.7%) | 39 |

| Chi-squared | 0.024 |
|---|---|
| DF | 1 |
| Significance level | P = 0.8759 |
| Contingency coefficient | 0.025 |

TABLE 24

Frequency table & Chi-squared test

| Codes X | | pr4 | |
|---|---|---|---|
| Codes Y | | DG | |

| | Codes X | | |
|---|---|---|---|
| Codes Y | 0 | 1 | |
| CONTROL | 20 | 0 | 20 (51.3%) |
| PROB. AD | 15 | 4 | 19 (48.7%) |
| | 35 (89.7%) | 4 (10.3%) | 39 |

| Chi-squared | 2.683 |
|---|---|
| DF | 1 |
| Significance level | P = 0.1014 |
| Contingency coefficient | 0.254 |

TABLE 25

Frequency table & Chi-squared test

| Codes X | | pr5 | |
|---|---|---|---|
| Codes Y | | DG | |

| | Codes X | | |
|---|---|---|---|
| Codes Y | 0 | 1 | |
| CONTROL | 16 | 4 | 20 (51.3%) |
| PROB. AD | 14 | 5 | 19 (48.7%) |
| | 30 (76.9%) | 9 (23.1%) | 39 |

| Chi-squared | 0.008 |
|---|---|
| DF | 1 |
| Significance level | P = 0.9301 |
| Contingency coefficient | 0.014 |

TABLE 26

Frequency table & Chi-squared test

| Codes X | | pr6 | |
|---|---|---|---|
| Codes Y | | DG | |

| | Codes X | | |
|---|---|---|---|
| Codes Y | 0 | 1 | |
| CONTROL | 9 | 11 | 20 (51.3%) |
| PROB. AD | 11 | 8 | 19 (48.7%) |
| | 20 (51.3%) | 19 (48.7%) | 39 |

| Chi-squared | 0.235 |
|---|---|
| DF | 1 |
| Significance level | P = 0.6278 |
| Contingency coefficient | 0.077 |

TABLE 27

Frequency table & Chi-squared test

| Codes X | pr7 |
| --- | --- |
| Codes Y | DG |

| | Codes X | | |
| --- | --- | --- | --- |
| Codes Y | 0 | 1 | |
| CONTROL | 17 | 3 | 20 (51.3%) |
| PROB. AD | 14 | 5 | 19 (48.7%) |
| | 31 (79.5%) | 8 (20.5%) | 39 |

| | |
| --- | --- |
| Chi-squared | 0.229 |
| DF | 1 |
| Significance level | P = 0.6326 |
| Contingency coefficient | 0.076 |

TABLE 28

Frequency table & Chi-squared test

| Codes X | pr8 |
| --- | --- |
| Codes Y | DG |

| | Codes X | | |
| --- | --- | --- | --- |
| Codes Y | 0 | 1 | |
| CONTROL | 14 | 6 | 20 (51.3%) |
| PROB. AD | 15 | 4 | 19 (48.7%) |
| | 29 (74.4%) | 10 (25.6%) | 39 |

| | |
| --- | --- |
| Chi-squared | 0.074 |
| DF | 1 |
| Significance level | P = 0.7850 |
| Contingency coefficient | 0.044 |

TABLE 29

Frequency table & Chi-squared test

| Codes X | pr9 |
| --- | --- |
| Codes Y | DG |

| | Codes X | | |
| --- | --- | --- | --- |
| Codes Y | 0 | 1 | |
| CONTROL | 16 | 4 | 20 (51.3%) |
| PROB. AD | 16 | 3 | 19 (48.7%) |
| | 32 (82.1%) | 7 (17.9%) | 39 |

| | |
| --- | --- |
| Chi-squared | 0.006 |
| DF | 1 |
| Significance level | P = 0.9403 |
| Contingency coefficient | 0.012 |

However, when combinations of SNPs were investigated, it was found that different combinations of SNPs were significantly associated with the rapamycin response of the individual patient as measured from lymphocytes.

The increase in cell death elicited by rapamycin in the lymphocytes was significantly associated with the combination of pr4, pr1 and pr15 (Table 30).

TABLE 30

Multiple regression

| | |
| --- | --- |
| Dependent Y | f_DEAD_Rapa/f_DEAD_Control |
| Sample size | 39 |
| Coefficient of determination $R^2$ | 0.2305 |

Regression Equation

| Independent variables | Coefficient | Std. Error | $r_{partial}$ | t | P |
| --- | --- | --- | --- | --- | --- |
| (Constant) | 1.0999 | | | | |
| pr4 | 0.7790 | 0.4291 | 0.2933 | 1.815 | 0.0781 |
| pr1 | −0.7175 | 0.3987 | −0.2910 | −1.800 | 0.0805 |
| pr15 | 0.8547 | 0.3871 | 0.3497 | 2.208 | 0.0339 |
| F-ratio | 3.4942 | | | | |
| Significance level | P = 0.026 | | | | |

The relative lengthening of the G1 time induced by rapamycin in the lymphocyte cultures (as defined in Zs Nagy, M Combrinck, M Budge, R McShane. Cell cycle kinesis in lymphocytes in the diagnosis of Alzheimer's disease. Neurosci Letters. 2002, 317, 2, 81-84) was significantly associated with a combination of pr4, pr5, pr7, pr10 and pr11 (Table 31).

TABLE 31

Multiple regression

| | |
| --- | --- |
| Dependent Y | Relative lengthening of G1 time |
| Sample size | 39 |
| Coefficient of determination $R^2$ | 0.4594 |

Regression Equation

| Independent variables | Coefficient | Std. Error | $r_{partial}$ | t | P |
| --- | --- | --- | --- | --- | --- |
| (Constant) | 0.9648 | | | | |
| pr4 | 0.3609 | 0.1148 | 0.4802 | 3.145 | 0.0035 |
| pr5 | −0.3738 | 0.1476 | −0.4033 | −2.532 | 0.0163 |
| pr7 | 0.2966 | 0.1120 | 0.4187 | 2.649 | 0.0123 |
| pr10 | 0.2171 | 0.08211 | 0.4182 | 2.644 | 0.0124 |
| pr11 | 0.3363 | 0.1350 | 0.3979 | 2.492 | 0.0179 |
| F-ratio | 5.6095 | | | | |
| Significance level | P = 0.001 | | | | |

The difference between population doubling level induced by Rapamycin in the lymphocyte cultures was significantly associated with the combination of pr4, pr6, pr12, pr13, pr1, pr8, pr10 and pr11 (Table 32).

TABLE 32

Multiple regression

| | |
| --- | --- |
| Dependent Y | difference between population doubling level induced by Rapamycin |
| Sample size | 39 |
| Coefficient of determination $R^2$ | 0.5932 |

Regression Equation

| Independent variables | Coefficient | Std. Error | $r_{partial}$ | t | P |
| --- | --- | --- | --- | --- | --- |
| (Constant) | 0.7941 | | | | |
| pr4 | −0.3640 | 0.1715 | −0.3614 | −2.123 | 0.0421 |
| pr6 | −0.2529 | 0.1572 | −0.2818 | −1.609 | 0.1182 |
| pr12 | −0.6737 | 0.1633 | −0.6016 | −4.125 | 0.0003 |
| pr13 | −0.2117 | 0.1259 | −0.2936 | −1.682 | 0.1029 |
| pr1 | −0.2015 | 0.1414 | −0.2517 | −1.424 | 0.1646 |
| pr8 | 0.3235 | 0.1766 | 0.3172 | 1.832 | 0.0769 |

TABLE 32-continued

| Multiple regression | | | | | |
|---|---|---|---|---|---|
| pr10 | 0.4391 | 0.1160 | 0.5684 | 3.784 | 0.0007 |
| pr11 | −0.2514 | 0.1759 | −0.2524 | −1.429 | 0.1633 |
| F-ratio | | | 5.4687 | | |
| Significance level | | | P < 0.001 | | |

This association was significantly affected by the plasma homocysteine levels of the patients measured at the time of the blood sample collection. Plasma homocysteine is an independent environmental risk factor of AD and it is also known to affect cell proliferation and cell cycle control functions (Table 33).

TABLE 33

| Multiple regression | |
|---|---|
| Dependent Y | difference between population doubling level induced by Rapamycin |
| Sample size | 39 |
| Coefficient of determination $R^2$ | 0.5954 |

| Regression Equation | | | | | |
|---|---|---|---|---|---|
| Independent variables | Coefficient | Std. Error | $r_{partial}$ | t | P |
| (Constant) | 1.1601 | | | | |
| pr12 | −0.5319 | 0.1663 | −0.4982 | −3.199 | 0.0032 |
| pr3 | −0.4043 | 0.1423 | −0.4544 | −2.840 | 0.0079 |
| pr8 | 0.3558 | 0.1715 | 0.3492 | 2.075 | 0.0464 |
| pr10 | 0.4772 | 0.1190 | 0.5844 | 4.010 | 0.0004 |
| pr11 | −0.3726 | 0.1756 | −0.3562 | −2.122 | 0.0419 |
| pr15 | −0.2380 | 0.1250 | −0.3235 | −1.904 | 0.0663 |
| LHcy | −0.03578 | 0.01574 | −0.3779 | −2.272 | 0.0301 |
| F-ratio | | | 6.5158 | | |
| Significance level | | | P < 0.001 | | |

The change in the G1 time induced by Rapamycin in lymphocyte cultures was significantly associated with pr5, pr7, pr10, pr11 and pr15 (Table 34).

TABLE 34

| Multiple regression | |
|---|---|
| Dependent Y | avg_TG1'/avg_TG1 |
| Sample size | 39 |
| Coefficient of determination $R^2$ | 0.4968 |

| Regression Equation | | | | | |
|---|---|---|---|---|---|
| Independent variables | Coefficient | Std. Error | $r_{partial}$ | t | P |
| (Constant) | 1.2308 | | | | |
| pr5 | −0.8739 | 0.1888 | −0.6274 | −4.628 | 0.0001 |
| pr7 | 0.2405 | 0.1438 | 0.2796 | 1.673 | 0.1038 |
| pr10 | 0.3729 | 0.1063 | 0.5212 | 3.508 | 0.0013 |
| pr11 | 0.5171 | 0.1789 | 0.4495 | 2.891 | 0.0068 |
| pr15 | −0.2051 | 0.1068 | −0.3171 | −1.921 | 0.0634 |
| F-ratio | | | 6.5156 | | |
| Significance level | | | P < 0.001 | | |

The significant association between the SNPs on rapamycin-sensitive genes and the change in the G1 time induced by rapamycin in lymphocyte cultures was altered by plasma homocysteine levels (Table 35).

TABLE 35

| Dependent Y | avg_TG1'/avg_TG1 |
|---|---|
| Sample size | 39 |
| Coefficient of determination $R^2$ | 0.5859 |

| Regression Equation | | | | | |
|---|---|---|---|---|---|
| Independent variables | Coefficient | Std. Error | $r_{partial}$ | t | P |
| (Constant) | 1.6011 | | | | |
| pr5 | −0.7138 | 0.1943 | −0.5569 | −3.673 | 0.0009 |
| pr7 | 0.2224 | 0.1432 | 0.2727 | 1.552 | 0.1311 |
| pr13 | 0.2103 | 0.1296 | 0.2840 | 1.623 | 0.1151 |
| pr3 | −0.2627 | 0.1554 | −0.2949 | −1.691 | 0.1013 |
| pr10 | 0.3731 | 0.1071 | 0.5365 | 3.482 | 0.0015 |
| pr11 | 0.3414 | 0.1894 | 0.3126 | 1.803 | 0.0815 |
| pr15 | −0.1511 | 0.1129 | −0.2374 | −1.338 | 0.1908 |
| LHcy | −0.02881 | 0.01399 | −0.3519 | −2.059 | 0.0483 |
| F-ratio | | | 5.3058 | | |
| Significance level | | | P < 0.001 | | |

The baseline proliferation speed (population doubling time PDT) of the lymphocytes from individual patients also depended on a combination of SNPs (pr4, pr5, pr6, pr12, pr13, pr14, pr1, pr11 and pr15) (Table 36).

TABLE 36

| Multiple regression | |
|---|---|
| Dependent Y | avg_PDT avg PDT |
| Sample size | 39 |
| Coefficient of determination $R^2$ | 0.6676 |
| Regression Equation | |

| Regression Equation | | | | | |
|---|---|---|---|---|---|
| Independent variables | Coefficient | Std. Error | $r_{partial}$ | t | P |
| (Constant) | 9.0610 | | | | |
| pr4 | 12.3884 | 3.2678 | 0.5756 | 3.791 | 0.0007 |
| pr5 | −18.7518 | 6.3679 | −0.4798 | −2.945 | 0.0063 |
| pr6 | 6.3645 | 3.1861 | 0.3478 | 1.998 | 0.0552 |
| pr12 | 14.3572 | 4.6488 | 0.4975 | 3.088 | 0.0044 |
| pr13 | 4.1192 | 2.3607 | 0.3082 | 1.745 | 0.0916 |
| pr14 | −9.8338 | 4.4575 | −0.3791 | −2.206 | 0.0354 |
| pr1 | −4.5430 | 3.0234 | −0.2688 | −1.503 | 0.1438 |
| pr11 | 22.4197 | 4.2262 | 0.7018 | 5.305 | <0.0001 |
| pr15 | 5.8245 | 3.0380 | 0.3354 | 1.917 | 0.0651 |
| F-ratio | | | 6.4729 | | |
| Significance level | | | P < 0.001 | | |

This relationship was also significantly affected by plasma homocysteine levels (Table 37).

TABLE 37

| Multiple regression | |
|---|---|
| Dependent Y | avg_PDT avg PDT |
| Sample size | 39 |
| Coefficient of determination $R^2$ | 0.6897 |

| Regression Equation | | | | | |
|---|---|---|---|---|---|
| Independent variables | Coefficient | Std. Error | $r_{partial}$ | t | P |
| (Constant) | 4.1698 | | | | |
| pr4 | 10.4761 | 3.4882 | 0.4936 | 3.003 | 0.0056 |
| pr5 | −18.3444 | 6.2689 | −0.4839 | −2.926 | 0.0067 |
| pr6 | 7.1093 | 3.1775 | 0.3894 | 2.237 | 0.0334 |
| pr12 | 12.5726 | 4.7438 | 0.4478 | 2.650 | 0.0131 |

TABLE 37-continued

Multiple regression

| | | | | | |
|---|---|---|---|---|---|
| pr13 | 4.3352 | 2.3266 | 0.3321 | 1.863 | 0.0729 |
| pr14 | −9.7313 | 4.3841 | −0.3868 | −2.220 | 0.0347 |
| pr1 | −6.0997 | 3.1717 | −0.3416 | −1.923 | 0.0647 |
| pr11 | 22.9197 | 4.1712 | 0.7203 | 5.495 | <0.0001 |
| pr15 | 5.8184 | 2.9876 | 0.3454 | 1.947 | 0.0616 |
| LHcy | 0.4774 | 0.3386 | 0.2574 | 1.410 | 0.1697 |
| F-ratio | 6.2226 | | | | |
| Significance level | P < 0.001 | | | | |

The change induced in cell proliferation (PDT) by rapamycin was also significantly associated with a combination of SNPs on rapamycin-sensitive genes (pr4, pr5, pr7, pr10, pr11, pr15) (Table 38) and the association was significantly affected by plasma homocysteine levels (Table 39).

TABLE 38

Multiple regression

| Dependent Y | avg_PDT'_PDT avg PDT'/PDT |
|---|---|
| Sample size | 39 |
| Coefficient of determination $R^2$ | 0.4664 |

Regression Equation

| Independent variables | Coefficient | Std. Error | $r_{partial}$ | t | P |
|---|---|---|---|---|---|
| (Constant) | 1.2206 | | | | |
| pr4 | −0.1752 | 0.1156 | −0.2587 | −1.515 | 0.1396 |
| pr5 | −0.6109 | 0.1468 | −0.5927 | −4.162 | 0.0002 |
| pr7 | 0.1782 | 0.1118 | 0.2713 | 1.594 | 0.1207 |
| pr10 | 0.2466 | 0.08267 | 0.4664 | 2.983 | 0.0054 |
| pr11 | 0.3134 | 0.1393 | 0.3695 | 2.249 | 0.0315 |
| pr15 | −0.1211 | 0.08413 | −0.2465 | −1.439 | 0.1598 |
| F-ratio | 4.6613 | | | | |
| Significance level | P = 0.002 | | | | |

TABLE 39

Multiple regression

| Dependent Y | avg_PDT'_PDT avg PDT'/PDT |
|---|---|
| Sample size | 39 |
| Coefficient of determination $R^2$ | 0.5013 |
| $R^2$-adjusted | 0.4078 |

Regression Equation

| Independent variables | Coefficient | Std. Error | $r_{partial}$ | t | P |
|---|---|---|---|---|---|
| (Constant) | 1.5047 | | | | |
| pr5 | −0.5644 | 0.1456 | −0.5653 | −3.877 | 0.0005 |
| pr7 | 0.2353 | 0.1084 | 0.3583 | 2.171 | 0.0375 |
| pr3 | −0.1677 | 0.09174 | −0.3074 | −1.827 | 0.0770 |
| pr10 | 0.2618 | 0.08455 | 0.4801 | 3.096 | 0.0041 |
| pr11 | 0.2222 | 0.1458 | 0.2602 | 1.525 | 0.1372 |
| LHcy | −0.02361 | 0.01068 | −0.3638 | −2.209 | 0.0344 |
| F-ratio | 5.3610 | | | | |
| Significance level | P = 0.001 | | | | |

The baseline length of the G1 time in the lymphocyte cultures was significantly associated with a combination of SNPs on the rapamycin-sensitive genes (pr4, pr5, pr6, pr12, pr14, pr1, pr10, pr11 and pr15) (Table 40).

TABLE 40

Multiple Regression

| Dependent Y | avg_TG1 avg TG1 |
|---|---|
| Sample size | 39 |
| Coefficient of determination $R^2$ | 0.6827 |

Regression Equation

| Independent variables | Coefficient | Std. Error | $r_{partial}$ | t | P |
|---|---|---|---|---|---|
| (Constant) | 7.2421 | | | | |
| pr4 | 9.7224 | 2.0230 | 0.6658 | 4.806 | <0.0001 |
| pr5 | −8.9847 | 4.3131 | −0.3608 | −2.083 | 0.0462 |
| pr6 | 3.8481 | 2.1043 | 0.3215 | 1.829 | 0.0778 |
| pr12 | 10.2202 | 3.0217 | 0.5319 | 3.382 | 0.0021 |
| pr14 | −8.8697 | 3.0202 | −0.4788 | −2.937 | 0.0064 |
| pr1 | −4.4125 | 1.9865 | −0.3813 | −2.221 | 0.0343 |
| pr10 | −2.0526 | 1.4835 | −0.2488 | −1.384 | 0.1770 |
| pr11 | 12.5716 | 2.7938 | 0.6412 | 4.500 | 0.0001 |
| pr15 | 6.6133 | 1.9953 | 0.5242 | 3.314 | 0.0025 |
| F-ratio | 6.9327 | | | | |
| Significance level | P < 0.001 | | | | |

The 'efficacy of Rapamycin' in the lymphocyte cultures was also calculated from the combined effect on cell proliferation time and relative lengthening of the G1 time. This estimate was based on idealised cell culture models. The resulting value was significantly associated with a combination of pr4, pr12, pr10 and pr15 (Table 41).

TABLE 41

Multiple regression

| Dependent Y | efficiency_of_Rapa_from_ideal_model efficiency of Rapa from ideal model |
|---|---|
| Sample size | 39 |
| Coefficient of determination $R^2$ | 0.3972 |

Regression Equation

| Independent variables | Coefficient | Std. Error | $r_{partial}$ | t | P |
|---|---|---|---|---|---|
| (Constant) | 0.6211 | | | | |
| pr4 | −0.5339 | 0.2317 | −0.3676 | −2.305 | 0.0274 |
| pr12 | −0.4911 | 0.1739 | −0.4359 | −2.824 | 0.0079 |
| pr10 | 0.4397 | 0.1636 | 0.4186 | 2.687 | 0.0111 |
| pr15 | −0.4562 | 0.1653 | −0.4279 | −2.761 | 0.0092 |
| F-ratio | 5.6012 | | | | |
| Significance level | P = 0.001 | | | | |

4.3 the Association of the Variants on Rapamycin-Sensitive Genes with AD.

Logistic regression indicates that a combination of pr1, pr10 and plasma homocysteine levels are significantly associated with the diagnosis of AD. The prediction from the model would allow the correct classification of 77.4% of the patients (AUC) (Table 42).

TABLE 42

42.1 Logistic regression

| Dependent Y | DG_AD |
|---|---|
| Select | LHcy > 0 |
| Sample size | 39 |
| Cases with Y = Control | 20 (51.28%) |
| Cases with Y = AD | 19 48.72%) |

TABLE 42-continued

42.2 OVERALL MODEL FIT

| Null model −2 Log Likelihood | 54.040 |
| Significance level | P = 0.0162 |

42.3 COEFFICIENTS AND STANDARD ERRORS

| Variable | Coefficient | Std. Error | P |
|---|---|---|---|
| pr1 = 1 | −1.35043 | 0.90923 | 0.1375 |
| pr10 = 1 | 1.69245 | 0.97968 | 0.0841 |
| LHcy | 0.35371 | 0.14382 | 0.0139 |
| Constant | −3.9978 | | |

42.4 ODDS RATIOS AND 95% CONFIDENCE INTERVALS

| Variable | Odds ratio | 95% CI |
|---|---|---|
| pr1 = 1 | 0.2591 | 0.0436 to 1.5398 |
| pr10 = 1 | 5.4328 | 0.7963 to 37.0631 |
| LHcy | 1.4243 | 1.0745 to 1.8881 |

42.5 CLASSIFICATION TABLE (CUT-OFF VALUE P = 0.5)

| Actual group | Predicted group 0 | Predicted group 1 | Percent correct |
|---|---|---|---|
| Y = Control | 15 | 5 | 75.00% |
| Y = AD | 7 | 12 | 63.16% |
| Percent of cases correctly classified | | | 69.23% |

42.6 ROC CURVE ANALYSIS

| Area under the ROC curve (AUC) | 0.774 |
| Standard Error | 0.0769 |
| 95% Confidence interval | 0.612 to 0.892 |

In summary the data presented indicate that the rapamycin response in peripheral lymphocytes from individual patients is the result of the combination of SNPs on the rapamycin-sensitive genes. The data also show that this genetic association is strongly dependent on an environmental risk factor that has an influence on cell proliferation and cell cycle characteristics, and is itself an independent risk factor for AD.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all aspects and embodiments of the invention described herein are considered to be broadly applicable and combinable with any and all other consistent embodiments, including those taken from other aspects of the invention (including in isolation) as appropriate.

Various publications are cited herein, the disclosures of which are incorporated by reference in their entireties.

The invention claimed is:

1. A method for detection of a combination of human single nucleotide polymorphisms (SNPs) in a human subject, comprising a) obtaining a nucleic acid sample from said human subject;

b) genotyping the sample for a combination of SNPs in rapamycin-sensitive gene(s) CD1E, LPL, POU2F1, CLU, LILRB2, CUX1, FAM5C, and CRP, said combination of SNP alleles being rs1065457 (G), rs295 (C), rs1359059 (A), rs1532278 (C), rs798893 (C), rs365836 (G), rs725106 (A), rs1341665 (A); and c) detecting in said nucleic acid sample from said human subject the presence of a G for rs1065457, a C for rs295, an A for rs1359059, a C for rs1532278, a C for rs798893, a G for rs365836, an A for rs725106, and an A for rs1341665.

2. The method of claim 1, further comprising detection of one or more SNP alleles selected from rs1148613 (C), rs290258 (G), rs2036108 (T), rs1801274 (G), rs811925 (G), rs883524 (C), and rs569214 (T).

3. The method of claim 2, where all SNP alleles are detected.

\* \* \* \* \*